(12) United States Patent
Alstermark et al.

(10) Patent No.: US 7,488,844 B2
(45) Date of Patent: *Feb. 10, 2009

(54) THERAPEUTIC AGENTS

(75) Inventors: Eva-Lotte Lindstedt Alstermark, Höludal (SE); Anna Christina Olsson, Hovås (SE); Lanna Li, Göteborg (SE)

(73) Assignee: AstraZeneca AB (SE)

( * ) Notice: Subject to any disclaimer, the term of this patent is extended or adjusted under 35 U.S.C. 154(b) by 168 days.

This patent is subject to a terminal disclaimer.

(21) Appl. No.: 11/026,806

(22) Filed: Dec. 30, 2004

(65) Prior Publication Data

US 2005/0282822 A1    Dec. 22, 2005

Related U.S. Application Data

(63) Continuation-in-part of application No. 10/499,261, filed as application No. PCT/GB02/05738 on Dec. 18, 2002.

(30) Foreign Application Priority Data

| Dec. 19, 2001 | (SE) | ..................................... 0104334 |
| Dec. 18, 2002 | (WO) | ..................... PCT/GB02/05738 |
| Dec. 18, 2002 | (WO) | ..................... PCT/GB02/05744 |
| Dec. 21, 2002 | (GB) | ................................. 0229931.1 |
| Jun. 18, 2003 | (GB) | ................................. 0314079.5 |
| Dec. 19, 2003 | (WO) | ..................... PCT/GB03/05602 |
| Jun. 17, 2004 | (WO) | ............... PCT/EP2004/006597 |

(51) Int. Cl.
*C07C 229/00* (2006.01)
*C07C 233/12* (2006.01)

(52) U.S. Cl. ....................... 562/442; 562/430; 562/451; 562/507; 562/508; 560/12; 560/42; 560/125; 560/126; 546/245; 546/314; 544/386; 564/161; 564/162

(58) Field of Classification Search ................. 562/430, 562/442, 451, 507, 508; 560/12, 42, 125, 560/126; 546/245, 314; 544/386
See application file for complete search history.

(56) References Cited

U.S. PATENT DOCUMENTS

| 2,928,840 | A | 3/1960 | Shapiro et al. |
| 3,244,398 | A | 4/1966 | Scaramamucci |
| 4,735,959 | A | 4/1988 | Grell |
| 5,210,208 | A | 5/1993 | Huang et al. |
| 5,216,167 | A | 6/1993 | Grell et al. |
| 6,143,769 | A | 11/2000 | Grell et al. |
| 6,258,850 | B1 | 7/2001 | Andersson |
| 6,410,585 | B1 | 6/2002 | Larsen et al. |
| 6,596,751 | B2 | 7/2003 | Fujita et al. |
| 6,884,821 | B1 * | 4/2005 | Shinoda et al. ............. 514/563 |
| 7,256,307 | B2 * | 8/2007 | Alstermark Lindstedt et al. ........... 562/442 |
| 2005/0131068 | A1 | 6/2005 | Alstermark et al. |
| 2005/0148656 | A1 | 7/2005 | Li et al. |
| 2005/0171204 | A1 | 8/2005 | Lindstedt et al. |
| 2006/0111406 | A1 | 5/2006 | Crespo et al. |
| 2006/0142389 | A1 | 6/2006 | Aurell et al. |
| 2006/0142392 | A1 | 6/2006 | Aurell et al. |
| 2006/0194879 | A1 | 8/2006 | Ragnar et al. |
| 2006/0258866 | A1 | 11/2006 | Li et al. |

FOREIGN PATENT DOCUMENTS

| BE | 660266 | 8/1965 |
| DE | 266121 | 10/1913 |
| DE | 807687 | 7/1951 |
| DE | 1935758 | 2/1970 |
| DE | 2130282 | 12/1971 |
| DE | 2160380 | 6/1973 |
| DE | 2828222 | 1/1980 |
| EP | 1167357 | 10/2000 |
| FR | 2245624 | 4/1975 |
| JP | 2001-261612 | 9/2001 |
| WO | WO 92/05145 | 4/1992 |
| WO | WO 96/40201 | 12/1996 |
| WO | WO 99/11606 | 3/1999 |
| WO | WO 99/24442 | 5/1999 |
| WO | WO 00/59889 | 10/2000 |
| WO | WO 00/61582 | 10/2000 |
| WO | WO 00/61585 | 10/2000 |
| WO | WO 00/63196 | 10/2000 |
| WO | WO 00/64888 | 11/2000 |
| WO | WO 00/75103 | 12/2000 |
| WO | WO 01/25181 | * 12/2001 |
| WO | WO 02/44127 | 6/2002 |
| WO | WO 02/44130 | 6/2002 |
| WO | WO 02/064549 | 8/2002 |

(Continued)

OTHER PUBLICATIONS

Adamczyk, Maciej, et al., "Use of Lipase for Regioselective One Pot Amidation and Hydrolysis," HCAPLUS 130:251916 (1999).

(Continued)

*Primary Examiner*—Shailendra Kumar
(74) *Attorney, Agent, or Firm*—Fish & Richardson P.C.

(57) ABSTRACT

The present invention provides a compound of formula I processes for preparing such compounds, their the utility in treating clinical conditions including lipid disorders (dyslipidemias) whether or not associated with insulin resistance, methods for their therapeutic use and pharmaceutical compositions containing them.

20 Claims, No Drawings

FOREIGN PATENT DOCUMENTS

| WO | WO 02/083616 | | 10/2002 |
|---|---|---|---|
| WO | WO 03/051822 | A1 | 3/2003 |
| WO | WO 03/051821 | A1 | 6/2003 |
| WO | WO 2004/056748 | A1 | 7/2004 |
| WO | WO 2004/000789 | A1 | 12/2004 |
| WO | WO 2004/113270 | A1 | 12/2004 |

OTHER PUBLICATIONS

Azzolina, Ornella, et al. "Antiphlogistics Aryloxypropionic Acids: Configurational Study," HCAPLUS 120:133356 (1994).
Bagley, Scott, et al., "Phenoxyphenylacetic Acids and Derivatives Useful as Endothelin Antagonists," HCAPLUS 125:328289 (1996).
Bagley, Scott, et al., "Preparation of Phenoxyphenlacetic Acid-Derivative Endothelin Antagonists," HCAPLUS 125:58490 (1996).
Bagley, Scott, et al., "Preparation of Phenoxyphenylacetates and Analogs as Endothelin Receptor Antagonist," HCAPLUS 129:67607 (1998).
Barrie, S. E. et al., "A Reappraisal of the Effect Upon Thymidine Kinase of Thymidine Derivatives Carrying Large Groups at the 5'-Position," J. Med. Chem., vol. 27, No. 8, pp. 1044-1047 (1984).
Bauer, Klaus, et al., "Phenoxyalkane- and pheroxyalkene Carboxylic Acid, Their Derivatives and Their Use," HCAPLUS 96:7068 (1982).
Beckh, Hansjoerg, et al., "Preparation of Sulfonamides Containing Tetrazolyl Groups and Their Use as Drugs," HCAPLUS 113:59148 (1990).
Berge, John, et al., "Tertiary Phenethylamines," HCAPLUS 104:5623 (1986).
Bohlmann, Ferdinand, et al., "Polyacetylene Compounds CIX. Synthesis of Natrally Occurring, Aromatic substituted Acetylene compounds," HCAPLUS 65:99100 (1966).
Chandrakumar, Nizal Samuel, et al., "LTA4-Hydrolase Inhibitors, Pharmaceutical Compositions, and Methods of Use," HCAPLUS 125:142725 (1996).
Chandrakumar, Nizal Samuel, et al., "Preparation of Heterocyclic LTA4 Hydrolase Inhibitors," HCAPLUS 125:142545 (1996).
De Marchi, F., et al., "Synthesis and Pharmacological Evaluation of Some N-diethylaminoethylaryloxyacetamides and related Compounds," HCAPLUS 79:78343 (1973).
Eakin Murdoch Allan, et al., "Preparation of N-(2-phenoxyethyl)-2-hydroxy-3-thienyloxypropylamines and Analogs as Thermogenic Agents," HCAPLUS 114:163992 (1991).
Fex, Thomas, et al., "Preparation of N-aralkoxy-N-aralkylureas and Analogs as Antitumor Agents," HCAPLUS 124:201795 (1995).
Cantello, Barrie Christian Charles, "2-Aminoethyl Ether Derivatives, and Their Pharmaceutical Compositions," HCAPLUS 101:6799 (1984).
Greenlee, William J., et al., "Phenoxyphenylacetic Acid Derivatives Useful as Endothelin Antagonists," HCAPLUS 122:31129 (1995).
Hankovszky, H. O., et al., "Benzazoles. VI. O-Alkylation of 2-(hydroxyphenyl)- and 2-(hydroxybenzyl) Benzazoles," HCAPLUS 69:106619 (1968).
Harvey, Charolette, M., et al., "Preparation of Endothelin Receptor Antagonists for the Treatment of Emesis," HCAPLUS 125:114587 (1996).
Hayashi, Tetsuyoshi, et al., "Insect Juvenile Hormone Mimetic activity of (4-substituted)phenoxyalkyl Compounds with Various Nitrogenous and Oxygenous Functions and Its Relationship to Their Electrostatic and Stereochemical Properties," HCAPLUS 115:250297 (1991).
Hideg, Kalman, et al., "Alkylbenzazoles," HCAPLUS 69:36127 (1968).
Iijima, Ikuo, et al., "Preparation of [(sulfonylamino)phenoxy]alkanoic acids as Antilipemics," HCAPLUS 118:6741 (1993).
Iijima, Ikuo, et al., "Preparation of p-(sulfonylaminoalkyl)phenoxyalkanoic Acid Derivatives as Antilipidemics," HCAPLUS 121:82733 (1994).
Iwakuma, Takeo, et al., "Phenoxyacetic Acids as Thromboxane A2 Antagonists and Their Preparation," HCAPLUS 112:76612 (1990).
Iwamura, Hajime, et al., "Preparation of Phenolic Ethers as Insecticides," HCAPLUS 116:128359 (1992).
Kraska, Allen R., "Compounds Derived from Formylphenoxyacetic Acid as Antiviral Agents in Animals," HCAPLUS 96:34915 (1982).
Large, M. S., Smith, L.H., "β-Asrenergic Blocking Agents. 23. 1-[(Substituted-amindo)phenoxy]-3-[[(substituted-amido)alkyl]amino]propan-2-ols," J. Med. Chem., vol. 26, No. 3, pp. 352-357 (1983).
Nametkin, et al., "Synthesis of Some Alkyl- and Aralkylphenoxyactic Acids and Their Derivatives," ZH. Obshch. Khim., 21, pp. 2146-2147 (1951).
Nametkin, S. S., et al., "Synthesis of Some Alkyl- and Aralkylphenoxyacetic Acids and Their Derivatives," HCAPLUS 46:48488 (1952).
Penning, Thomas D. et al., "Structure-Activity Relationship Studies on 1-[2-(4-Phenylphenoxy)ethyl]pyrrolidine (SC-22716), a Potent Inhibitor of Leukotriene $A_4$ ($LTA_4$) Hydrolase," HCAPLUS 132:245841 (2000).
Reiffen, Manfred, et al., "Preparation of 2-thiazolyl- and 2-oxazolyl-2-alkoxy-1-aminoethane Derivatives as Antidiabetics and Antiobesity Agents," HCAPLUS 108:221694 (1988).
Reiffen, Manfred, et al., "Preparation of Oxazole- and Thiazoleethanamines as Antidiabetics, Antiatherosclerotics, and Antiobesity Agents," HCAPLUS 108:150463 (1988).
Sano, Hidekazu, et al., "Reversible Thermal Printing Material Containing Imide Compound as Decoloration Accelerator," HCAPLUS 136:191709 (2002).
Sano, Hidekazu, et al., "Reversible Thermal Recording Material Containing Cyano Compound as Decoloration Accelerator," HCAPLUS 136:175486 (2002).
Sasaki, Yasuhiko, et al., "Preparation of 4-(2-sulfonylaminoethyl)phenol Ethers as Thromboxane A2 Antagonists," HCAPLUS 116:105828 (1992).
Stubenrauch, Gerd, et al., "Fungicidal 1,2,4-triazol-1-yl Compounds," 94:15736 (1981).
Svab, A., et al., "Some 3-substituted Derivatives of 5-methylisoxazole with an Antiparasitic Effect," HCAPLUS 100:82623 (1984).
Tamiz, Amir P., et al., "Structure-Activity Relationship of N-(Phenylalkyl) Cinnamides as Novel NR2B Subtype-Selective NMDA Receptor Antagonists," HCAPLUS 131:252095 (1999).
Willson T. M. et al.: "The PPARs: From Orphan Receptor to Drug Discovery," Journal of Medicinal Chemistry, American Chemical Society, vol. 43, No. 4, pp. 527-550 (2000).
Witte Ernst Christian, et al., "Phenoxyalkylcarboxylic Acid Derivatives," HCAPLUS 92:6247 91980).
Witte, Ernst Christian, et al., "Preparation of (sulfonylaminoalkyl)phenoxyacyl Amino Acids as Cardiovascular Agents," HCAPLUS 115:280555 (1991).
Witte, Ernst, et al., "N-[[(aminoalkyl)phenyl]alkyl]- and N-[[(aminoalkoxy)phenyl]alkyl]sulfonamides, a Process for Their Preparation and Their Use as Thromboxane Antagonists," HCAPLUS 117:170993 (1992).
Kirk-Othmer Encyclopedia of Chemical Technology, Copyright © 2002 by John Wiley & Sons, Inc., pp. 95-147, Article Online Posting Date: Aug. 16, 2002.
Randle, Philip J. et al., "Glucose Fatty Acid Interactions and the Regulation of Glucose Disposal", Journal of Cellular Biology 55S:1-11 (1994).
Rouhi, A. Muareen et al., "The Right Stuff. From research and development to the clinic, getting drug crystals right is full of pitfalls", Chemical & Engineering News, pp. 32-35 (2003).
Silverman, Richard B., "The Organic Chemistry of Drug Design and Drug Action", pp. 19-23 (1992).
Wikipidea website on "Prodrug" http://en.wikipedia.org/wiki/Prodrug dated Dec. 5, 2006.

* cited by examiner

THERAPEUTIC AGENTS

CROSS-REFERENCE TO RELATED APPLICATIONS

This application is a continuation-in-part application of and claims priority to U.S. application Ser. No. 10/499,261, filed on Jun. 18, 2004, which application is the national phase application under 35 U.S.C. § 371 of International Application No. PCT/GB02/05738, which has an International filing date of Dec. 18, 2002, and which designated Swedish Application Serial No. 0104334-8, filed Dec. 19, 2001, as priority; and claims priority to U.S. application Ser. No.10/499,378, filed on Jun. 16, 2004, which application is the national phase application under 35 U.S.C. § 371 of International Application No. PCT/GB02/05744, which has an International filing date of Dec. 18, 2002, and which designated Swedish Application Serial No. 0104334-8, filed Dec. 19, 2001, as priority; and claims priority to U.S. application Ser. No. 10/499,893, filed on Jun. 23, 2004, which application is the national phase application under 35 U.S.C. § 371 of PCT International Application No. PCT/GB03/05602, filed Dec. 19, 2003, which claims priority to United Kingdom Application Serial No. 0229931.1, filed Dec. 21, 2002; and claims priority to U.S. application Ser. No. 10/518,777 entitled Carboxylic Derivatives, filed on Dec. 17, 2004, which application is the national phase application under 35 U.S.C. § 371 of PCT International Application No. PCT/EP2004/006597, filed Jun. 17, 2004, which claims priority to United Kingdom Application Serial No. 0314079.5, filed Jun. 18, 2003. The contents of each of these applications is hereby incorporated by reference in its entirety.

TECHNICAL FIELD

This invention relates to novel compounds, to processes for preparing such compounds, and to their utility in treating clinical conditions including lipid disorders (dyslipidemias) whether or not associated with insulin resistance and other manifestations of the metabolic syndrome, to methods for their therapeutic use and to pharmaceutical compositions containing them.

BACKGROUND

The metabolic syndrome including type 2 diabetes mellitus, refers to a cluster of manifestations including insulin resistance with accompanying hyperinsulinaemia, possibly type 2 diabetes mellitus, arterial hypertension, central (visceral) obesity, dyslipidaemia observed as deranged lipoprotein levels typically characterised by elevated VLDL (very low density lipoproteins), small dense LDL particles and reduced HDL (high density lipoprotein) concentrations and reduced fibrinolysis.

Recent epidemiological research has documented that individuals with insulin resistance run a greatly increased risk of cardiovascular morbidity and mortality, notably suffering from myocardial infarction and stroke. In type 2 diabetes mellitus atherosclerosis related conditions cause up to 80% of all deaths.

In clinical medicine there is awareness of the need to increase the insulin sensitivity in patients with the metabolic syndrome and thus to correct the dyslipidaemia which is considered to cause the accelerated progress of atherosclerosis. However, currently this is not a universally accepted diagnosis with well-defined pharmacotherapeutic indications.

The S-enantiomer of the compound of formula C below

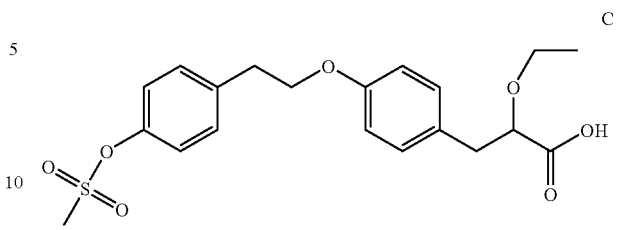

C 2-ethoxy-3-[4-(2-{4-methanesulfonyloxyphenyl}ethoxy) phenyl]propanoic acid, is disclosed in PCT Publication Number WO99/62872. This compound is reported to be a modulator of peroxisome proliferator-activated receptors (PPAR, for a review of the PPARs see T. M. Willson et al, J Med Chem 2000, Vol 43, 527) and has combined PPARα/PPARγ agonist activity (Structure, 2001, Vol 9, 699, P. Cronet et al). This compound is effective in treating conditions associated with insulin resistance.

Surprisingly a series of compounds has now been found which are selective PPARα modulators.

SUMMARY

In one embodiment, the invention features A compound of formula (I)

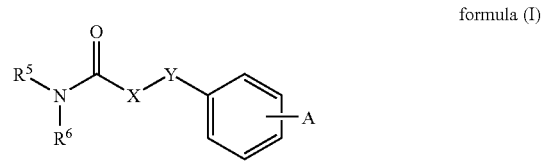

formula (I)

wherein,
A is situated in the ortho, meta or para position and represents

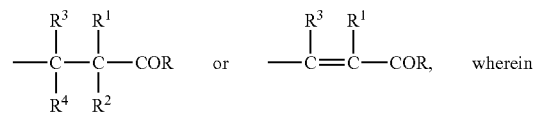

R is H or alkyl;
—$OR^a$, wherein $R^a$ represents hydrogen, alkyl, aryl or alkylaryl;
—$NR^aR^b$, wherein $R^a$ and $R^b$ are the same or different and $R^a$ is as defined above and $R^b$ represents hydrogen, alkyl, aryl, alkylaryl, cyano, —OH, —Oalkyl, —Oaryl, —Oalkylaryl, —$COR^c$ or —$SO_2R^d$, wherein $R^c$ represents hydrogen, alkyl, aryl or alkylaryl and $R^d$ represents alkyl, aryl or alkylaryl;
$R^1$ is alkyl, aryl, alkenyl, alkynyl, or when A is

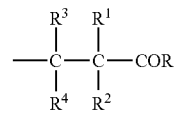

$R^1$ can also be cyano;

—$OR^e$, wherein $R^e$ is alkyl, acyl, aryl or alkylaryl;

—O—$[CH_2]_m$—$OR^f$, wherein $R^f$ represents hydrogen, alkyl, acyl, aryl or alkylaryl and m represents an integer 1-8;

—$OCONR^aR^c$, wherein $R^a$ and $R^c$ are as defined above;

—$SR^d$, wherein $R^d$ is as defined above;

—$SO_2NR^aR^f$, wherein $R^f$ and $R^a$ are as defined above;

—$SO_2OR^a$, wherein $R^a$ is as defined above;

—$COOR^d$, wherein $R^d$ is as defined above;

$R^2$ is hydrogen, halogen, alkyl, aryl, or alkylaryl, $R^3$ and $R^4$ are the same or different and each represents hydrogen, alkyl, aryl, or alkylaryl;

Y represents O, S or a single bond;

n represents 1, 2, 3 or 4;

X is alkyl;

$R^5$ and $R^6$ independently represent hydrogen, $C_{1-13}$alkyl, $C_{2-10}$alkenyl or $C_{2-10}$alkynyl each of which is optionally substituted by one or more of the following which may be the same or different: $C_{3-8}$cycloalkyl, $C_{3-8}$cycloalkenyl, aryl, heterocyclyl, heteroaryl, $C_{1-8}$alkoxy (optionally substituted by one or more fluoro), $C_{3-8}$cycloalkoxy, $C_{3-8}$cycloalkenyloxy, aryloxy, heterocyclyloxy, heteroaryloxy, $C_{3-8}$cycloalkyl $C_{1-8}$alkoxy, aryl $C_{1-8}$alkoxy, heterocyclyl $C_{1-8}$ alkoxy or heteroaryl $C_{1-8}$ alkoxy, fluorine or hydroxy and wherein each of these substituents may optionally be substituted on carbon with one or more substituents which may be the same or different and selected from $C_{1-8}$alkyl, $C_{3-8}$cycloalkyl (optionally substituted by $C_{1-8}$alkyl, $C_{1-8}$alkoxy (optionally substituted by one or more fluoro), halogen, hydroxy, nitro or cyano), aryl (optionally substituted by $C_{1-8}$alkyl, $C_{1-8}$alkoxy (optionally substituted by one or more fluoro), halogen, hydroxy, nitro or cyano), heterocyclyl (optionally substituted by $C_{1-6}$alkyl on any nitrogen), heteroaryl (optionally substituted by $C_{1-8}$alkyl, $C_{1-8}$alkoxy (optionally substituted by one or more fluoro), halogen, hydroxy, nitro or cyano), $C_{1-8}$alkoxy (optionally substituted by one or more fluoro), $C_{3-8}$cycloalkoxy, $C_{3-8}$ cycloalkyl $C_{1-8}$alkoxy, aryloxy (optionally substituted by $C_{1-8}$alkyl, $C_{1-8}$alkoxy (optionally substituted by one or more fluoro), halogen, hydroxy, nitro or cyano), aryl $C_{1-8}$alkoxy (wherein the aryl part is optionally substituted by $C_{1-8}$alkyl, $C_{1-8}$alkoxy (optionally substituted by one or more fluoro), halogen, hydroxy, nitro or cyano), halogen, amino, nitro, hydroxy, methylsulfonyl, methylsulfonyloxy, cyano or methylenedioxy, or $R^5$ and $R^6$ independently represent $C_3$-$C_8$ cycloalkyl; $C_3$-$C_8$ cycloalkenyl; aryl; heterocyclyl; or heteroaryl; wherein each of these groups is optionally substituted by one or more of the following: $C_{1-8}$alkyl, $C_{1-8}$alkoxy (optionally substituted by one or more fluoro), halogen, hydroxy, nitro or cyano), aryl (optionally substituted by $C_{1-8}$alkyl, $C_{1-8}$alkoxy (optionally substituted by one or more fluoro), halogen, hydroxy, nitro or cyano;

or $R^5$ and $R^6$ together with the nitrogen atom to which they are attached form a single or a fused heterocyclic system.

In some embodiments, when A is $CH_2CH(OC_2H_5)$ $COOC_2H_5$ or $CH_2CH(OC_2H_5)COOH$; Y is O; and $R^5$ represents a $C_{2-4}$alkyl group then $R^6$ does not represent a group of formula

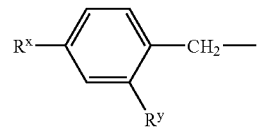

wherein $R^x$ represents chloro, trifluoromethyl or trifluoromethoxy, $R^y$ represents H or fluoro.

In some embodiment, when A is $CH_2CH(OC_2H_5)$ $COOC_2H_5$ or $CH_2CH(OC_2H_5)COOH$; Y is O; n is 1 and $R^5$ represents hexyl or heptyl then $R^6$ does not represent a group of formula

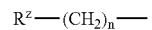

wherein $R^z$ represents phenyl, 2,4-difluorophenyl or cyclohexyl, and n is 1 or 2.

In some embodiments, the compound of formula (I) is not one of the following compounds:

(2S)-4-[2-[[2-[[(2,6-dichlorophenyl)methyl]thio]ethyl] amino]-2-oxoethoxy]-α-methoxy-benzenepropanoic acid;

(2S)-4-[2-[butyl(1-phenylethyl)amino]-2-oxoethoxy]-α-methoxy-benzenepropanoic acid;

(2S)-α-methoxy-4-[2-oxo-2-[[2-(3-pyridinyl) ethyl] amino]ethoxy]-benzenepropanoic acid;

(2S)-α-methyl-4-[2-oxo-2-[[2-(4-phenoxyphenyl) ethyl] amino]ethoxy]-α-phenoxy-benzenepropanoic acid;

(2S)-α-methoxy-4-[2-[(1-methyl-3-phenylpropyl) amino]-2-oxoethoxy]-benzenepropanoic acid;

(2S)-α-methoxy-4-[2-oxo-2-[[2-(4-phenoxyphenyl)ethyl] amino]ethoxy]-benzenepropanoic acid;

(2S)-α-methoxy-4-[2-oxo-2-[4-[4-(trifluoromethyl)phenyl]-1-piperazinyl]ethoxy]-benzenepropanoic acid;

(2S)-4-[2-[[2-(4-bromophenyl)ethyl]amino]-2-oxoethoxy]-α-methoxy-benzenepropanoic acid;

(2S)-4-[2-[4-[(4-chlorophenyl)phenylmethyl]-1-piperazinyl]-2-oxoethoxy]-α-methoxy-benzenepropanoic acid;

(2S)-4-[2-[[2-[ethyl(3-methylphenyl)amino]ethyl] amino]-2-oxoethoxy]-α-methoxy-benzenepropanoic acid;

α-methoxy-α-methyl-4-[2-oxo-2-[[2-(4-phenoxyphenyl) ethyl]amino]ethoxy]-benzenepropanoic acid;

(2S)-α-methoxy-4-[2-[(3-methylbutyl)amino]-2-oxoethoxy]-benzenepropanoic acid;

(2S)-4-[2-[4-(diphenylmethyl)-1-piperazinyl]-2-oxoethoxy]-α-methoxy-benzenepropanoic acid;

(2S)-4-[2-(heptylamino)-2-oxoethoxy]-α-methoxy -α-methyl-benzenepropanoic acid;

4-[2-[4-(2-fluorophenyl)-1-piperazinyl]-2-oxoethoxy]-α-methoxy-, benzenepropanoic acid;

(2S)-4-[2-[4-(4-chlorobenzoyl)-1-piperidinyl]-2-oxoethoxy]-α-methoxy-, benzenepropanoic acid;

(2S)-4-[2-[ethyl[(3-methylphenyl)methyl]amino]-2-oxoethoxy]-α-methoxy-benzenepropanoic acid;

(2S)-α-methoxy-4-[2-oxo-2-[(4-phenoxyphenyl)amino] ethoxy]-benzenepropanoic acid;

(2S)-α-methoxy-4-[2-[(1-methylhexyl)amino]-2-oxoethoxy]-benzenepropanoic acid;

(2S)-4-[2-[([1,1'-biphenyl]-4-ylmethyl)amino]-2-oxoethoxy]-α-methoxy-benzenepropanoic acid;

3-[2-[[cis-4-(1,1-dimethylethyl)cyclohexyl]amino]-2-oxoethoxy]-α-methoxy-benzenepropanoic acid;
(2S)-4-[2-[4-(3-chlorophenyl)-1-piperazinyl]-2-oxoethoxy]-α-methoxy-benzenepropanoic acid;
(2S)-α-methoxy-4-[2-[methyl[(1S)-1-phenylethyl]amino]-2-oxoethoxy]-benzenepropanoic acid;
(2S)-α-methoxy-4-[2-[4-(4-methylphenyl)-1-piperazinyl]-2-oxoethoxy]-benzenepropanoic acid;
(2S)-α-methoxy-4-[2-[[3-(methylphenylamino)propyl]amino]-2-oxoethoxy]-benzenepropanoic acid;
(2S)-4-[2-(cyclobutylamino)-2-oxoethoxy]-α-methoxy-benzenepropanoic acid;
(2S)-α-methyl-4-[2-oxo-2-[[2-(4-phenoxyphenyl)ethyl]amino]ethoxy]-α-[4-(trifluoromethoxy)phenoxy]-benzenepropanoic acid;
(2S)-4-[2-(heptylamino)-2-oxoethoxy]-α-methoxy-benzenepropanoic acid;
(2S)-4-[2-[4-(4-fluorophenyl)-1-piperazinyl]-2-oxoethoxy]-α-methoxy-benzenepropanoic acid;
(2S)-α-methoxy-4-[2-[[(1S)-1-(1-naphthalenyl)ethyl]amino]-2-oxoethoxy]-benzenepropanoic acid;
(2S)-α-methoxy-4-[2-oxo-2-[[(1R)-1-phenylethyl](phenylmethyl)amino]ethoxy]-benzenepropanoic acid;
(2S)-4-[2-[(3,3-diphenylpropyl)amino]-2-oxoethoxy]-α-methoxy-benzenepropanoic acid;
(2S)-4-[2-[[trans-4-(1,1-dimethylethyl)cyclohexyl]amino]-2-oxoethoxy]-α-methoxy-benzenepropanoic acid;
(2S)-α-methyl-4-[2-oxo-2-[[2-(4-phenoxyphenyl)ethyl]amino]ethoxy]-α-phenoxy-, ethyl ester-benzenepropanoic acid;
(2S)-4-[2-[(2,2,3,3,4,4,4-heptafluorobutyl)amino]-2-oxoethoxy]-α-methoxy-benzenepropanoic acid;
(2S)-4-[2-(3,4-dihydro-2(1H)-isoquinolinyl)-2-oxoethoxy]-α-methoxy-benzenepropanoic acid;
(2S)-3-[2-[[2-(4-ethylphenyl)ethyl]amino]-2-oxoethoxy]-α-methoxy-benzenepropanoic acid;
(2S)-α-methoxy-4-[2-[(1-naphthalenylmethyl)amino]-2-oxoethoxy]-benzenepropanoic acid;
(2S)-4-[2-[[(4-chlorophenyl)phenylmethyl]amino]-2-oxoethoxy]-α-methoxy-benzenepropanoic acid;
(2S)-α-methoxy-4-[2-oxo-2-[[2-(2-pyridinyl)ethyl]amino]ethoxy]-benzenepropanoic acid;
(2S)-α-methoxy-4-[2-oxo-2-[[(1S)-1-phenylethyl]amino]ethoxy]-benzenepropanoic acid;
(2S)-4-[2-(cyclopentylamino)-2-oxoethoxy]-α-methoxy-benzenepropanoic acid;
(2S)-4-[2-[4-[bis(4-fluorophenyl)methyl]-1-piperazinyl]-2-oxoethoxy]-α-methoxy-benzenepropanoic acid;
4-[2-[cyclohexyl[2-(4-ethylphenyl)ethyl]amino]-2-oxoethoxy]-α-ethoxy-benzenepropanoic acid;
(2S)-4-[2-[(1,3-benzodioxol-5-ylmethyl)amino]-2-oxoethoxy]-α-methoxy-benzenepropanoic acid;
D-Phenylalanine, N-[[4-[(2S)-2-carboxy-2-methoxyethyl]phenoxy]acetyl]-, α-methyl ester;
(2S)-4-[2-[4-[(4-fluorophenyl)methyl]-1-piperazinyl]-2-oxoethoxy]-α-methoxy-benzenepropanoic acid;
α-methoxy-3-[2-oxo-2-[(4-phenoxyphenyl)amino]ethoxy]-benzenepropanoic acid;
(2S)-α-methoxy-4-[2-[(1-methylbutyl)amino]-2-oxoethoxy]-benzenepropanoic acid;
(2S)-α-methoxy-4-[2-[methyl(1-naphthalenylmethyl)amino]-2-oxoethoxy]-benzenepropanoic acid;
(2S)-3-[2-[[trans-4-(1,1-dimethylethyl)cyclohexyl]amino]-2-oxoethoxy]-α-methoxy-benzenepropanoic acid;
(2S)-4-[2-[4-[(4-chlorophenyl)methyl]-1-piperazinyl]-2-oxoethoxy]-α-methoxy-benzenepropanoic acid;
(2S)-4-[2-[4-(4-fluorobenzoyl)-1-piperidinyl]-2-oxoethoxy]-α-methoxy-benzenepropanoic acid;
(2S)-4-[2-[ethyl[(2-fluorophenyl)methyl]amino]-2-oxoethoxy]-α-methoxy-benzenepropanoic acid;
(2S)-α-methoxy-4-[2-[[2-(4-methoxyphenoxy)ethyl]amino]-2-oxoethoxy]-benzenepropanoic acid;
(2S)-4-[2-[(1,3-dimethylbutyl)amino]-2-oxoethoxy]-α-methoxy-benzenepropanoic acid;
(2S)-α-(4-fluorophenoxy)-α-methyl-4-[2-oxo-2-[[2-(4-phenoxyphenyl)ethyl]amino]ethoxy]-benzenepropanoic acid;
(2S)-4-[2-[(3,3-dimethylbutyl)amino]-2-oxoethoxy]-α-methoxy-benzenepropanoic acid;
(2S)-4-[2-[4-(4-chlorophenyl)-3-methyl-1-piperazinyl]-2-oxoethoxy]-α-methoxy-benzenepropanoic acid;
(2S)-α-methoxy-4-[2-oxo-2-[[(1R)-1-phenylethyl]amino]ethoxy]-benzenepropanoic acid;
(2S)-4-[2-[4-(4-acetylphenyl)-1-piperazinyl]-2-oxoethoxy]-α-methoxy-benzenepropanoic acid;
(2S)-4-[2-[(3-ethoxy-3-oxopropyl)(phenylmethyl)amino]-2-oxoethoxy]-α-methoxy-benzenepropanoic acid;
(2S)-4-[2-[[cis-4-(1,1-dimethylethyl)cyclohexyl]amino]-2-oxoethoxy]-α-methoxy-benzenepropanoic acid;
(2S)-α-ethyl-4-[2-oxo-2-[[2-(4-phenoxyphenyl)ethyl]amino]ethoxy]-α-phenoxy-benzenepropanoic acid;
(2S)-4-[2-(hexylamino)-2-oxoethoxy]-α-methoxy-benzenepropanoic acid;
(2S)-α-methoxy-4-[2-oxo-2-[(2-phenylethyl)(phenylmethyl)amino]ethoxy]-benzenepropanoic acid;
or
(2S)-4-[2-[ethyl[2-(4-methoxyphenyl)-1-methylethyl]amino]-2-oxoethoxy]-α-methoxy-benzenepropanoic acid.

Definitions:

The following definitions shall apply throughout the specification and the appended claims with regard to the group A.

Unless otherwise stated or indicated, the term "alkyl" preferably denotes a straight or branched, substituted or unsubstituted alkyl group having from 1 to 6 carbon atoms or a cyclic alkyl having from 3 to 6 carbon atoms. The term "lower alkyl" denotes a straight or branched, substituted or unsubstituted alkyl group having from 1 to 3 carbon atoms or a cyclic alkyl having 3 carbon atoms. Examples of said alkyl and lower alkyl include methyl, ethyl, n-propyl, isopropyl, n-butyl, iso-butyl, sec-butyl, t-butyl and straight- and branched-chain pentyl and hexyl as well as cyclopropyl, cyclobutyl, cyclopentyl and cyclohexyl.

Unless otherwise stated or indicated, the term "alkoxy" preferably denotes a group O-alkyl, wherein alkyl is as defined above.

Unless otherwise stated or indicated, the term "halogen" generally means fluorine, chlorine, bromine or iodine.

Unless otherwise stated or indicated, the term "aryl" preferably denotes a substituted or unsubstituted phenyl, furyl, thienyl or pyridyl group, or a fused ring system of any of these groups, such as naphthyl.

Unless otherwise stated or indicated, the term "substituted" preferably denotes an alkyl or an aryl group as defined above which is substituted by one or more alkyl, alkoxy, halogen, amino, thiol, nitro, hydroxy, acyl, aryl or cyano groups.

Unless otherwise stated or indicated, the term "alkylaryl" preferably denotes a

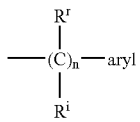

wherein n is an integer 1 to 6 and R' and R' are the same or different and each represents hydrogen or an alkyl or aryl group as defined above.

Unless otherwise stated or indicated, the term "acyl" preferably denotes a group

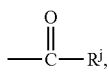

wherein R' is hydrogen, alkyl, alkoxy, aryl and alkylaryl as defined above.

Unless otherwise stated or indicated, the terms "alkenyl" and "alkynyl" preferably denote a straight or branched, substituted or unsubstituted unsaturated hydrocarbon group having one or more double or triple bonds and having a maximum of 6 carbon atoms, preferably 3 carbon atoms.

Unless otherwise stated or indicated the term "protective group" ($R^p$) preferably denotes a protecting group as described in the standard text "Protecting groups in Organic Synthesis", 2nd Edition (1991) by Greene and Wuts. The protective group may also be a polymer resin such as Wang resin or 2-chlorotrityl chloride resin.

For the groups other than A the following definitions apply.

"Cycloalkyl" preferably means a non-aromatic monocyclic or multicyclic ring system of from 3 carbon atoms up to 10 carbon atoms.

"Aryl" preferably means an aromatic monocyclic or multicyclic ring system of up to 14 carbon atoms.

"Heterocyclyl" preferably means a non-aromatic monocyclic or multicyclic ring system of up to 14 carbon atoms, containing at least one heteroatom.

"Heteroaryl" preferably means an aromatic monocyclic or multicyclic ring system of up to 14 carbon atoms, containing at least one heteroatom.

The term "prodrug" as used in this specification preferably includes derivatives of the carboxylic acid group which are converted in a mammal, particularly a human, into the carboxylic acid group or a salt or conjugate thereof. It should be understood that, whilst not being bound by theory, it is believed that most of the activity associated with the prodrugs arises from the activity of the compound of a formula described herein into which the prodrugs are converted. Prodrugs can be prepared by routine methodology well within the capabilities of someone skilled in the art. Various prodrugs of carboxy are known in the art. For examples of such prodrug derivatives, see:

a) Design of Prodrugs, edited by H. Bundgaard, (Elsevier, 1985) and Methods in Enzymology. 42: 309-396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113-191 (1991);

c) H. Bundgaard, Advanced Drug Delivery Reviews, 8:1-38 (1992);

d) H. Bundgaard, et al., Journal of Pharmaceutical Sciences, 77:285 (1988); and e) N. Kakeya, et al., Chem Pharm Bull, 32:692 (1984).

The above documents a to e are herein incorporated by reference.

In vivo cleavable esters are just one type of prodrug of the parent molecule.

The compounds described herein preferably have activity as medicaments. In particular the compounds described herein are preferably highly potent agonists of PPARα. In addition the compounds described herein are also preferably agonists of PPARγ. The term agonists as used herein, includes partial agonists.

In the present specification the expression "pharmaceutically acceptable salts" is intended to define but is not limited to base salts such as the alkali metal salts, alkaline earth metal salts, ammonium salts, salts with basic amino acids, and salts with organic amines, for example tert-butylamine.

It will also be understood that certain compounds of the present invention may exist in solvated, for example hydrated, as well as unsolvated forms. It is to be understood that the present invention encompasses all such solvated forms. Certain compounds of the present invention may exist as tautomers. It is to be understood that the present invention encompasses all such tautomers.

The details of one or more embodiments of the invention are set forth in the accompanying drawings and the description below. Other features, objects, and advantages of the invention will be apparent from the description and from the claims.

DETAILED DESCRIPTION

Examples of the compounds of formula (I) include, but are not limited to those described below.

The present invention provides, for example, the S enantiomer of a compound of formula (II)

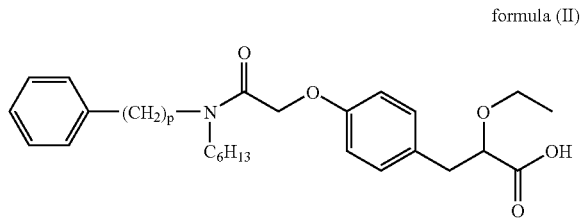

formula (II)

wherein p is 1 or 2 and pharmaceutcally acceptable salts, solvates, crystalline forms and prodrugs thereof.

The present invention provides, for example, the S enantiomer of a compound of formula(III)

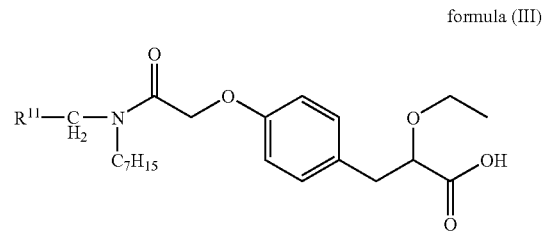

formula (III)

wherein $R^{11}$ represents 2,4-difluorophenyl or cyclohexyl as well as pharmaceutcally acceptable salts, solvates, crstalline forms and prodrugs thereof.

The present invention provides, for example, the S enantiomer of a compound of formula (IV)

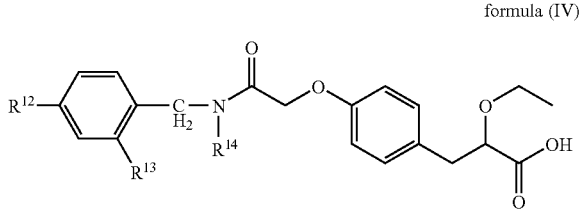

formula (IV)

wherein $R^{12}$ represents chloro, trifluoromethyl or trifluoromethoxy, $R^{13}$ represents H or fluoro and $R^{14}$ represents a $C_{2-4}$alkyl group as well as pharmaceutically acceptable salts, solvates and prodrugs thereof.

The present invention provides, for example, a compound of formula (V)

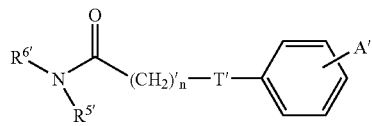

formula (V)

as well as optical isomers and racemates therof as well as pharmaceutically acceptable salts, prodrugs, solvates and crystalline forms thereof
wherein
A' is situated in the ortho, meta or para position and represents

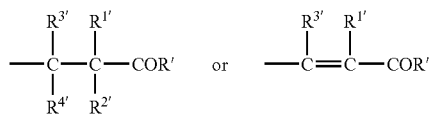

R' is hydrogen;
—$OR^{a'}$, wherein $R^{a'}$ represents hydrogen, alkyl, aryl or alkylaryl;
—$NR^{a'}R^{b'}$, wherein $R^{a'}$ and $R^{b'}$ are the same or different and $R^{a'}$ is as defined above and $R^{b'}$ represents hydrogen, alkyl, aryl, alkylaryl, cyano, —OH, —Oalkyl, —Oaryl, —Oalkylaryl, —$COR^{c'}$ or —$SO_2R^{d'}$, wherein $R^{c'}$ represents hydrogen, alkyl, aryl or alkylaryl and $R^{d'}$ represents alkyl, aryl or alkylaryl;
$R^{1'}$ is alkyl, aryl, alkenyl, alkynyl, or when A' is

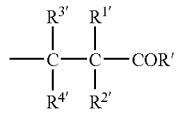

$R^{1'}$ can also be cyano;
—$OR^{e'}$, wherein $R^{e'}$ is alkyl, acyl, aryl or alkylaryl;
—O—$[CH_2]_{m'}$—$OR^{f'}$, wherein $R^{f'}$ represents hydrogen, alkyl, acyl, aryl or alkylaryl and m represents an integer 1-8;
—$OCONR^{a'}R^{c'}$, wherein $R^{a'}$ and $R^{c'}$ are as defined above;
—$SR^{d'}$, wherein $R^{d'}$ is as defined above;
—$SO_2NR^{a'}R^{f'}$, wherein $R^{f'}$ and $R^{a'}$ are as defined above;
—$SO_2OR^{a'}$, wherein $R^{a'}$ is as defined above;
—$COOR^{d'}$, wherein $R^{d'}$ is as defined above;
$R^{2'}$ is hydrogen, halogen, alkyl, aryl, or alkylaryl,
$R^{3'}$ and $R^{4'}$ are the same or different and each represents hydrogen, alkyl, aryl, or alkylaryl;
T' represents O, S or a single bond;
n' represents 1, 2, 3 or 4;
$R^{5'}$ and $R^{6'}$ are independently selected substituents, comprising C, H, N, O, S, Se, P or halogen atoms, which give compounds of the General Formula (V) a molecular weight<650.

In some embodiments, when A' is $CH_2CH(OC_2H_5)COOC_2H_5$ or $CH_2CH(OC_2H_5)COOH$; T' is O; n' is 1 and $R^{5'}$ represents a $C_{2-4}$alkyl group then $R^{6'}$ does not represent a group of formula

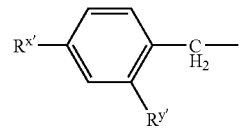

wherein $R^{x'}$ represents chloro, trifluoromethyl or trifluoromethoxy, $R^{y'}$ represents H or fluoro;
In some embodiments, when A' is $CH_2CH(OC_2H_5)COOC_2H_5$ or $CH_2CH(OC_2H_5)COOH$; T' is O; n' is 1 and $R^{5'}$ represents hexyl or heptyl then $R^{6'}$ does not represent a group of formula

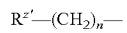

$R^{z'}$—$(CH_2)_n$— wherein $R^{z'}$ represents phenyl, 2,4-difluorophenyl or cyclohexyl, and n' is 1 or 2.
In some embodiments, the compound of formula (V) is not one of the following compounds:
(2S)-4-[2-[[2-[[(2,6-dichlorophenyl)methyl]thio]ethyl] amino]-2-oxoethoxy]-α-methoxy-benzenepropanoic acid;
(2S)-4-[2-[butyl(1-phenylethyl)amino]-2-oxoethoxy]-α-methoxy-benzenepropanoic acid;
(2S)-α-methoxy-4-[2-oxo-2-[[2-(3-pyridinyl)ethyl] amino]ethoxy]-benzenepropanoic acid;
(2S)-α-methyl-4-[2-oxo-2-[[2-(4-phenoxyphenyl)ethyl] amino]ethoxy]-α-phenoxy-benzenepropanoic acid;
(2S)-α-methoxy-4-[2-[(1-methyl-3-phenylpropyl) amino]-2-oxoethoxy]-benzenepropanoic acid;
(2S)-α-methoxy-4-[2-oxo-2-[[2-(4-phenoxyphenyl)ethyl] amino]ethoxy]-benzenepropanoic acid;
(2S)-α-methoxy-4-[2-oxo-2-[4-[4-(trifluoromethyl)phenyl]-1-piperazinyl]ethoxy]-benzenepropanoic acid;
(2S)-4-[2-[[2-(4-bromophenyl)ethyl]amino]-2-oxoethoxy]-α-methoxy-benzenepropanoic acid;
(2S)-4-[2-[4-[(4-chlorophenyl)phenylmethyl]-1-piperazinyl]-2-oxoethoxy]-α-methoxy-benzenepropanoic acid;
(2S)-4-[2-[[2-[ethyl(3-methylphenyl)amino]ethyl] amino]-2-oxoethoxy]-α-methoxy-benzenepropanoic acid;
α-methoxy-α-methyl-4-[2-oxo-2-[[2-(4-phenoxyphenyl) ethyl]amino]ethoxy]-benzenepropanoic acid;
(2S)-α-methoxy-4-[2-[(3-methylbutyl)amino]-2-oxoethoxy]-α-methoxy-benzenepropanoic acid;
(2S)-4-[2-[4-(diphenylmethyl)-1-piperazinyl]-2-oxoethoxy]-α-methoxy-benzenepropanoic acid;
(2S)-4-[2-(heptylamino)-2-oxoethoxy]-α-methoxy-α-methyl-benzenepropanoic acid;
4-[2-[4-(2-fluorophenyl)-1-piperazinyl]-2-oxoethoxy]-α-methoxy-, benzenepropanoic acid;

(2S)-4-[2-[4-(4-chlorobenzoyl)-1-piperidinyl]-2-oxoethoxy]-α-methoxy-, benzenepropanoic acid;
(2S)-4-[2-[ethyl[(3-methylphenyl)methyl]amino]-2-oxoethoxy]-α-methoxy-benzenepropanoic acid;
(2S)-α-methoxy-4-[2-oxo-2-[(4-phenoxyphenyl)amino]ethoxy]-benzenepropanoic acid;
(2S)-4-[2-[(1-methylhexyl)amino]-2-oxoethoxy]-benzenepropanoic acid;
(2S)-4-[2-[([1,1'-biphenyl]-4-ylmethyl)amino]-2-oxoethoxy]-α-methoxy-benzenepropanoic acid;
3-[2-[[cis-4-(1,1-dimethylethyl)cyclohexyl]amino]-2-oxoethoxy]-α-methoxy-benzenepropanoic acid;
(2S)-4-[2-[4-(3-chlorophenyl)-1-piperazinyl]-2-oxoethoxy]-α-methoxy-benzenepropanoic acid;
(2S)-α-methoxy-4-[2-[methyl[(1S)-1-phenylethyl]amino]-2-oxoethoxy]-benzenepropanoic acid;
(2S)-α-methoxy-4-[2-[4-(4-methylphenyl)-1-piperazinyl]-2-oxoethoxy]-benzenepropanoic acid;
(2S)-α-methoxy-4-[2-[[3-(methylphenylamino)propyl]amino]-2-oxoethoxy]-benzenepropanoic acid;
(2S)-4-[2-(cyclobutylamino)-2-oxoethoxy]-α-methoxy-benzenepropanoic acid;
(2S)-α-methyl-4-[2-oxo-2-[[2-(4-phenoxyphenyl)ethyl]amino]ethoxy]-α-[4-(trifluoromethoxy)phenoxy]-benzenepropanoic acid;
(2S)-4-[2-(heptylamino)-2-oxoethoxy]-α-methoxy-benzenepropanoic acid;
(2S)-4-[2-[4-(4-fluorophenyl)-1-piperazinyl]-2-oxoethoxy]-α-methoxy-benzenepropanoic acid;
(2S)-α-methoxy-4-[2-[[(1S)-1-(1-naphthalenyl)ethyl]amino]-2-oxoethoxy]-benzenepropanoic acid;
(2S)-α-methoxy-4-[2-oxo-2-[[(1R)-1-phenylethyl](phenylmethyl)amino]ethoxy]-benzenepropanoic acid;
(2S)-4-[2-[(3,3-diphenylpropyl)amino]-2-oxoethoxy]-α-methoxy-benzenepropanoic acid;
(2S)-4-[2-[[trans-4-(1,1-dimethylethyl)cyclohexyl]amino]-2-oxoethoxy]-α-methoxy-benzenepropanoic acid;
(2S)-α-methyl-4-[2-oxo-2-[[2-(4-phenoxyphenyl)ethyl]amino]ethoxy]-α-phenoxy-, ethyl ester-benzenepropanoic acid;
(2S)-4-[2-[(2,2,3,3,4,4,4-heptafluorobutyl)amino]-2-oxoethoxy]-α-methoxy-benzenepropanoic acid;
(2S)-4-[2-(3,4-dihydro-2(1H)-isoquinolinyl)-2-oxoethoxy]-α-methoxy-benzenepropanoic acid;
(2S)-3-[2-[[2-(4-ethylphenyl)ethyl]amino]-2-oxoethoxy]-α-methoxy-benzenepropanoic acid;
(2S)-α-methoxy-4-[2-[(1-naphthalenylmethyl)amino]-2-oxoethoxy]-benzenepropanoic acid;
(2S)-4-[2-[[(4-chlorophenyl)phenylmethyl]amino]-2-oxoethoxy]-α-methoxy-benzenepropanoic acid;
(2S)-α-methoxy-4-[2-oxo-2-[[2-(2-pyridinyl)ethyl]amino]ethoxy]-benzenepropanoic acid;
(2S)-α-methoxy-4-[2-oxo-2-[[(1S)-1-phenylethyl]amino]ethoxy]-benzenepropanoic acid;
(2S)-4-[2-(cyclopentylamino)-2-oxoethoxy]-α-methoxy-benzenepropanoic acid;
(2S)-4-[2-[4-[bis(4-fluorophenyl)methyl]-1-piperazinyl]-2-oxoethoxy]-α-methoxy-benzenepropanoic acid;
4-[2-[cyclohexyl[2-(4-ethylphenyl)ethyl]amino]-2-oxoethoxy]-α-ethoxy-benzenepropanoic acid;
(2S)-4-[2-[(1,3-benzodioxol-5-ylmethyl)amino]-2-oxoethoxy]-α-methoxy-benzenepropanoic acid;
D-Phenylalanine, N-[[4-[(2S)-2-carboxy-2-methoxyethyl]phenoxy]acetyl]-, α-methyl ester;
(2S)-4-[2-[4-[(4-fluorophenyl)methyl]-1-piperazinyl]-2-oxoethoxy]-α-methoxy-benzenepropanoic acid;
α-methoxy-3-[2-oxo-2-[(4-phenoxyphenyl)amino]ethoxy]-benzenepropanoic acid;
(2S)-α-methoxy-4-[2-[(1-methylbutyl)amino]-2-oxoethoxy]-benzenepropanoic acid;
(2S)-α-methoxy-4-[2-[methyl(1-naphthalenylmethyl)amino]-2-oxoethoxy]-benzenepropanoic acid;
(2S)-3-[2-[[trans-4-(1,1-dimethylethyl)cyclohexyl]amino]-2-oxoethoxy]-α-methoxy-benzenepropanoic acid;
(2S)-4-[2-[4-[(4-chlorophenyl)methyl]-1-piperazinyl]-2-oxoethoxy]-α-methoxy-benzenepropanoic acid;
(2S)-4-[2-[4-(4-fluorobenzoyl)-1-piperidinyl]-2-oxoethoxy]-α-methoxy-benzenepropanoic acid;
(2S)-4-[2-[ethyl[(2-fluorophenyl)methyl]amino]-2-oxoethoxy]-α-methoxy-benzenepropanoic acid;
(2S)-α-methoxy-4-[2-[[2-(4-methoxyphenoxy)ethyl]amino]-2-oxoethoxy]-benzenepropanoic acid;
(2S)-4-[2-[(1,3-dimethylbutyl)amino]-2-oxoethoxy]-α-methoxy-benzenepropanoic acid;
(2S)-α-(4-fluorophenoxy)-α-methyl-4-[2-oxo-2-[[2-(4-phenoxyphenyl)ethyl]amino]ethoxy]-benzenepropanoic acid;
(2S)-4-[2-[(3,3-dimethylbutyl)amino]-2-oxoethoxy]-α-methoxy-benzenepropanoic acid;
(2S)-4-[2-[4-(4-chlorophenyl)-3-methyl-1-piperazinyl]-2-oxoethoxy]-α-methoxy-benzenepropanoic acid;
(2S)-α-methoxy-4-[2-oxo-2-[[(1R)-1-phenylethyl]amino]ethoxy]-benzenepropanoic acid;
(2S)-4-[2-[4-(4-acetylphenyl)-1-piperazinyl]-2-oxoethoxy]-α-methoxy-benzenepropanoic acid;
(2S)-4-[2-[(3-ethoxy-3-oxopropyl)(phenylmethyl)amino]-2-oxoethoxy]-α-methoxy-benzenepropanoic acid;
(2S)-4-[2-[[cis-4-(1,1-dimethylethyl)cyclohexyl]amino]-2-oxoethoxy]-α-methoxy-benzenepropanoic acid;
(2S)-α-ethyl-4-[2-oxo-2-[[2-(4-phenoxyphenyl)ethyl]amino]ethoxy]-α-phenoxy-benzenepropanoic acid;
(2S)-4-[2-(hexylamino)-2-oxoethoxy]-α-methoxy-benzenepropanoic acid;
(2S)-α-methoxy-4-[2-oxo-2-[(2-phenylethyl)(phenylmethyl)amino]ethoxy]-benzenepropanoic acid;
or
(2S)-4-[2-[ethyl[2-(4-methoxyphenyl)-1-methylethyl]amino]-2-oxoethoxy]-α-methoxy-benzenepropanoic acid.

In another aspect, the compound of formula (V) is defined as follows:

A' is situated in the ortho, meta or para position and represents

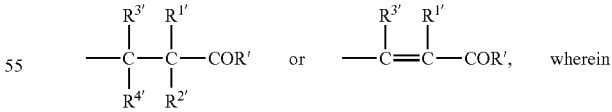

R' is hydrogen;
—OR$^{a'}$, wherein R$^{a'}$ represents hydrogen, alkyl, aryl or alkylaryl;
—NR$^{a'}$R$^{b'}$, wherein R$^{a'}$ and R$^{b'}$ are the same or different and R$^{a'}$ is as defined above and R$^{b'}$ represents hydrogen, alkyl, aryl, alkylaryl, cyano, —OH, —Oalkyl, —Oaryl, —Oalkylaryl, —COR$^{c'}$ or —SO$_2$R$^{d'}$, wherein R$^{c'}$ represents hydrogen, alkyl, aryl or alkylaryl and R$^{d'}$ represents alkyl, aryl or alkylaryl;

$R^{1'}$ is alkyl, aryl, alkenyl, alkynyl, or when A' is

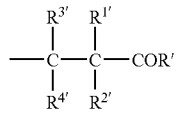

$R^{1'}$ can also be cyano;

—$OR^{e'}$, wherein $R^{e'}$ is alkyl, acyl, aryl or alkylaryl;
—O—$[CH_2]_{m'}$—$OR^{f'}$, wherein $R^{f'}$ represents hydrogen, alkyl, acyl, aryl or alkylaryl and m represents an integer 1-8;
—$OCONR^{a'}R^{c'}$, wherein $R^{a'}$ and $R^{c'}$ are as defined above;
—$SR^{d'}$, wherein $R^{d'}$ is as defined above;
—$SO_2NR^{a'}R^{f'}$, wherein $R^{f'}$ and $R^{a'}$ are as defined above;
—$SO_2OR^{a'}$, wherein $R^{a'}$ is as defined above;
—$COOR^{d'}$, wherein $R^{d'}$ is as defined above;
$R^{2'}$ is hydrogen, halogen, alkyl, aryl, or alkylaryl,
$R^{3'}$ and $R^{4'}$ are the same or different and each represents hydrogen, alkyl, aryl, or alkylaryl;
T' represents O, S or a single bond;
n' represents 1, 2, 3 or 4;
$R^{5'}$ and $R^{6'}$ are independently selected substituents, comprising C, H, N, O, S, Se, P or halogen atoms, which give compounds of the General Formula (V) a molecular weight<650.

In some embodiments, when A' is $CH_2CH(OC_2H_5)COOC_2H_5$ or $CH_2CH(OC_2H_5)COOH$; T' is O; n is 1 and $R^{5'}$ represents a $C_{2-4}$alkyl group then $R^{6'}$ does not represent a group of formula

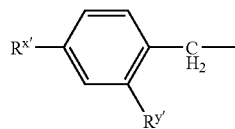

wherein $R^{x'}$ represents chloro, trifluoromethyl or trifluoromethoxy, $R^{y'}$ represents H or fluoro.

In some embodiments, when A' is $CH_2CH(OC_2H_5)COOC_2H_5$ or $CH_2CH(OC_2H_5)COOH$; T' is O; n' is 1 and $R^{5'}$ represents hexyl or heptyl then $R^{6'}$ does not represent a group of formula

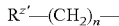

wherein $R^{z'}$ represents phenyl, 2,4-difluorophenyl or cyclohexyl, and n' is 1 or 2.

In some embodiments, the compound of formula (V) is not one of the following compounds:

(2S)-4-[2-[[2-[[(2,6-dichlorophenyl)methyl]thio]ethyl]amino]-2-oxoethoxy]-α-methoxy-benzenepropanoic acid;
(2S)-4-[2-[butyl(1-phenylethyl)amino]-2-oxoethoxy]-α-methoxy-benzenepropanoic acid;
(2S)-α-methoxy-4-[2-oxo-2-[[2-(3-pyridinyl)ethyl]amino]ethoxy]-benzenepropanoic acid;
(2S)-α-methyl-4-[2-oxo-2-[[2-(4-phenoxyphenyl)ethyl]amino]ethoxy]-α-phenoxy-benzenepropanoic acid;
(2S)-α-methoxy-4-[2-[(1-methyl-3-phenylpropyl)amino]-2-oxoethoxy]-benzenepropanoic acid;
(2S)-α-methoxy-4-[2-oxo-2-[[2-(4-phenoxyphenyl)ethyl]amino]ethoxy]-benzenepropanoic acid;
(2S)-α-methoxy-4-[2-oxo-2-[4-[4-(trifluoromethyl)phenyl]-1-piperazinyl]ethoxy]-benzenepropanoic acid;
(2S)-4-[2-[[2-(4-bromophenyl)ethyl]amino]-2-oxoethoxy]-α-methoxy-benzenepropanoic acid;
(2S)-4-[2-[4-[(4-chlorophenyl)phenylmethyl]-1-piperazinyl]-2-oxoethoxy]-α-methoxy-benzenepropanoic acid;
(2S)-4-[2-[[2-[ethyl(3-methylphenyl)amino]ethyl]amino]-2-oxoethoxy]-α-methoxy-benzenepropanoic acid;
α-methoxy-α-methyl-4-[2-oxo-2-[[2-(4-phenoxyphenyl)ethyl]amino]ethoxy]-benzenepropanoic acid;
(2S)-α-methoxy-4-[2-[(3-methylbutyl)amino]-2-oxoethoxy]-benzenepropanoic acid;
(2S)-4-[2-[4-(diphenylmethyl)-1-piperazinyl]-2-oxoethoxy]-α-methoxy-benzenepropanoic acid;
(2S)-4-[2-(heptylamino)-2-oxoethoxy]-α-methoxy-α-methyl-benzenepropanoic acid;
4-[2-[4-(2-fluorophenyl)-1-piperazinyl]-2-oxoethoxy]-α-methoxy-, benzenepropanoic acid;
(2S)-4-[2-[4-(4-chlorobenzoyl)-1-piperidinyl]-2-oxoethoxy]-α-methoxy-, benzenepropanoic acid;
(2S)-4-[2-[ethyl[(3-methylphenyl)methyl]amino]-2-oxoethoxy]-α-methoxy-benzenepropanoic acid;
(2S)-α-methoxy-4-[2-oxo-2-[(4-phenoxyphenyl)amino]ethoxy]-benzenepropanoic acid;
(2S)-α-methoxy-4-[2-[(1-methylhexyl)amino]-2-oxoethoxy]-benzenepropanoic acid;
(2S)-4-[2-[([1,1'-biphenyl]-4-ylmethyl)amino]-2-oxoethoxy]-α-methoxy-benzenepropanoic acid;
3-[2-[[cis-4-(1,1-dimethylethyl)cyclohexyl]amino]-2-oxoethoxy]-α-methoxy-benzenepropanoic acid;
(2S)-4-[2-[4-(3-chlorophenyl)-1-piperazinyl]-2-oxoethoxy]-α-methoxy-benzenepropanoic acid;
(2S)-α-methoxy-4-[2-[methyl[(1S)-1-phenylethyl]amino]-2-oxoethoxy]-benzenepropanoic acid;
(2S)-α-methoxy-4-[2-[4-(4-methylphenyl)-1-piperazinyl]-2-oxoethoxy]-benzenepropanoic acid;
(2S)-α-methoxy-4-[2-[[3-(methylphenylamino)propyl]amino]-2-oxoethoxy]-benzenepropanoic acid;
(2S)-4-[2-(cyclobutylamino)-2-oxoethoxy]-α-methoxy-benzenepropanoic acid;
(2S)-α-methyl-4-[2-oxo-2-[[2-(4-phenoxyphenyl)ethyl]amino]ethoxy]-α-[4-(trifluoromethoxy)phenoxy]-benzenepropanoic acid;
(2S)-4-[2-(heptylamino)-2-oxoethoxy]-α-methoxy-benzenepropanoic acid;
(2S)-4-[2-[4-(4-fluorophenyl)-1-piperazinyl]-2-oxoethoxy]-α-methoxy-benzenepropanoic acid;
(2S)-α-methoxy-4-[2-[[(1S)-1-(1-naphthalenyl)ethyl]amino]-2-oxoethoxy]-benzenepropanoic acid;
(2S)-α-methoxy-4-[2-oxo-2-[[(1R)-1-phenylethyl](phenylmethyl)amino]ethoxy]-benzenepropanoic acid;
(2S)-4-[2-[(3,3-diphenylpropyl)amino]-2-oxoethoxy]-α-methoxy-benzenepropanoic acid;
(2S)-4-[2-[[trans-4-(1,1-dimethylethyl)cyclohexyl]amino]-2-oxoethoxy]-α-methoxy-benzenepropanoic acid;
(2S)-α-methyl-4-[2-oxo-2-[[2-(4-phenoxyphenyl)ethyl]amino]ethoxy]-α-phenoxy-, ethyl ester-benzenepropanoic acid;
(2S)-4-[2-[(2,2,3,3,4,4,4-heptafluorobutyl)amino]-2-oxoethoxy]-α-methoxy-benzenepropanoic acid;
(2S)-4-[2-(3,4-dihydro-2(1H)-isoquinolinyl)-2-oxoethoxy]-α-methoxy-benzenepropanoic acid;
(2S)-3-[2-[[2-(4-ethylphenyl)ethyl]amino]-2-oxoethoxy]-α-methoxy-benzenepropanoic acid;
(2S)-α-methoxy-4-[2-[(1-naphthalenylmethyl)amino]-2-oxoethoxy]-benzenepropanoic acid;

(2S)-4-[2-[[(4-chlorophenyl)phenylmethyl]amino]-2-oxoethoxy]-α-methoxy-benzenepropanoic acid;
(2S)-α-methoxy-4-[2-oxo-2-[[2-(2-pyridinyl)ethyl]amino]ethoxy]-benzenepropanoic acid;
(2S)-α-methoxy-4-[2-oxo-2-[[(1S)-1-phenylethyl]amino]ethoxy]-benzenepropanoic acid;
(2S)-4-[2-(cyclopentylamino)-2-oxoethoxy]-α-methoxy-benzenepropanoic acid;
(2S)-4-[2-[4-[bis(4-fluorophenyl)methyl]-1-piperazinyl]-2-oxoethoxy]-α-methoxy-benzenepropanoic acid;
4-[2-[cyclohexyl[2-(4-ethylphenyl)ethyl]amino]-2-oxoethoxy]-α-ethoxy-benzenepropanoic acid;
(2S)-4-[2-[(1,3-benzodioxol-5-ylmethyl)amino]-2-oxoethoxy]-α-methoxy-benzenepropanoic acid;
D-Phenylalanine, N-[[4-[(2S)-2-carboxy-2-methoxyethyl]phenoxy]acetyl]-, α-methyl ester;
(2S)-4-[2-[4-[(4-fluorophenyl)methyl]-1-piperazinyl]-2-oxoethoxy]-α-methoxy-benzenepropanoic acid;
α-methoxy-3-[2-oxo-2-[(4-phenoxyphenyl)amino]ethoxy]-benzenepropanoic acid;
(2S)-α-methoxy-4-[2-[(1-methylbutyl)amino]-2-oxoethoxy]-benzenepropanoic acid;
(2S)-α-methoxy-4-[2-[methyl(1-naphthalenylmethyl)amino]-2-oxoethoxy]-benzenepropanoic acid;
(2S)-3-[2-[[trans-4-(1,1-dimethylethyl)cyclohexyl]amino]-2-oxoethoxy]-α-methoxy-benzenepropanoic acid;
(2S)-4-[2-[4-[(4-chlorophenyl)methyl]-1-piperazinyl]-2-oxoethoxy]-α-methoxy-benzenepropanoic acid;
(2S)-4-[2-[4-(4-fluorobenzoyl)-1-piperidinyl]-2-oxoethoxy]-α-methoxy-benzenepropanoic acid;
(2S)-4-[2-[ethyl[(2-fluorophenyl)methyl]amino]-2-oxoethoxy]-α-methoxy-benzenepropanoic acid;
(2S)-α-methoxy-4-[2-[[2-(4-methoxyphenoxy)ethyl]amino]-2-oxoethoxy]-benzenepropanoic acid;
(2S)-4-[2-[(1,3-dimethylbutyl)amino]-2-oxoethoxy]-α-methoxy-benzenepropanoic acid;
(2S)-α-(4-fluorophenoxy)-α-methyl-4-[2-oxo-2-[[2-(4-phenoxyphenyl)ethyl]amino]ethoxy]-benzenepropanoic acid;
(2S)-4-[2-[(3,3-dimethylbutyl)amino]-2-oxoethoxy]-α-methoxy-benzenepropanoic acid;
(2S)-4-[2-[4-(4-chlorophenyl)-3-methyl-1-piperazinyl]-2-oxoethoxy]-α-methoxy-benzenepropanoic acid;
(2S)-α-methoxy-4-[2-oxo-2-[[(1R)-1-phenylethyl]amino]ethoxy]-benzenepropanoic acid;
(2S)-4-[2-[4-(4-acetylphenyl)-1-piperazinyl]-2-oxoethoxy]-α-methoxy-benzenepropanoic acid;
(2S)-4-[2-[(3-ethoxy-3-oxopropyl)(phenylmethyl)amino]-2-oxoethoxy]-α-methoxy-benzenepropanoic acid;
(2S)-4-[2-[[cis-4-(1,1-dimethylethyl)cyclohexyl]amino]-2-oxoethoxy]-α-methoxy-benzenepropanoic acid;
(2S)-α-ethyl-4-[2-oxo-2-[[2-(4-phenoxyphenyl)ethyl]amino]ethoxy]-α-phenoxy-benzenepropanoic acid;
(2S)-4-[2-(hexylamino)-2-oxoethoxy]-α-methoxy-benzenepropanoic acid;
(2S)-α-methoxy-4-[2-oxo-2-[(2-phenylethyl)(phenylmethyl)amino]ethoxy]-benzenepropanoic acid;
(2S)-4-[2-[ethyl[2-(4-methoxyphenyl)-1-methylethyl]amino]-2-oxoethoxy]-α-methoxy-benzenepropanoic acid;
[[4-[2-oxo-2-[[phenyl[2-(1-piperidinyl)phenyl]methyl]amino]ethyl]phenyl]methyl]-, diethyl ester-propanedioic acid;
4-[2-(heptylamino)-2-oxoethyl]-α,α-dimethyl-, ethyl ester-benzenepropanoic acid;
2-[[4-(2-amino-2-oxoethoxy)phenyl]methylene]-3-oxo-, methyl ester-butanoic acid;
4-[2-[methyl(2-phenylethyl)amino]-2-oxoethyl]-α-phenyl-,ethyl ester-benzenepropanoic acid;
4-[2-(heptylamino)-2-oxoethyl]-α,α-dimethyl-, ethyl ester-benzenepropanoic acid;
4-[2-[[2-[[(1,1-dimethylethoxy)carbonyl]methylamino]-4-hydroxyphenyl]amino]-2-oxoethoxy]-α-(methylthio)-, ethyl ester-benzenepropanoic acid;
[[4-[2-oxo-2-[[phenyl[2-(1-piperidinyl)phenyl]methyl]aminoethyl]phenyl]methyl]-propanedioic acid;
N-[3-[4-[2-[methyl(2-phenylethyl)amino]-2-oxoethyl]phenyl]-1-oxo-2-phenylpropyl]-, methyl ester-glycine;
4-[2-[methyl(2-phenylethyl)amino]-2-oxoethyl]-α-phenyl-benzenepropanoic acid;
N-[3-[4-[2-[methyl(2-phenylethyl)amino]-2-oxoethyl]phenyl]-1-oxo-2-phenylpropyl]-glycine;
or
4-[3-[methyl(2-phenylethyl)amino]-3-oxopropyl]-α-phenyl-benzenpropanoic acid.

In some preferred embodiments, $R^{5'}$ and $R^{6'}$ are independently selected substituents, comprising C, H, N, O, S or halogen atoms, which give compounds of the General Formula I a molecular weight<650. Alternatively, $R^{5'}$ and $R^{6'}$ are independently selected substituents, comprising C, N, O, S, Se, P or halogen atoms. According to one aspect of the invention, when either of $R^{5'}$ and $R^{6'}$ is hydrogen, the other is not an alkyl.

In some preferred embodiments, $R^{5'}$ and $R^{6'}$ independently represent hydrogen, $C_{1-13}$alkyl, $C_{2-10}$alkenyl or $C_{2-10}$alkynyl each of which is optionally substituted by one or more of the following which may be the same or different: $C_{3-8}$cycloalkyl, $C_{3-8}$cycloalkenyl, aryl, heterocyclyl, heteroaryl, $C_{1-8}$alkoxy (optionally substituted by one or more fluoro), $C_{3-8}$cycloalkoxy, $C_{3-8}$cycloalkenyloxy, aryloxy, heterocyclyloxy, heteroaryloxy, $C_{3-8}$cycloalkyl $C_{1-8}$alkoxy, aryl $C_{1-8}$alkoxy, heterocyclyl $C_{1-8}$ alkoxy or heteroaryl $C_{1-8}$ alkoxy, fluorine or hydroxy and wherein each of these substituents may optionally be substituted on carbon with one or more substituents which may be the same or different and selected from $C_{1-8}$alkyl, $C_{3-8}$cycloalkyl (optionally substituted by $C_{1-8}$alkyl, $C_{1-8}$alkoxy (optionally substituted by one or more fluoro), halogen, hydroxy, nitro or cyano), aryl (optionally substituted by $C_{1-8}$alkyl, $C_{1-8}$alkoxy (optionally substituted by one or more fluoro), halogen, hydroxy, nitro or cyano), heterocyclyl (optionally substituted by $C_{1-6}$alkyl on any nitrogen), heteroaryl (optionally substituted by $C_{1-8}$alkyl, $C_{1-8}$alkoxy (optionally substituted by one or more fluoro), halogen, hydroxy, nitro or cyano), $C_{1-8}$alkoxy (optionally substituted by one or more fluoro), $C_{3-8}$cycloalkoxy, $C_{3-8}$ cycloalkyl $C_{1-8}$alkoxy, aryloxy (optionally substituted by $C_{1-8}$alkyl, $C_{1-8}$alkoxy (optionally substituted by one or more fluoro), halogen, hydroxy, nitro or cyano), aryl $C_{1-8}$alkoxy (wherein the aryl part is optionally substituted by $C_{1-8}$alkyl, $C_{1-8}$alkoxy (optionally substituted by one or more fluoro), halogen, hydroxy, nitro or cyano), halogen, amino, nitro, hydroxy, methylsulfonyl, methylsulfonyloxy, cyano or methylenedioxy, or $R^{5'}$ and $R^{6'}$ independently represent $C_3$-$C_8$ cycloalkyl; $C_3$-$C_8$ cycloalkenyl; aryl; heterocyclyl; or heteroaryl; wherein each of these groups is optionally substituted by one or more of the following: $C_{1-8}$alkyl, $C_{1-8}$alkoxy (optionally substituted by one or more fluoro), halogen, hydroxy, nitro or cyano, aryl (optionally substituted by $C_{1-8}$alkyl, $C_{1-8}$alkoxy (optionally substituted by one or more fluoro), halogen, hydroxy, nitro or cyano;

or $R^{5'}$ and $R^{6'}$ together with the nitrogen atom to which they are attached form a single or a fused heterocyclic system.

In some preferred embodiments, A' is $CH_2CH(OR^{r'})CO-OR^{m'}$ wherein $R^{r'}$ represents $C_{1-4}$alkyl and wherein $R^{m'}$ represents H or $C_{1-4}$alkyl.

A preferred group of compounds is represented by formula (Va)

formula (Va)

as well as optical isomers and racemates therof as well as pharmaceutically acceptable salts, prodrugs, solvates and crystalline forms thereof
wherein;
T' represents O or a single bond;
n'=1 or 2;
$R^{5'}$ and $R^{6'}$ are independently selected $C_{1-10}$alkyl (optionally substituted by one or more $C_{1-4}$alkoxy); $C_{5-7}$cycloalkyl $C_{1-4}$alkyl (optionally substituted cyano); benzyl or phenethyl (each of which is optionally substituted by one or more of the following: halo; $C_{1-4}$alkyl; $C_{1-4}$alkoxy; trifluoromethyl; trifluoromethoxy; methylenedioxy; phenyl; benzyloxy; methanesulfonyloxy); indolylmethyl; or thienylmethyl.

In preferred groups of compounds of formula (V) and formula (Va), $R^{5'}$ represents $C_{1-10}$alkyl (optionally substituted by one or more $C_{1-4}$alkoxy) and $R^{6'}$ represents benzyl optionally substituted one or more of the following: halo; $C_{1-4}$alkyl; $C_{1-4}$alkoxy; trifluoromethyl; trifluoromethoxy; methylenedioxy; phenyl; benzyloxy or methanesulfonyloxy.

Alternatively n' represents 2, 3 or 4.

In other preferred groups of compounds of formula (V) and (Va) $R^{5'}$ and $R^{6'}$ independently represent benzyl optionally substituted one or more of the following: halo; $C_{1-4}$alkyl; $C_{1-4}$alkoxy; trifluoromethyl; trifluoromethoxy; methylenedioxy; phenyl; benzyloxy or methanesulfonyloxy.

$R^{3'}$ and $R^{4'}$ may be the same or different and each represents alkyl, aryl or alkylaryl.

Alternatively $R^{3'}$ and $R^{4'}$ are hydrogen.

In one aspect of the invention $R^{2'}$ is hydrogen or fluorine.

A compound of formula (VI):

formula (VI)

wherein $R^{5'}$, $R^{6'}$ and n' is as defined in any of the preceding claims and Z' is a leaving group, such as a halide, $OSO_2CH_3$, OTosyl, ONosyl, $OSO_2CF_3$, OC(O)OR, OP(O)(OR)$_2$ or $OSO_2OR$, particularly chloro or bromo. Formula (VI) is useful as an intermediate in the process of manufacturing formula (V).

Examples of specific compounds include the following:
(2S)-3-(4-{2-[Benzyl(hexyl)amino]-2-oxoethoxy}phenyl)-2-ethoxypropanoic acid;
(2S)-2-Ethoxy-3-(4-{2-[hexyl(2-phenylethyl)amino]-2-oxoethoxy}phenyl)propanoic acid;
(2S)-3-[4-(2-{Butyl[2-fluoro-4-(trifluoromethyl)benzyl]amino}-2-oxoethoxy)phenyl]-2-ethoxy propanoic acid;
(2S)-3-(4-{2-[(4-Chlorobenzyl)(ethyl)amino]-2-oxoethoxy}phenyl)-2-ethoxypropanoic acid;
(2S)-2-Ethoxy-3-[4-(2-{ethyl[4-(trifluoromethoxy)benzyl]amino}-2-oxoethoxy)phenyl]-propanoic acid;
(2S)-2-Ethoxy-3-[4-(2-{ethyl[4-(trifluoromethyl)benzyl]amino}-2-oxoethoxy)phenyl]propanoic acid;
(2S)-3-[4-(2-{Butyl[4-(trifluoromethyl)benzyl]amino}-2-oxoethoxy)phenyl]-2-ethoxypropanoic acid;
(2S)-3-{2-[(Cyclohexylmethyl)(heptyl)amino]-2-oxoethoxy}phenyl)-2-ethoxypropanoic acid;
(2S)-3-(4-{2-[(2,4-Difluorobenzyl)(heptyl) amino]-2-oxoethoxy}phenyl)-2-ethoxypropanoic acid;
(2S)-3-(4-{2-[(2,4-Difluorobenzyl)(octyl)amino]-2-oxoethoxy}phenyl)-2-ethoxypropanoic acid;
(2S)-3-(4-{2-[(2,4-Difluorobenzyl)(nonyl)amino]-2-oxoethoxy}phenyl)-2-ethoxypropanoic acid;
(2S)-3-(4-{2-[(2,4-Difluorobenzyl)(4-ethylbenzyl) amino]-2-oxoethoxy}phenyl)-2-ethoxypropanoic acid;
(2S)-3-(4-{2-[Benzyl(methyl)amino]-2-oxoethoxy}phenyl)-2-ethoxypropanoic acid;
(2S)-2-Ethoxy-3-[4-(2-{heptyl[(1-methylindol-2-yl)methyl]amino}-2-oxoethoxy)phenyl]propanoic acid;
(2S)-3-(4-{2-[(2,3-Dimethoxybenzyl)(heptyl)amino]-2-oxoethoxy}phenyl)-2-ethoxypropanoic acid;
(2S)-3-(4-{2-[Butyl(2,3-dimethoxybenzyl)amino]-2-oxoethoxy}phenyl)-2-ethoxypropanoic acid;
(2S)-3-(4-{2-[(4-Chlorobenzyl)(4-isopropylbenzyl) amino]-2-oxoethoxy}phenyl)-2-ethoxypropanoic acid;
(2S)-3-(4-{2-[(Cyclohexylmethyl)(2,4-difluorobenzyl) amino]-2-oxoethoxy}phenyl)-2-ethoxypropanoic acid;
(2S)-2-Ethoxy-3-(4-{2-[ethyl(2-fluorobenzyl)amino]-2-oxoethoxy}phenyl)propanoic acid;
(2S)-3-(4-{2-[[4-(benzyloxy)benzyl](butyl)amino]-2-oxoethoxy}phenyl)-2-ethoxypropanoic acid;
(2S)-3-(4-{2-[bis(4-Chlorobenzyl)amino]-2-oxoethoxy}phenyl)-2-ethoxypropanoic acid;
(2S)-3-(4-{2-[(4-tert-Butylbenzyl)(4-chlorobenzyl) amino]-2-oxoethoxy}phenyl)-2-ethoxypropanoic acid;
(2S)-3-[4-(2-{(4-Chlorobenzyl)[4-(trifluoromethyl)benzyl]amino}-2-oxoethoxy)phenyl]-2-ethoxypropanoic acid;
(2S)-3-[4-(2-{bis[4-(Trifluoromethyl)benzyl]amino}-2-oxoethoxy)phenyl]-2-ethoxypropanoic acid;
(2S)-3-(4-{2-[Benzyl(ethyl)amino]-2-oxoethoxy}phenyl)-2-ethoxypropanoic acid;
(2S)-3-(4-{2-[(4-tert-Butylbenzyl)(ethyl)amino]-2-oxoethoxy}phenyl)-2-ethoxypropanoic acid;
(2S)-3-(4-{2-[benzyl(4-isopropylbenzyl)amino]-2-oxoethoxy}phenyl)-2-ethoxypropanoic acid;
(2S)-2-ethoxy-3-(4-{2-[(3-ethoxypropyl)(4-isopropylbenzyl)amino]-2-oxoethoxy}phenyl)propanoic acid;
(2S)-3-(4-{2-[butyl(4-isopropylbenzyl)amino]-2-oxoethoxy}phenyl)-2-ethoxypropanoic acid;
(2S)-3-(4-{2-[(2-chlorobenzyl)(heptyl)amino]-2-oxoethoxy}phenyl)-2-ethoxypropanoic acid;
(2S)-2-ethoxy-3-(4-{2-[heptyl(4-isopropylbenzyl) amino]-2-oxoethoxy}phenyl)propanoic acid;
(2S)-3-(4-{2-[[(4-cyanocyclohexyl)methyl](4-isopropylbenzyl)amino]-2-oxoethoxy}phenyl)-2-ethoxypropanoic acid;

(2S)-2-ethoxy-3-(4-{2-[(4-isopropylbenzyl)(2-methoxybenzyl)amino]-2-oxoethoxy}phenyl)propanoic acid;

(2S)-3-(4-{2-[(2-chlorobenzyl)(4-chlorobenzyl)amino]-2-oxoethoxy}phenyl)-2-ethoxypropanoic acid;

(2S)-3-(4-{2-[(4-chlorobenzyl)(2,3-dimethoxybenzyl)amino]-2-oxoethoxy}phenyl)-2-ethoxypropanoic acid;

(2S)-3-(4-{2-[(1,3-benzodioxol-5-ylmethyl)(4-ethoxybenzyl)amino]-2-oxoethoxy}phenyl)-2-ethoxypropanoic acid;

(2S)-3-(4-{2-[(1,3-benzodioxol-5-ylmethyl)(3-bromobenzyl)amino]-2-oxoethoxy}phenyl)-2-ethoxypropanoic acid;

(2S)-3-[4-(2-{(1,3-benzodioxol-5-ylmethyl)[3-(trifluoromethyl)benzyl]amino}-2-oxoethoxy)phenyl]-2-ethoxypropanoic acid;

(2S)-3-(4-{2-[(3,5-dimethoxybenzyl)(4-ethoxybenzyl)amino]-2-oxoethoxy}phenyl)-2-ethoxypropanoic acid;

(2S)-3-(4-{2-[(3-chloro-4-fluorobenzyl)(4-ethoxybenzyl)amino]-2-oxoethoxy}phenyl)-2-ethoxypropanoic acid;

(2S)-2-ethoxy-3-(4-{2-[(4-ethoxybenzyl)(2-thienylmethyl)amino]-2-oxoethoxy}phenyl)propanoic acid;

(2S)-3-(4-{2-[benzyl(isopropyl)amino]-2-oxoethoxy}phenyl)-2-ethoxypropanoic acid;

(2S)-3-{4-[2-(dibenzylamino)-2-oxoethoxy]phenyl}-2-ethoxypropanoic acid;

(2S)-3-(4-{2-[bis(2-methoxyethyl)amino]-2-oxoethoxy}phenyl)-2-ethoxypropanoic acid;

(2S)-2-ethoxy-3-[4-(2-{heptyl[4-(trifluoromethyl)benzyl]amino}-2-oxoethoxy)phenyl]propanoic acid;

(2S)-2-ethoxy-3-[4-(2-{heptyl[4-(trifluoromethoxy)benzyl]amino}-2-oxoethoxy)phenyl]propanoic acid;

(2S)-2-ethoxy-3-(4-{2-[(4-ethylbenzyl)(heptyl)amino]-2-oxoethoxy}phenyl)propanoic acid;

(2S)-3-(4-{2-[(4-tert-butylbenzyl)(heptyl)amino]-2-oxoethoxy}phenyl)-2-ethoxypropanoic acid;

(2S)-2-ethoxy-3-(4-{2-[heptyl(4-isobutylbenzyl)amino]-2-oxoethoxy}phenyl)propanoic acid;

(2S)-3-(4-{2-[benzyl(heptyl)amino]-2-oxoethoxy}phenyl)-2-ethoxypropanoic acid;

(2S)-2-ethoxy-3-(4-{2-[(4-fluorobenzyl)(heptyl)amino]-2-oxoethoxy}phenyl)propanoic acid;

(2S)-3-(4-{2-[(4-chlorobenzyl)(heptyl)amino]-2-oxoethoxy}phenyl)-2-ethoxypropanoic acid;

(2S)-3-(4-{2-[(4-bromobenzyl)(heptyl)amino]-2-oxoethoxy}phenyl)-2-ethoxypropanoic acid;

(2S)-3-(4-{2-[butyl(4-ethylbenzyl)amino]-2-oxoethoxy}phenyl)-2-ethoxypropanoic acid;

(2S)-3-(4-{2-[butyl(4-tert-butylbenzyl)amino]-2-oxoethoxy}phenyl)-2-ethoxypropanoic acid;

(2S)-3-(4-{2-[butyl(4-isobutylbenzyl)amino]-2-oxoethoxy}phenyl)-2-ethoxypropanoic acid;

(2S)-3-(4-{2-[benzyl(butyl)amino]-2-oxoethoxy}phenyl)-2-ethoxypropanoic acid;

(2S)-3-(4-{2-[butyl(4-fluorobenzyl)amino]-2-oxoethoxy}phenyl)-2-ethoxypropanoic acid;

(2S)-3-(4-{2-[(4-bromobenzyl)(butyl)amino]-2-oxoethoxy}phenyl)-2-ethoxypropanoic acid;

(2S)-3-(4-{2-[butyl(2,4-difluorobenzyl)amino]-2-oxoethoxy}phenyl)-2-ethoxypropanoic acid;

(2S)-3-[4-(2-{(4-chlorobenzyl)[4-(trifluoromethoxy)benzyl]amino}-2-oxoethoxy)phenyl]-2-ethoxypropanoic acid;

(2S)-3-(4-{2-[(4-chlorobenzyl)(4-ethylbenzyl)amino]-2-oxoethoxy}phenyl)-2-ethoxypropanoic acid;

(2S)-3-(4-{2-[(4-chlorobenzyl)(4-isobutylbenzyl)amino]-2-oxoethoxy}phenyl)-2-ethoxypropanoic acid;

(2S)-3-(4-{2-[benzyl(4-chlorobenzyl)amino]-2-oxoethoxy}phenyl)-2-ethoxypropanoic acid;

(2S)-3-(4-{2-[(4-chlorobenzyl)(4-fluorobenzyl)amino]-2-oxoethoxy}phenyl)-2-ethoxypropanoic acid;

(2S)-3-(4-{2-[(4-bromobenzyl)(4-chlorobenzyl)amino]-2-oxoethoxy}phenyl)-2-ethoxypropanoic acid;

(2S)-3-(4-{2-[(4-chlorobenzyl)(2,4-difluorobenzyl)amino]-2-oxoethoxy}phenyl)-2-ethoxypropanoic acid;

(2S)-2-ethoxy-3-[4-(2-{(4-methylbenzyl)[4-(trifluoromethyl)benzyl]amino}-2-oxoethoxy)phenyl]propanoic acid;

(2S)-2-ethoxy-3-[4-(2-{(4-methylbenzyl)[4-(trifluoromethoxy)benzyl]amino}-2-oxoethoxy)phenyl]propanoic acid;

(2S)-2-ethoxy-3-(4-{2-[(4-ethylbenzyl)(4-methylbenzyl)amino]-2-oxoethoxy}phenyl)propanoic acid;

(2S)-3-(4-{2-[(4-tert-butylbenzyl)(4-methylbenzyl)amino]-2-oxoethoxy}phenyl)-2-ethoxypropanoic acid;

(2S)-2-ethoxy-3-(4-{2-[(4-isobutylbenzyl)(4-methylbenzyl)amino]-2-oxoethoxy}phenyl)propanoic acid;

(2S)-3-(4-{2-[benzyl(4-methylbenzyl)amino]-2-oxoethoxy}phenyl)-2-ethoxypropanoic acid;

(2S)-2-ethoxy-3-(4-{2-[(4-fluorobenzyl)(4-methylbenzyl)amino]-2-oxoethoxy}phenyl)propanoic acid;

(2S)-3-(4-{2-[(4-chlorobenzyl)(4-methylbenzyl)amino]-2-oxoethoxy}phenyl)-2-ethoxypropanoic acid;

(2S)-3-(4-{2-[(4-bromobenzyl)(4-methylbenzyl)amino]-2-oxoethoxy}phenyl)-2-ethoxypropanoic acid; and (2S)-3-(4-{2-[(2,4-difluorobenzyl)(4-methylbenzyl)amino]-2-oxoethoxy}phenyl)-2-ethoxypropanoic acid;

and pharmaceutically acceptable salts, solvates, and crystalline forms thereof.

Examples of salts of the present invention include the following:

(2S)-3-[4-(2-{Butyl[2-fluoro-4-(trifluoromethyl)benzyl]amino}-2-oxoethoxy)phenyl]-2-ethoxy propanoic acid tert-butylammonium salt;

(2S)-3-(4-{2-[(4-Chlorobenzyl)(ethyl)amino]-2-oxoethoxy}phenyl)-2-ethoxypropanoic acid tert-butylammonium salt;

(2S)-2-Ethoxy-3-[4-(2-{ethyl[4-(trifluoromethoxy)benzyl]amino}-2-oxoethoxy)phenyl]-propanoic acid tert-butylammonium salt;

(2S)-2-Ethoxy-3-[4-(2-{ethyl[4-(trifluoromethyl)benzyl]amino}-2-oxoethoxy)phenyl]propanoic acid tert-butylammonium salt; and (2S)-3-[4-(2-{Butyl[4-(trifluoromethyl)benzyl]amino}-2-oxoethoxy)phenyl]-2-ethoxypropanoic acid tert-butylammonium salt.

It should be understood that each of the above compounds individually and also any combination of these compounds for example two, three, four or all of the above compounds forms part of the present invention.

These salts may be prepared by reacting an acid with tert-butylamine (for example around a molar equivalent with respect to the acid) in a solvent for example an ether e.g. diisopropyl ether or tert-butylmethyl ether or an ester e.g. tert-butyl acetate or mixtures thereof or from a mixture of one of these solvents and an anti-solvent for example a hydrocarbon e.g. isooctane and isolating the salt by methods known to those skilled in the art for example by filtration.

Methods of Preparation:

The compounds of the invention may be prepared as outlined below. However, the invention is not limited to these methods, the compounds may also be prepared as described for structurally related compounds in the prior art. The reactions can be carried out according to standard procedures or as described in the experimental section.

Compounds of formula (II) may be prepared by reacting the S-enantiomer of a compound of formula (X)

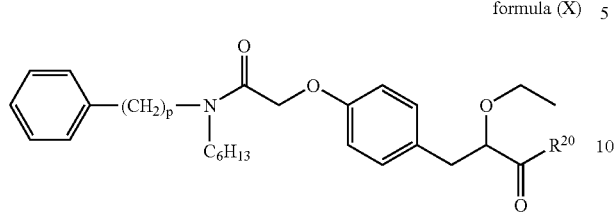

formula (X)

in which m is as previously defined and $R^{20}$ represents a protecting group for a carboxylic hydroxy group as described in the standard text "Protective Groups in Organic Synthesis", 2 Edition (1991) by Greene and Wuts, with a de-protecting agent. The protecting group may also be a resin, such as Wang resin or 2-chlorotrityl chloride resin. Protecting groups may be removed in accordance to techniques which are well known to those skilled in the art. One such protecting group is where $R^{20}$ represents a C1-6 alkoxy group or an arylalkoxy group e.g. benzyloxy, such that $COR^{20}$ represents an ester. Such esters can be reacted with a de-protecting agent e. g. a hydrolysing agent, for example lithium hydroxide in a mixture of THF and water, at a temperature in the range of 0-100° C. to give compounds of formula (II). Compounds of formula (X) may be prepared by reacting the S-enantiomer of a compound of formula (XI)

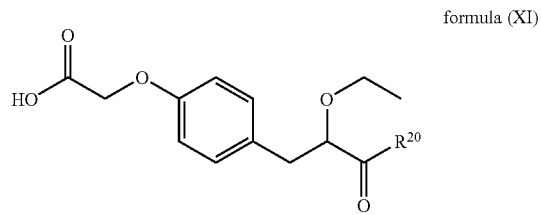

formula (XI)

in which $R^{20}$ is as previously defined with a compound of formula (XII)

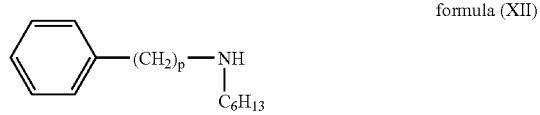

formula (XII)

in which p is as previously defined in an inert solvent, for example dichloromethane, in the presence of a coupling agent, for example a carbodimide, eg 1-(3-dimethylaminopropyl)-3-ethylcarbodiimide, and optionally in the presence of a catalyst, for example a basic catalyst, e.g. 4-dimethylaminopyridine, at a temperature in the range of −25 C to 150° C.

Compounds of formula (XI) and (XII) may be prepared by methods described in the Examples or by analogous methods known to those skilled in the art.

Compounds of formula (X) and (XI) are useful intermediates in the preparation of compounds of formula I and are believed to be novel. The S-enantiomers of compounds of formula (X) and (XI) are preferred.

Compounds of formula (III) may be prepared by reacting the S enatiomer of a compound of formula (XIII)

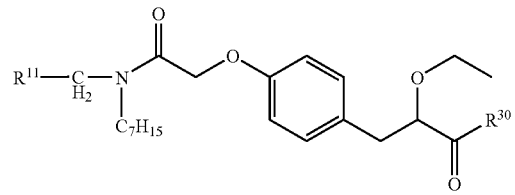

formula (XIII)

in which $R^{11}$ is as previously defined and $R^{30}$ represents a protecting group for a carboxylic hydroxy group as described in the standard text "Protective Groups in Organic Synthesis", 2 Edition (1991) by Greene and Wuts, with a de-protecting agent. The protecting group may also be a resin, such as Wang resin or 2-chlorotrityl chloride resin.

Protecting groups may be removed in accordance to techniques which are well known to those skilled in the art. One such protecting group is where $R^{30}$ represents a C1-6 alkoxy group or anarylalkoxy group e.g., benzyl, such that $COR^{30}$ represents an ester. Such esters can be reacted with a de-protecting reagent e.g., a hydrolysing agent, for example lithium hydroxide in a mixture of THF and water, at a temperature in the range of 0-100° C. to give compounds of formula (III).

Compounds of formula (XIII) may be prepared by reacting the S enantiomer of a compound of formula (XIV)

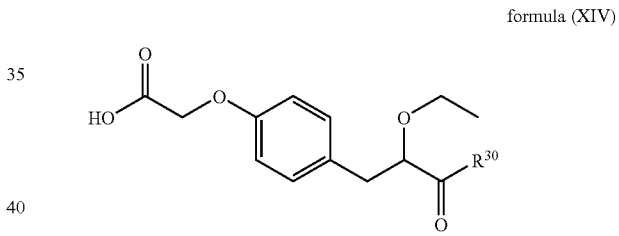

formula (XIV)

in which $R^{30}$ is as previously defined with a compound of formula (XV)

formula (XV)

in which $R^{11}$ is as previously defined in an inert solvent, for example dichloromethane, in the presence of a coupling agent, for example a carbodimide, e.g. 1-(3-dimethylaminopropyl)-3-ethylcarbodiimide, and optionally in the presence of a catalyst, for example a basic catalyst, e.g. 4-dimethylaminopyridine, at a temperature in the range of −25° C. to 150° C.

Compounds of formula (XIV) and (XV) may be prepared by methods described in the Examples or by analogous methods known to those skilled in the art.

Compounds of formula (XIII) and (XIV) are useful intermediates in the preparation of compounds of formula (III) and are believed to be novel. The S-enantiomers of compounds of formula (XIII) and (XIV) are preferred.

Compounds of formula (IV) may be prepared by reacting the S-enantiomer of a compound of formula (XVI)

formula (XVI)

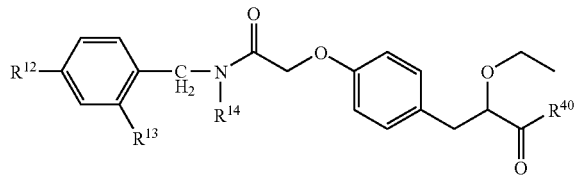

in which $R^{12}$, $R^{13}$ and $R^{14}$ are as previously defined and $R^{40}$ represents a protecting group for a carboxylic hydroxy group as described in the standard text "Protective Groups in Organic Synthesis", 3rd Edition (1999) by Greene and Wuts, with a de-protecting agent. The protecting group may also be a resin, such as Wang resin or 2-chlorotrityl chloride resin. Protecting groups may be removed in accordance to techniques which are well known to those skilled in the art. One such protecting group is where $R^{40}$ represents a $C_{1-6}$alkoxy group for example methoxy or ethoxy or an arylalkoxy group eg benzyloxy, such that $COR^{40}$ represents an ester. Such esters can be reacted with a de-protecting agent e.g., a hydrolysing agent, for example lithium hydroxide in a mixture of THF and water, at a temperature in the range of 0-100° C. to give compounds of formula (IV).

Compounds of formula (XVI) may be prepared by reacting the S-enantiomer of a compound of formula (XVII)

formula (XVII)

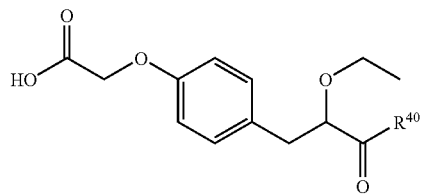

in which $R^{40}$ is as previously defined with a compound of formula (XVIII)

formula (XVIII)

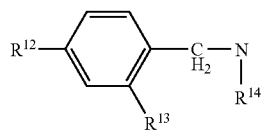

in which $R^{12}$, $R^{13}$ and $R^{14}$ are as previously defined in an inert solvent, for example dichloromethane, in the presence of a coupling agent, for example a carbodimide, e.g., 1-(3-dimethylaminopropyl)-3-ethylcarbodiimide, and optionally in the presence of a catalyst, for example a basic catalyst, e.g., 4-dimethylaminopyridine, at a temperature in the range of −25° C. to 150° C.

Compounds of formula (XVII) and (XVIII) may be prepared by methods described in the Examples or by analogous methods known to those skilled in the art.

Compounds of formula (XVI) and (XVII) are useful intermediates in the preparation of compounds of formula I and are believed to be novel. The S-enantiomers of compounds of formula (XVI) and (XVII) are preferred.

Compounds of formula (IV) may be also prepared by reacting a compound of formula (XIX), formula (XIX)

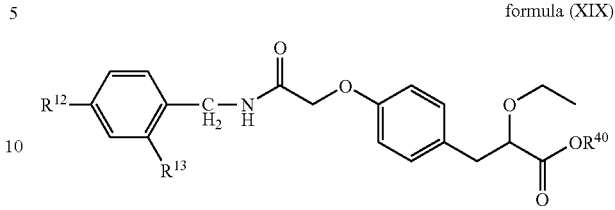

in which $R^{12}$ and $R^{13}$ are as previously defined, $R^{40}$ is H or $OR^{40}$ represents a protecting group for a carboxylic hydroxy group with a compound of formula (XX)

$$R^{14}L \quad\quad\quad (XX)$$

wherein $R^{14}$ is as previously defined and L is a leaving group, in the presence of a base in the presence of an inert solvent at a temperature in the range −25° C. to 150° C. and optionally, when OR represents a protecting group, removal of the protecting group.

In particular a compound of formula (IV) may be prepared by reacting a compound of formula (XXI)

formula (XXI)

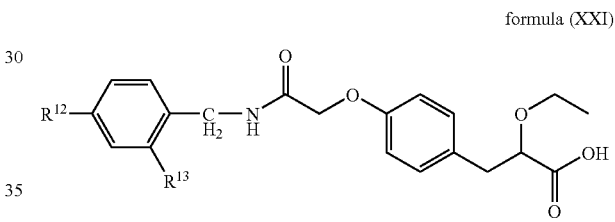

in which $R^{12}$ and $R^{13}$ are as previously defined with a compound of formula (XXII)

$$R^{14}L \quad\quad\quad (XX)$$

wherein $R^{14}$ is as previously defined and L is a leaving group in the presence of a base in the presence of an inert solvent at a temperature in the range −25° C. to 150° C.

The protecting groups $OR^{40}$ and deprotecting agents are described in the standard text "Protective Groups in Organic Synthesis", $3^{rd}$ Edition (1999) by Greene and Wuts, which is herein incorporated by reference. Suitable protecting groups include where $OR^{40}$ represents a $C_{1-6}$alkoxy group eg methoxy or ethoxy group or an arylalkoxy group eg benzyloxy. In particular, when $OR^{40}$ represents a $C_{1-6}$alkoxy group eg ethoxy group or an arylalkoxy group eg benzyloxy, such that $COOR^{40}$ represents an ester then such esters may be reacted with a de-protecting agent e.g. a hydrolysing agent, for example lithium hydroxide in a mixture of THF and water, at a temperature in the range of 0-100° C.

Suitable bases include potassium hydroxide, sodium hydroxide, lithium hydroxide, sodium hydride, potassium tert-butoxide, cesium carbonate, potassium carbonate, or sodium carbonate particularly potassium hydroxide.

Suitable inert solvents include dimethyl sulphoxide, N,N-dimethylformamide, N-methylpyrrolidone or toluene or mixtures thereof, particularly dimethyl sulphoxide.

Suitably L represents bromo, chloro, $OSO_2CH_3$, OTosyl, $OSO_2CF_3$, OC(O)OR, OP(O)(OR)$_2$ or $OSO_2OR$. Particularly L is chloro or bromo.

Optionally a phase transfer catalyst may be used for example an alkylammonium salt for example a tetraalkylammonium halide salt eg tetrabutyl ammonium bromide.

Compounds of formula (XIX) in which $R^{40}$ is H (or compound (XXI) may be prepared by reacting a compound of formula (XIX)

formula (XIX)

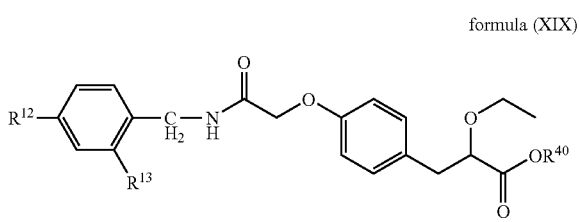

in which $R^1$ and $R^2$ are as previously defined and $OR^{40}$ represents a protecting group for a carboxylic hydroxy group with a de-protecting agent. In particular, $OR^{40}$ represents a $C_{1-6}$alkoxy group eg ethoxy group or an arylalkoxy group eg benzyloxy, such that $COOR^{40}$ represents an ester. Such esters can be reacted with a de-protecting agent e.g. a hydrolysing agent, for example lithium hydroxide in a mixture of THF and water, at a temperature in the range of 0-100° C.

Compounds of formula (XIX) in which $OR^{40}$ represents a protecting group for a carboxylic hydroxy group may be prepared by reacting a compound of formula (XXII)

formula (XXII)

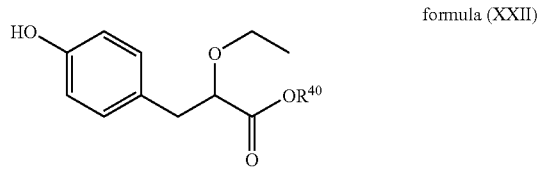

in which $OR^{40}$ is as previously defined with a compound of formula (XXIII)

formula (XXIII)

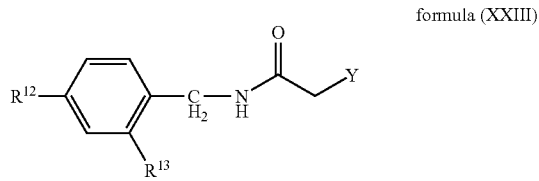

in which $R^{12}$ and $R^{13}$ are as previously defined and Y represents a leaving group, for example halo, particularly chloro, in an inert solvent, for example acetonitrile or methyl isobutylketone, in the presence of a base, for example potassium carbonate, at a temperature in the range of 0° C. to 150° C.

It is believed that the compounds of formula (XIX) in which R is H (compound (XXI)) for example (2S)-3-[4-(2-{[2-fluoro-4-(trifluoromethyl)benzyl]amino}-2-oxoethoxy)phenyl]-2-ethoxy propanoic acid;

(2S)-3-(4-{2-[4-Chlorobenzylamino]-2-oxoethoxy}phenyl)-2-ethoxypropanoic acid;

(2S)-2-Ethoxy-3-[4-(2-{4-(trifluoromethoxy)benzylamino}-2-oxoethoxy)phenyl]propanoic acid; and (2S)-2-Ethoxy-3-[4-(2-{4-(trifluoromethyl)benzylamino}-2-oxoethoxy)phenyl]propanoic acid;

are novel. These compounds have the advantage of being solid and therefore offer an opportunity for purification and isolation during the reaction sequence if desired. These compounds are also preferably modulators of PPAR alpha and/or PPAR gamma and are generally useful in treating the indications described herein.

Also described herein is a compound of formula (XIX) in which $OR^{40}$ represents a protecting group for a carboxylic hydroxy group in particular $OR^{40}$ represents for example a $C_{1-6}$alkoxy group e.g. methoxy, ethoxy or propoxy or an arylalkoxy group wherein aryl is phenyl optionally substituted by $C_{1-6}$alkyl, $C_{1-6}$alkoxy or halo, e.g. benzyloxy, for example a compound of formula (XXIV)

formula (XXIV)

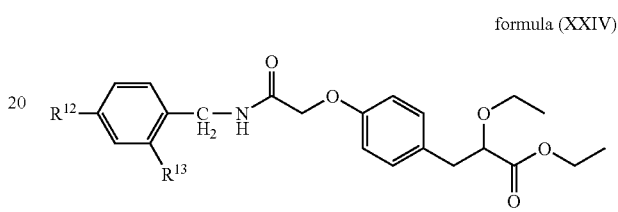

in which $R^{12}$ and $R^{13}$ are as previously defined.

Compounds of formula (V) may be prepared by modifying a compound of formula (XXV)

formula (XXV)

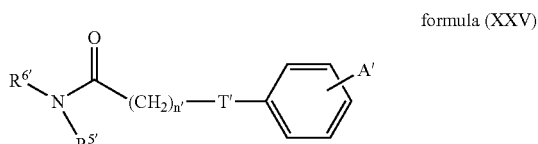

wherein

A' is situated in the ortho, meta or para position and represents

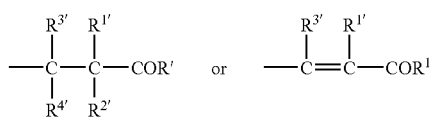

in which $R^{1'}$, $R^{2'}$ $R^{3'}$ and $R^{4'}$ are as previously defined and R' represents —$OR^{P'}$, wherein $R^{P'}$ is a protecting group for a carboxylic hydroxy group as described in the standard text "Protective Groups in Organic Synthesis", 2nd Edition (1991) by Greene and Wuts, with a de-protecting agent. The protecting group may also be a resin, such as Wang resin or 2-chlorotrityl chloride resin. Protecting groups may be removed in accordance to techniques that are well known to those skilled in the art. One such protecting group is where —$OR^{P'}$ represents a $C_{1-6}$alkoxy group or an arylalkoxy group e.g. benzyloxy, such that $COR^{P'}$ represents an ester. Such esters can be reacted with a de-protecting agent e.g. a hydrolysing agent, for example lithium hydroxide in a mixture of THF and water, at a temperature in the range of 0-100° C. to give compounds of formula (V).

Compounds of formula (XXV) may be prepared by reacting a compound of formula (XXVI)

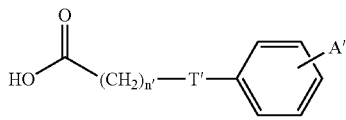

formula (XXVI)

in which A', T' and n' are as previously defined with a compound of formula (XXVII)

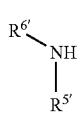

formula (XXVII)

in which R⁵' and R⁶' are as previously defined in an inert solvent, for example dichloromethane, in the presence of a coupling agent, for example a carbodimide, e.g. 1-(3-dimethylaminopropyl)-3-ethylcarbodiimide or oxalyl chloride, optionally in the presence of a base particularly diisopropylethyl amine, and optionally in the presence of a catalyst, for example a basic catalyst, eg 4-dimethylaminopyridine, at a temperature in the range of $-25°$ C. to $150°$ C.

Compounds of formulae (XXVI) and (XXVII) may be prepared by methods described in the Examples or by analogous methods known to those skilled in the art.

Compounds of formula (XXV) may be prepared by reacting a compound of formula (XXVIII)

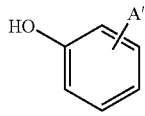

formula (XXVIII)

in which A' is as previously defined with a compound of formula (XXIX)

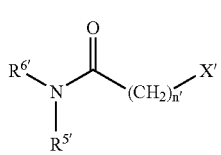

formula (XXIX)

in which $R^{5'}$ and $R^{6'}$ are as previously defined and X' represents a leaving group, for example a halide, $OSO_2CH_3$, OTosyl, ONosyl, $OSO_2CF_3$, OC(O)OR, OP(O)(OR)$_2$ or $OSO_2OR$, particularly chloro or bromo, in an inert solvent, for example acetonitrile, methyl isobutylketone, N-methylpyrrolidone, toluene, toluene/water, ethanol or isopropylacetate in the presence of a base, for example potassium carbonate, sodium hydroxide or triethylamine, at a temperature in the range of $-25°$ C. to $150°$ C. Optionally a catalyst may be used for example iodide or a quarternary ammonium salt, particularly sodium iodide or tetra-n-butylammonium -iodide, -bromide, -acetate or -hydrogensulphate.

Compounds of formulae (XXVIII) and (XXIX) may be prepared by methods described in the Examples or by analogous methods known to those skilled in the art.

Formulae (XXIX) can be for example:
2-chloro-N-(2,4-difluorobenzyl)-N-octylacetamide
2-chloro-N-(2,4-difluorobenzyl)-N-nonylacetamide
2-chloro-N-(2,4-difluorobenzyl)-N-(4-ethylbenzyl)acetamide
2-chloro-N-(2,4-difluorobenzyl)-N-methylacetamide
2-chloro-N-heptyl-N-[(1-methyl-1H-indol-2-yl)methyl]acetamide
2-chloro-N-(2,3-dimethoxybenzyl)-N-heptylacetamide
N-butyl-2-chloro-N-(2,3-dimethoxybenzyl)acetamide
2-chloro-N-(4-chlorobenzyl)-N-(4-isopropylbenzyl)acetamide
2-chloro-N-(cyclohexylmethyl)-N-(2,4-difluorobenzyl)acetamide
2-chloro-N-ethyl-N-(2-fluorobenzyl)acetamide
N-[4-(benzyloxy)benzyl]-N-butyl-2-chloroacetamide
2-chloro-N-hexyl-N-(2-phenylethyl)acetamide
2-chloro-N,N-bis(4-chlorobenzyl)acetamide
N-(4-tert-butylbenzyl)-2-chloro-N-(4-chlorobenzyl)acetamide
2-chloro-N-(4-chlorobenzyl)-N-[4-(trifluoromethyl)benzyl]acetamide
2-chloro-N,N-bis[4-(trifluoromethyl)benzyl]acetamide
N-benzyl-2-chloro-N-ethylacetamide
N-(4-tert-butylbenzyl)-2-chloro-N-ethylacetamide
2-chloro-N-ethyl-N-[4-(trifluoromethyl)benzyl]acetamide
2-chloro-N-(4-cyclohexylbutyl)-N-(2,4-difluorobenzyl)acetamide
N-(2-biphenyl-4-ylethyl)-2-chloro-N-(2,4-difluorobenzyl)acetamide
2-chloro-N-(4-chlorobenzyl)-N-(2-methoxybenzyl)acetamide
4-{[butyl(chloroacetyl)amino]methyl}phenyl methanesulfonate Compounds of formulae (XXV), (XXVI), (XXVII), (XXVIII) and (XXIX) can be useful intermediates in the preparation of compounds of formula (V). The S-enantiomers of compounds of formula (XXV), (XXVI), and (XXVIII) are preferred. The compounds of the invention may be isolated from their reaction mixtures using conventional techniques.

The compounds of the invention may be isolated from their reaction mixtures using conventional techniques.

In another aspect the present invention provides a process for preparing a pharmaceutically acceptable salt of the compounds described herein comprising reacting the acid obtained by one of the processes of the present invention with a base, optionally in the presence of a solvent and isolating the salt.

Persons skilled in the art will appreciate that, in order to obtain compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

The expression "inert solvent" refers to a solvent that does not react with the starting materials, reagents, intermediates or products in a manner that adversely affects the yield of the desired product.

Pharmaceutical Preparations:

The compounds of the invention will normally be administered via the oral, parenteral, intravenous, intramuscular, subcutaneous or in other injectable ways, buccal, rectal, vaginal, transdermal and/or nasal route and/or via inhalation, in the form of pharmaceutical preparations comprising the active ingredient either as a free acid, or a pharmaceutical acceptable organic or inorganic base addition salt, in a pharmaceutically acceptable dosage form. Depending upon the disorder and patient to be treated and the route of administration, the compositions may be administered at varying doses.

Suitable daily doses of the compounds of the invention in therapeutical treatment of humans are about 0.0001-100 mg/kg body weight, preferably 0.001-10 mg/kg body weight.

Oral formulations are preferred particularly tablets or capsules which may be formulated by methods known to those skilled in the art to provide doses of the active compound in the range of 0.5 mg to 500 mg for example 1 mg, 3 mg, 5 mg, 10 mg, 25 mg, 50 mg, 100 mg and 250 mg.

According to a further aspect of the invention there is thus provided a pharmaceutical formulation including any of the compounds of the invention, or pharmaceutically acceptable derivatives thereof, in admixture with pharmaceutically acceptable adjuvants, diluents and/or carriers.

Pharmacological Properties:

The present compounds of formula (I) are useful for the prophylaxis and/or treatment of clinical conditions associated with inherent or induced reduced sensitivity to insulin (insulin resistance) and associated metabolic disorders (also known as metabolic syndrome). These clinical conditions will include, but will not be limited to, general obesity, abdominal obesity, arterial hypertension, hyperinsulinaemia, hyperglycaemia, type 2 diabetes and the dyslipidaemia characteristically appearing with insulin resistance. This dyslipidaemia, also known as the atherogenic lipoprotein profile, is characterised by moderately elevated non-esterified fatty acids, elevated very low density lipoprotein (VLDL) triglyceride rich particles, high Apo B levels, low high density lipoprotein (HDL) levels associated with low apoAI particle levels and high Apo B levels in the presence of small, dense, low density lipoproteins (LDL) particles, phenotype B.

The compounds of the present invention are expected to be useful in treating patients with combined or mixed hyperlipidemias or various degrees of hypertriglyceridemias and postprandial dyslipidemia with or without other manifestations of the metabolic syndrome.

Treatment with the present compounds is expected to lower the cardiovascular morbidity and mortality associated with atherosclerosis due to their antidyslipidaemic as well as antiinflammatory properties. The cardiovascular disease conditions include macro-angiopathies of various internal organs causing myocardial infarction, congestive heart failure, cerebrovascular disease and peripheral arterial insufficiency of the lower extremities. Because of their insulin sensitizing effect the compounds of a formula described herein are also expected to prevent or delay the development of type 2 diabetes from the metabolic syndrome and diabetes of pregnancy. Therefore the development of long-term complications associated with chronic hyperglycaemia in diabetes mellitus such as the micro-angiopathies causing renal disease, retinal damage and peripheral vascular disease of the lower limbs are expected to be delayed. Furthermore the compounds may be useful in treatment of various conditions outside the cardiovascular system whether or not associated with insulin resistance, like polycystic ovarian syndrome, obesity, cancer and states of inflammatory disease including neurodegenerative disorders such as mild cognitive impairment, Alzheimer's disease, Parkinson's disease and multiple sclerosis. The compounds may be useful in treatment of psoriasis.

The compounds of the present invention are expected to be useful in controlling glucose levels in patients suffering from type 2 diabetes.

The present invention provides a method of treating or preventing dyslipidemias, the insulin resistance syndrome and/or metabolic disorders (as defined above) comprising the administration of a compound of a formula described herein to a mammal (particularly a human) in need thereof.

The present invention provides a method of treating or preventing type 2 diabetes comprising the administration of an effective amount of a compound of a formula described herein to a mammal (particularly a human) in need thereof.

The present invention provides a method of treating or preventing atherosclerosis comprising the administration of an effective amount of a compound of a formula described herein to a mammal (particularly a human) in need thereof.

In a further aspect the present invention provides the use of a compound of a formula described herein as a medicament.

In a further aspect the present invention provides the use of a compound of a formula described herein in the manufacture of a medicament for the treatment of insulin resistance and/or metabolic disorders.

Combination Therapy:

The compounds of the invention may be combined with another therapeutic agent that is useful in the treatment of disorders associated with the development and progress of atherosclerosis such as hypertension, hyperlipidaemias, dyslipidaemias, diabetes and obesity. The compounds of the invention may be combined with another therapeutic agent that decreases the ratio of LDL:HDL or an agent that causes a decrease in circulating levels of LDL-cholesterol. In patients with diabetes mellitus the compounds of the invention may also be combined with therapeutic agents used to treat complications related to micro-angiopathies.

The compounds of the invention may be used alongside other therapies for the treatment of metabolic syndrome or type 2 diabetes and its associated complications, these include biguanide drugs, for example metformin, phenformin and buformin, insulin (synthetic insulin analogues, amylin) and oral antihyperglycemics (these are divided into prandial glucose regulators and alpha-glucosidase inhibitors). An example of an alpha-glucosidase inhibitor is acarbose or voglibose or miglitol. An example of a prandial glucose regulator is repaglinide or nateglinide.

In another aspect of the invention, the compound of a formula described herein, or a pharmaceutically acceptable salt, solvate, solvate of such a salt or a prodrug thereof, may be administered in association with another PPAR modulating agent. PPAR modulating agents include but are not limited to a PPAR alpha and/or gamma and /or delta agonist, or pharmaceutically acceptable salts, solvates, solvates of such salts or prodrugs thereof. Suitable PPAR alpha and/or gamma agonists, pharmaceutically acceptable salts, solvates, solvates of such salts or prodrugs thereof are well known in the art. These include the compounds described in WO 01/12187, WO 01/12612, WO 99/62870, WO 99/62872, WO 99/62871, WO 98/57941, WO 01/40170, J Med Chem, 1996, 39, 665, Expert Opinion on Therapeutic Patents, 10 (5), 623-634 (in particular the compounds described in the patent applications listed on page 634) and J Med Chem, 2000, 43, 527 which are all incorporated herein by reference. Particularly a PPAR alpha and/or gamma agonist refers to BMS 298585, clofibrate, fenofibrate, bezafibrate, gemfibrozil and ciprofibrate; GW 9578, pioglitazone, rosiglitazone, rivoglitazone, balaglitazone, KRP-297, JTT-501, SB 213068, GW 1929, GW 7845, GW 0207, L-796449, L-165041 and GW 2433. Particularly a PPAR alpha and/or gamma agonist refers to (S)-2-ethoxy-3-[4-(2-{4-methanesulphonyloxy-phenyl}ethoxy)phenyl]propanoic acid and pharmaceutically acceptable salts thereof.

In addition the combination of the invention may be used in conjunction with a sulfonylurea for example: glimepiride, glibenclamide (glyburide), gliclazide, glipizide, gliquidone, chloropropamide, tolbutamide, acetohexamide, glycopyramide, carbutamide, glibonuride, glisoxepid, glybuthiazole, glibuzole, glyhexamide, glymidine, glypinamide, phenbutamide, tolcylamide and tolazamide. Preferably the sulfonylurea is glimepiride or glibenclamide (glyburide). More preferably the sulfonylurea is glimepiride. Therefore the present invention includes administration of a compound of the present invention in conjunction with one, two or more existing therapies described in this paragraph. The doses of the other existing therapies for the treatment of type 2 diabetes and its associated complications will be those known in the art and approved for use by regulatory bodies for example the FDA and may be found in the Orange Book published by the FDA. Alternatively smaller doses may be used as a result of the benefits derived from the combination.

The present invention also includes a compound of the present invention in combination with a cholesterol-lowering agent. The cholesterol-lowering agents referred to in this application include but are not limited to inhibitors of HMG-CoA reductase (3-hydroxy-3-methylglutaryl coenzyme A reductase). Suitably the HMG-CoA reductase inhibitor is a statin selected from the group consisting of atorvastatin, bervastatin, cerivastatin, dalvastatin, fluvastatin, itavastatin, lovastatin, mevastatin, nicostatin, nivastatin, pravastatin and simvastatin, or a pharmaceutically acceptable salt, especially sodium or calcium, or a solvate thereof, or a solvate of such a salt. A particular statin is atorvastatin, or a pharmaceutically acceptable salt, solvate, solvate of such a salt or a prodrug thereof. A more particular statin is atorvastatin calcium salt. A particularly preferred statin is, however, a compound with the chemical name (E)-7-[4-(4-fluorophenyl)-6-isopropyl-2-[methyl(methylsulfonyl)-amino]-pyrimidin-5-yl](3R,5S)-3,5-dihydroxyhept-6-enoic acid, [also known as (E)-7-[4-(4-fluorophenyl)-6-isopropyl-2-[N-methyl-N-(methylsulfonyl)-amino]pyrimidin-5-yl](3R,5S)-3,5-dihydroxyhept-6-enoic acid] or a pharmaceutically acceptable salt or solvate thereof, or a solvate of such a salt. The compound (E)-7-[4-(4-fluorophenyl)-6-isopropyl-2-[methyl-(methylsulfonyl)-amino]-pyrimidin-5-yl](3R,5S)-3,5-dihydroxyhept-6-enoic acid, and its calcium and sodium salts are disclosed in European Patent Application, Publication No. EP-A-0521471, and in Bioorganic and Medicinal Chemistry, (1997), 5(2), 437-444. This latter statin is now known under its generic name rosuvastatin.

In the present application, the term "cholesterol-lowering agent" also includes chemical modifications of the HMG-CoA reductase inhibitors, such as esters, prodrugs and metabolites, whether active or inactive.

The present invention also includes a compound of the present invention in combination with a bile acid sequestering agent, for example colestipol or cholestyramine or cholestagel.

The present invention also includes a compound of the present invention in combination with an inhibitor of the ileal bile acid transport system (IBAT inhibitor).

Suitable compounds possessing IBAT inhibitory activity have been described, see for instance the compounds described in WO 93/16055, WO 94/18183, WO 94/18184, WO 96/05188, WO 96/08484, WO 96/16051, WO 97/33882, WO 98/07449, WO 98/03818, WO 98/38182, WO 99/32478, WO 99/35135, WO 98/40375, WO 99/35153, WO 99/64409, WO 99/64410, WO 00/01687, WO 00/47568, WO 00/61568, WO 00/62810, WO 01/68906, DE 19825804, WO 00/38725, WO 00/38726, WO 00/38727, WO 00/38728, WO 00/38729, WO 01/68906, WO 01/66533, WO 02/32428, WO 02/50051, EP 864 582, EP489423, EP549967, EP573848, EP624593, EP624594, EP624595 and EP624596 and the contents of these patent applications are incorporated herein by reference.

Particular classes of IBAT inhibitors suitable for use in the present invention are benzothiepines, and the compounds described in the claims, particularly claim 1, of WO 00/01687, WO 96/08484 and WO 97/33882 are incorporated herein by reference. Other suitable classes of IBAT inhibitors are the 1,2-benzothiazepines, 1,4-benzothiazepines and 1,5-benzothiazepines. A further suitable class of IBAT inhibitors is the 1,2,5-benzothiadiazepines.

One particular suitable compound possessing IBAT inhibitory activity is (3R,5R)-3-butyl-3-ethyl-1,1-dioxido-5-phenyl-2,3,4,5-tetrahydro-1,4-benzothiazepin-8-yl β-D-glucopyranosiduronic acid (EP 864 582). Other suitable IBAT inhibitors include one of:

1,1-dioxo-3,3-dibutyl-5-phenyl-7-methylthio-8-(N-{(R)-1'-phenyl-1'-[N'-(carboxymethyl)carbamoyl]methyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(carboxymethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-1'-phenyl-1'-[N'-(2-sulphoethyl)carbamoyl]methyl}carbamoylmethoxy)-2,3,4,5-tetrahydro-1,5-benzothiazepine;

1,1-dioxo-3-butyl-3-ethyl-5-phenyl-7-methylthio-8-(N-{(R)-1'-phenyl-1'-[N'-(2-sulphoethyl)carbamoyl]methyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-sulphoethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-sulphoethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(5-carboxypentyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{α-[N'-(2-sulphoethyl)carbamoyl]-2-fluorobenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(R)-(2-hydroxy-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(R)-(2-hydroxy-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-{N-[(R)-α-(N'-{(R)-1-[N"-(R)-(2-hydroxy-1-carboxyethyl)carbamoyl]-2-hydroxyethyl}carbamoyl)benzyl]carbamoylmethoxy}-2,3,4,5-tetrahydro-1,5-benzothiazepine;

1,1-dioxo-3-butyl-3-ethyl-5-phenyl-7-methylthio-8-(N-{α-[N'-(carboxymethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{α-[N'-((ethoxy)(methyl)phosphoryl-methyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-{N-[(R)-α-(N'-{2-[(hydroxy)(methyl)phosphoryl]ethyl}carbamoyl)benzyl]carbamoylmethoxy}-2,3,4,5-tetrahydro-1,5-benzothiazepine;

1,1-dioxo-3,3-dibutyl-5-phenyl-7-methylthio-8-(N-{(R)-α-[N'-(2-methylthio-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-{N-[(R)-α-(N'-{2-[(methyl)(ethyl)phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-{N-[(R)-α-(N'-{2-[(methyl)(hydroxy) phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-(N-{(R)-α-[(R)-N'-(2-methylsulphinyl-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methoxy-8-[N-{(R)-α-[N'-(2-sulphoethyl)carbamoyl]-4-hydroxybenzyl}carbamoylmethoxy]-2,3,4,5-tetrahydro-1,5-benzothiazepine;

1,1-dioxo-3,3-dibutyl-5-phenyl-7-methylthio-8-(N-{(R)-α-[N-((R)-1-carboxy-2-methylthio-ethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-(R)-hydroxypropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-methylpropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxybutyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxypropyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-(R)-hydroxypropyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-(2-sulphoethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((R)-1-carboxy-2-methylthioethyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-{(S)-1-[N-((S)-2-hydroxy-1-carboxyethyl)carbamoyl]propyl}carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-methylpropyl)carbamoyl]benzyl}carbamoylmethoxy)-2,3,4,5-tetrahydro-1,2,5-benzothiadiazepine;

1,1-Dioxo-3,3-dibutyl-5-phenyl-7-methylthio-8-(N-{(R)-α-[N-((S)-1-carboxypropyl)carbamoyl]-4-hydroxybenzyl}carbamoylmethoxy)-2,3,4,5-tetrahydro-1,2,5-benzothiadiazepine;

1,1-Dioxo-3,3-dibutyl-5-phenyl-7-methylthio-8-[N-((R/S)-α-{N-[1-(R)-2-(S)-1-hydroxy-1-(3,4-dihydroxyphenyl)prop-2-yl]carbamoyl}-4-hydroxybenzyl)carbamoylmethoxy]-2,3,4,5-tetrahydro-1,2,5-benzothiadiazepine;

1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxyhexyl)carbamoyl]-4-hydroxybenzyl}carbamoylmethoxy)-2,3,4,5-tetrahydro-1,2,5-benzothiadiazepine; and 1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxyhexyl)carbamoyl]benzyl}carbamoylmethoxy)-2,3,4,5-tetrahydro-1,2,5-benzothiadiazepine;

or a pharmaceutically acceptable salt, solvate, solvate of such a salt or a prodrug thereof.

According to an additional further aspect of the present invention there is provided a combination treatment comprising the administration of an effective amount of a compound of the a formula described herein, or a pharmaceutically acceptable salt, solvate, solvate of such a salt or a prodrug thereof, optionally together with a pharmaceutically acceptable diluent or carrier, with the simultaneous, sequential or separate administration one or more of the following agents selected from:

a CETP (cholesteryl ester transfer protein) inhibitor, for example those referenced and described in WO 00/38725 page 7 line 22-page 10, line 17 which are incorporated herein by reference;

a cholesterol absorption antagonist for example azetidinones such as SCH 58235 and those described in U.S. Pat. No. 5,767,115 which are incorporated herein by reference;

a MTP (microsomal transfer protein) inhibitor for example those described in Science, 282, 751-54, 1998 which are incorporated herein by reference;

a nicotinic acid derivative, including slow release and combination products, for example, nicotinic acid (niacin), acipimox and niceritrol;

a phytosterol compound for example stanols;

probucol;

an omega-3 fatty acid for example Omacor™;

an anti-obesity compound for example orlistat (EP 129, 748) and sibutramine (GB 2,184,122 and U.S. Pat. No. 4,929, 629);

an antihypertensive compound for example an angiotensin converting enzyme (ACE) inhibitor, an angiotensin II receptor antagonist, an andrenergic blocker, an alpha andrenergic blocker, a beta andrenergic blocker for example metoprolol, a mixed alpha/beta andrenergic blocker, an andrenergic stimulant, calcium channel blocker, an AT-1 blocker, a saluretic, a diuretic or a vasodilator;

a CB1 antagonist or inverse agonist for example as described in WO01/70700 and EP 65635;

a Melanin concentrating hormone (MCH) antagonist;

a PDK inhibitor; or modulators of nuclear receptors for example LXR, FXR, RXR, and RORalpha;

or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

Particular ACE inhibitors or pharmaceutically acceptable salts, solvates, solvate of such salts or a prodrugs thereof, including active metabolites, which can be used in combination with a compound of a formula described herein include but are not limited to, the following compounds: alacepril, alatriopril, altiopril calcium, ancovenin, benazepril, benazepril hydrochloride, benazeprilat, benzoylcaptopril, captopril, captopril-cysteine, captopril-glutathione, ceranapril, ceranopril, ceronapril, cilazapril, cilazaprilat, delapril, delapril-diacid, enalapril, enalaprilat, enapril, epicaptopril, foroxymithine, fosfenopril, fosenopril, fosenopril sodium, fosinopril, fosinopril sodium, fosinoprilat, fosinoprilic acid, glycopril, hemorphin-4, idrapril, imidapril, indolapril, indolaprilat, libenzapril, lisinopril, lyciumin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spiropril hydrochloride, temocapril, temocapril hydrochloride, teprotide, trandolapril, trandolaprilat, utibapril, zabicipril, zabiciprilat, zofenopril and zofenoprilat. Preferred ACE inhibitors for use in the present invention are ramipril, ramiprilat, lisinopril, enalapril and enalaprilat. More preferred ACE inhibitors for uses in the present invention are ramipril and ramiprilat.

Preferred angiotensin II antagonists, pharmaceutically acceptable salts, solvates, solvate of such salts or a prodrugs thereof for use in combination with a compound of a formula described herein include, but are not limited to, compounds: candesartan, candesartan cilexetil, losartan, valsartan, irbesartan, tasosartan, telmisartan and eprosartan. Particularly preferred angiotensin II antagonists or pharmaceutically acceptable derivatives thereof for use in the present invention are candesartan and candesartan cilexetil.

Therefore in an additional feature of the invention, there is provided a method for for the treatment of type 2 diabetes and its associated complications in a warm-blooded animal, such as man, in need of such treatment which comprises administering to said animal an effective amount of a compound of a formula described herein, or a pharmaceutically acceptable salt, solvate, solvate of such a salt or a prodrug thereof in simultaneous, sequential or separate administration with an effective amount of one the other compounds described in this combination section, or a pharmaceutically acceptable salt, solvate, solvate of such a salt or a prodrug thereof.

Therefore in an additional feature of the invention, there is provided a method of treating hyperlipidemic conditions in a warm-blooded animal, such as man, in need of such treatment which comprises administering to said animal an effective amount of a compound of a formula described herein, or a pharmaceutically acceptable salt, solvate, solvate of such a salt or a prodrug thereof in simultaneous, sequential or separate administration with an effective amount of one the other compounds described in this combination section or a pharmaceutically acceptable salt, solvate, solvate of such a salt or a prodrug thereof.

According to a further aspect of the invention there is provided a pharmaceutical composition which comprises a compound of a formula described herein, or a pharmaceutically acceptable salt, solvate, solvate of such a salt or a prodrug thereof, and one of the other compounds described in this combination section or a pharmaceutically acceptable salt, solvate, solvate of such a salt or a prodrug thereof, in association with a pharmaceutically acceptable diluent or carrier.

According to a further aspect of the present invention there is provided a kit comprising a compound of a formula described herein, or a pharmaceutically acceptable salt, solvate, solvate of such a salt or a prodrug thereof, and one of the other compounds described in this combination section or a pharmaceutically acceptable salt, solvate, solvate of such a salt or a prodrug thereof.

According to a further aspect of the present invention there is provided a kit comprising:

a) a compound of a formula described herein, or a pharmaceutically acceptable salt, solvate, solvate of such a salt or a prodrug thereof, in a first unit dosage form;

b) one of the other compounds described in this combination section or a pharmaceutically acceptable salt, solvate, solvate of such a salt or a prodrug thereof; in a second unit dosage form; and c) container means for containing said first and second dosage forms.

According to a further aspect of the present invention there is provided a kit comprising:

a) a compound of a formula described herein, or a pharmaceutically acceptable salt, solvate, solvate of such a salt or a prodrug thereof, together with a pharmaceutically acceptable diluent or carrier, in a first unit dosage form;

b) one of the other compounds described in this combination section or a pharmaceutically acceptable salt, solvate, solvate of such a salt or a prodrug thereof, in a second unit dosage form; and c) container means for containing said first and second dosage forms.

According to another feature of the invention there is provided the use of a compound of the a formula described herein, or a pharmaceutically acceptable salt, solvate, solvate of such a salt or a prodrug thereof, and one of the other compounds described in this combination section, or a pharmaceutically acceptable salt, solvate, solvate of such a salt or a prodrug thereof, in the manufacture of a medicament for use in the treatment of metabolic syndrome or type 2 diabetes and its associated complications in a warm-blooded animal, such as man.

According to another feature of the invention there is provided the use of a compound of the a formula described herein, or a pharmaceutically acceptable salt, solvate, solvate of such a salt or a prodrug thereof, and one of the other compounds described in this combination section, or a pharmaceutically acceptable salt, solvate, solvate of such a salt or a prodrug thereof, in the manufacture of a medicament for use in the treatment of hyperlipidaemic conditions in a warm-blooded animal, such as man.

According to a further aspect of the present invention there is provided a combination treatment comprising the administration of an effective amount of a compound of the a formula described herein, or a pharmaceutically acceptable salt, solvate, solvate of such a salt or a prodrug thereof, optionally together with a pharmaceutically acceptable diluent or carrier, with the simultaneous, sequential or separate administration of an effective amount of one of the other compounds described in this combination section, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

EXAMPLES

¹H NMR and ¹³C NMR measurements were performed on a Varian Mercury 300 or Varian UNITY plus 400, 500 or 600 spectrometers, operating at 1 H frequencies of 300, 400, 500 and 600 MHz, respectively, and at ¹³C frequencies of 75, 100, 125 and 150 MHz, respectively. Measurements were made on the delta scale (δ).

Unless otherwise stated, chemical shifts are given in ppm with the solvent as internal standard.

Abbreviations:
DMSO dimethyl sulfoxide
THF tetrahydrofuran
Pd/C palladium on charcoal
DMAP dimethylaminopyridine
t triplet
s singlet
d doublet
q quartet
m multiplet
bs broad singlet
dm doublet of multiplet
bt broad triplet
dd doupblet of doublet Example 1

(2S)-3-(4-{2-[Benzyl(hexyl)amino]-2-oxoethoxy}phenyl)-2-ethoxypropanoic acid (i) Ethyl(2S)-3-{4-[2-(benzeloxy)-2-oxoethoxylphenyl}-2-ethoxypropanoate To a solution of ethyl(2S)-2-ethoxy-3-(4-hydroxyphenyl)propanoate (23.8 g, 100 mmol, prepared as described in WO99/62872) in acetonitrile (200 mL) was added anhydrous potassium carbonate (31.9 g, 231 mmol) followed by benzyl bromoacetate (17.4 mL, 110 mmol) and the reaction mixture was refluxed overnight. The reaction mixture was allowed to cool to room temperature, insoluble salts were filtered off and the solution was concentrated in vacuo. The residue was taken up in ethyl acetate (300 mL), and the organic phase was washed with aqueous NaHCO$_3$ (3×100 mL) and brine (100 mL), dried over anhydrous MgSO$_4$, and concentrated in vacuo. Purification on silica gel with methylene chloride as the eluent and collection of pure fractions yielded 22.4 g (58%) of a yellow oil.

¹H NMR (400 MHz,CDCl3): δ 1.16 (t, 3H), 1.22 (t, 3H), 2.93-2.97 (m, 2H), 3.35 (m, 1H), 3.60 (m, 1H), 3.97 (m, 1H), 4.16 (q, 2H), 4.64 (s, 2H), 5.23 (s, 2H), 6.82 (d,2H), 7.15 (d, 2H), 7.32-7.39 (m, 5H).

¹³C NMR (100 MHz, CDCl3): δ 14.3, 15.2, 38.6, 60.9, 65.6, 66.3, 67.0, 80.4, 114.6, 128.5, 128.6, 128.7, 130.6, 135.3, 156.7, 169.0, 172.6.

(ii) {4-[(2S)-2,3-Diethoxy-3-oxopropyl]phenoxy}acetic acid

To a solution of ethyl(2S)-3-{4-[2-(benzyloxy)-2-oxoethoxy]phenyl}-2-ethoxypropanoate (22.33 g, 57.8 mmol) in freshly distilled THF (290 mL) was added Pd/C (10%, 3.1 g) and the reaction mixture was hydrogenated under atmospheric pressure at room temperature overnight. The mixture was filtered through a plug of Celite and the filtrate was concentrated in vacuo to afford 16.6 g (97%) of a light yellow oil.

¹H NMR (400MHz, CDCl3): δ 1.15 (t, 3H), 1.21 (t,3H), 2.93-2.98 (m, 2H), 3.35 (m, 1H), 3.60 (m, 1H), 3.97 (m, 1H), 4.16 (q, 2H), 4.65 (s,2H), 6.84 (d, 2H), 7.17 (d, 2H), 8.48 (bs, 1H) 13C NMR (100 MHz, CDCl3):o 14.3, 15.1, 38.5, 61.0, 65.1, 66.4, 80.3, 114.6, 130.7, 130.9, 156.4, 172.7, 173.7

(iii) Ethyl(2S)-3-(4-{2-[benzyl(hexyl)amino]-2-oxoethoxy}phenyl)-2-ethoxypropanoate To a solution of {4-[(2S)-2,3-diethoxy-3-oxopropyl]phenoxy}acetic acid (0.110 g, 0.37 mmol) in methylene chloride (3.7 mL) were added N-hexyl-benzylamine (0.079 g, 0.41 mmol) and DMAP (0.045 g, 0.37 mmol) followed by 1-ethyl-3-(3-dimethylaminopropyl)carbodiimide hydrochloride (0.071 g, 0.37 mmol) and the reaction mixture was stirred at room temperature overnight. The mixture was diluted with methylene chloride (25 mL), and the organic phase was washed with 5% HCl (3×25 mL), aqueous NaHCO$_3$ (25 mL), and brine (25 mL), dried over Na$_2$SO$_4$, and concentrated in, vacuo.

Purification on a prepacked column of silica gel (Isolute®; SPE Column, 5 g Si/25 mL) with methanol (0-1% gradient) in methylene chloride as the eluent yielded 0.139 g (80%) of a colourless oil.

'H NMR (400 MHz, CDCl3): δ 0.81-0.90 (m, 3H), 1.11-1.32 (m, 12H), 1.46-1.62 (m, 2H), 2.88-3.00 (m, 2H), 3.21-3.29 and 3.29-3.40 (2m, 3H, rotamers), 3.59 (m, 1H), 3.95 (m, 1H), 4.10-4.19 (m, 2H), 4.60 and 4.61 (2s, 2H, rotamers), 4.65 and 4.73 (2s, 2H, rotamers), 6.77 and 6.87 (2d, 2H, rotamers), 7.07-7.37 (m, 7H).

¹³C NMR (100 MHz, CDCl3): δ 13.9, 14.2, 15.1, 22.5, 26.5, 27.1, 28.4, 31.4, 31.5, 38.4, 46.3, 46.5, 48.2, 50.5, 60.7, 66.1, 67.5, 67.8, 80.3, 114.4, 114.5, 126.6, 127.3, 127.6, 128.0, 128.5, 128.8, 130.2, 130.2, 130.4, 130.5, 136.6, 137.2, 156.8, 156.9, 168.0, 168.1, 172.4. (The number of peaks is larger than the number of carbon atoms due to rotamers.)

(iv) (2S)-3-(4-{2-[Benzel(hexyl)aminol-2-oxoethoxy}phenyl)-2-ethoxypropanoic acid To a solution of ethyl(2S)-3-(4-{2-[benzyl(hexyl)amino]-2-oxoethoxy}phenyl)-2-ethoxypropanoate (0.080 g, 0.17 mmol) in THF (8.6 mL) was added 4.3 mL of a 0.10 M LiOH solution and the reaction mixture was stirred at room temperature overnight. The reaction mixture was acidified with 2M HCl and extracted with ethyl acetate (3×25 mL). The combined organic phase was washed with brine (25 mL), dried over Na$_2$SO$_4$, and concentrated in vacuo to afford 0.068 g (90%) of a colourless oil.

$^1$H NMR (400 MHz, CDCl3): δ 0.80-0.92 (m, 3H), 1.11-1.18 (m, 3H), 1.18-1.33 (m, 6H), 1.46-1.63 (m, 2H), 2.87-3.11 (m, 2H), 3.20-3.30 and 3.32-3.45 (2m, 3H, rotamers), 3.61 (m, 1H), 4.01 (m, 1H), 4.61 and 4.63 (2s, 2H, rotamers), 4.67 and 4.75 (2s, 2H, rotamers), 6.77 and 6.88 (2d, 2H, rotamers), 7.10-7.40 (m, 7H), 8.79 (bs, 1H).

$^{13}$C NMR (100 MHz,CDCl3): δ 14.0, 15.1, 22.6, 26.6, 27.1, 28.4, 31.5, 31.5, 31.6, 38.1, 46.5, 46.6, 48.5, 50.7, 66.7, 67.4, 67.7, 79.9, 114.6, 114.7, 126.7, 127.5, 127.8, 128.2, 128.7, 129.0, 130.1, 130.1, 130.6, 130.7, 136.5, 137.0, 156.9, 157.0, 168.5, 168.6, 175.6. (The number of peaks is larger than the number of carbon atoms due to rotamers.)

Example 2

(2S)-2-Ethoxy-3-(4-{2-[hexyl(2-phenylethyl)amino]-2-oxoethoxy}phenyl)propanoic acid (i) Ethyl(2S)-2-ethoxy-3-(4-{2-[hexyl(2-phenyl-ethyl)amino]-2-oxoethoxy}phenyl)propanoate To a solution of {4-[(2S)-2,3-diethoxy-3-oxopropyl]phenoxy} acetic acid (0.110 g, 0.37 mmol) in methylene chloride (3.7 mL) were added N-hexyl-2-phenylethylamine (0.080 g, 0.39 mmol) and DMAP (0.045 g, 0.37 mmol) followed by 1-ethyl-3-(3-dimethylaminopropyl)carbodiimide hydrochloride (0.071 g, 0.37 mmol), and the reaction mixture was stirred at room temperature overnight. The mixture was diluted with methylene chloride (25 mL), and the organic phase was washed with 5% HCl (3×25 mL), aqueous NaHCO$_3$ (25 mL) and brine (25 mL), dried over Na$_2$SO$_4$, and concentrated in vacuo.

Purification on a prepacked column of silica gel(Isolute® SPE Column, 5 g Si/25 mL) with methanol (0-1% gradient) in methylene chloride as the eluent yielded 0.125 g (70%) of a colourless oil.

$^1$H NMR (400 MHz, CDCl3): δ 0.82-0.92 (m, 3H), 1.16 (t, 3H), 1.19-1.33 (m, 9H), 1.45-1.65 (m, 2H), 2.82-2.90 (m, 2H), 2.91-2.98 (m, 2H), 3.12-3.21 and 3.29-3.42 (2m, 3H, rotamers) 3.50-3.65 (m, 3H), 3.95 (m, 1H), 4.16 (q, 2H), 4.39 and 4.65 (2s, 2H, rotamers), 6.75 and 6.86 (2d, 2H, rotamers), 7.10-7.34 (m, 7H).

$^{13}$C NMR (100 MHz, CDCl3): δ 14.0, 14.1, 14.3, 15.1, 22.6, 26.5, 26.7, 27.4, 29.0, 31.5, 31.6, 33.9, 35.3, 38.5, 45.9, 48.1, 48.3, 48.9, 60.8, 66.2, 67.5, 80.4, 114.5, 126.4, 126.9, 128.5, 128.9, 130.1, 130.2, 130.5, 130.5, 138.3, 139.2, 156.9, 157.0, 167.6, 167.8, 172.5. (The number of peaks is larger than the number of carbon atoms due to rotamers.)

(ii)(2)-2-Ethoxv-3-(4-{2-[hexyl(2-phenvlethyl)amino]-2-oxoethoxy}pheny)propanoic acid To a solution of ethyl(2S)-2-ethoxy-3-(4-{2-[hexyl(2-phenylethyl)amino]-2-oxoethoxy}phenyl)propanoate (0.081 g, 0.17 mmol) in THF (8.6 mL) was added 4.3 mL of a 0.10 M LiOH solution and the reaction mixture was stirred at room temperature overnight. The reaction mixture was acidified with 2M HCl and extracted with ethyl acetate (3×25 mL). The combined organic phase was washed with brine (25 mL), dried over Na$_2$SO$_4$, and concentrated in vacuo to afford 0.073 g (96%) of a colourless oil.

$^1$HNMR (400 MHz, CDCl3): δ 0.82-0.93 (m, 3H), 1.15 (t, 3H), 1.20-1.35 (m, 6H), 1.47-1.62 (m, 2H), 2.80-2.99 (m, 3H), 3.00-3.09 (m, 1H), 3.11-3.21 and 3.31-3.44 (2m, 3H, rotamers), 3.50-3.67 (m, 3H), 4.01 (m, 1H), 4.40 and 4.66 (2s, 2H, rotamers), 6.75 and 6.85 (2d, 2H, rotamers), 7.10-7.35 (m, 7H), 8.86 (bs, 1H).

$^{13}$C NMR (100 MHz, CDCl3): δ 14.0, 14.1, 15.1, 22.6, 22.6, 26.6, 26.7, 27.3, 28.9, 31.5, 31.6, 33.8, 35.2, 38.1, 46.1, 48.3, 48.4, 49.0, 66.7, 67.4, 79.9, 114.6, 126.4, 127.0, 128.6, 128.9, 130.0, 130.1, 130.6, 130.7, 138.2, 139.1, 156.9, 157.0, 168.1, 168.2, 175.6. (The number of peaks is larger than the number of carbon atoms due to rotamers.)

Example 3

(2S)-3-(4-{2-[(Cyclohexylmethyl)(heptyl)amino]-2-oxoethoxylphenyl)-2-ethoxypropanoic acid (i) Ethyl(2S)-3-{4-[2-(benzyloxy)-2-oxoethoxy]phenyl}-2-ethoxypropanoate To a solution of ethyl(2S)-2-ethoxy-3-(4-hydroxyphenyl) propanoate (23.8 g, 100 mmol, prepared as described in WO99/62872) in acetonitrile (200 mL) was added anhydrous potassium carbonate (31.9 g, 231 mmol) followed by benzyl bromoacetate (17.4 mL, 110 mmol) and the reaction mixture was refluxed overnight. The reaction mixture was allowed to cool to room temperature, insoluble salts were filtered off and the solution was concentrated in vacuo. The residue was taken up in ethyl acetate (300 mL), and the organic phase was washed with aqueous NaHCO$_3$ (3×100 mL) and brine (100 mL), dried over anhydrous MgSO$_4$, and concentrated in vacuo. Purification on silica gel with methylene chloride as the eluent and collection of pure fractions yielded 22.4 g (58%) of a yellow oil.

$^1$H NMR (400 MHz,Cdl3): δ 1.16 (t, 3H), 1.22 (t,3H), 2.93-2.97 (m, 2H), 3.35 (m, 1H), 3.60 (m, 1H), 3.97 (m, 1H), 4.16 (q, 2H), 4.64 (s, 2H), 5.23 (s, 2H), 6.82 (d, 2H), 7.15 (d, 2H), 7.32-7.39 (m,5H).

$^{13}$C NMR (100 MHz, CDCl3): δ 14.3, 15.2, 38.6, 60.9, 65.6, 66.3, 67.0, 80.4, 114.6, 128.5, 128.6, 128.7, 130.6, 135.3, 156.7, 169.0, 172.6.

(ii){4-[(2S)-2,3-Diethoxv-3-oxopropyl]phenoxy}acetic acid

To a solution of ethyl(2S)-3-{4-[2-(benzyloxy)-2-oxoethoxy]phenyl}-2-ethoxypropanoate (22.33 g, 57.8 mmol) in freshly distilled THF (290 mL) was added Pd/C (10%, 3.1 g) and the reaction mixture was hydrogenated under atmospheric pressure at room temperature overnight. The mixture was filtered through a plug of Celite and the filtrate was concentrated in vacuo to afford 16.6 g (97%) of a light yellow oil.

$^1$H NMR (400 MHz,CDCl3): δ 1.15 (t, 3H), 1.21 (t, 3H), 2.93-2.98 (m, 2H), 3.35 (m, 1H), 3.60 (m, 1H), 3.97 (m, 1H), 4.16 (q, 2H), 4.65 (s, 2H), 6.84 (d, 2H), 7.17 (d, 2H), 8.48 (bs, 1H)

$^{13}$C NMR (100 MHz, CDCl$_3$): δ 14.3, 15.1, 38.5, 61.0, 65.1, 66.4, 80.3, 114.6, 130.7, 130.9, 156.4, 172.7, 173.7

(iii) N-(Cyclohexylmethyl)heptanamide

To a solution of aminomethylcyclohexane (0.34 g, 3.0 mmol) in methylene chloride (30 mL) was added heptanoic acid (0.39 g, 3 mmol) and DMAP(0.37 g, 3.0 mmol) followed by 1-ethyl-3-(3-dimethylaminopropyl)carbodiimide hydrochloride (0.57 g, 3.0 mmol) and the reaction mixture was stirred at room temperature overnight. The mixture was diluted with methylene chloride (100 mL), and the organic phase was washed with 5% HCl (3×75 mL), aqueous NaHCO$_3$ (75 mL) and brine (75 mL), and dried over Na$_2$SO$_4$. Concentration in vacuo afforded 0.62 g (92%) of an oil, which then crystallised.

$^1$H NMR (400 MHz,CDCl3): δ 0.84-0.98 (m,5H), 1.08-1.36(m, 8H), 1.44(m, 1H), 1.56-1.78 (m, 8H), 2.16 (t, 2H), 3.09 (t, 2H), 5.45 (bs, 1H).

$^{13}$C NMR (100 MHz, CDCl3): δ 14.1, 22.7, 26.0, 26.6, 29.1, 31.0, 31.7, 37.1, 38.1, 45.8, 173.2.

(iv) N-(Cyclohexylmethyl)-N-heptylamine hydrochloride

N-(Cyclohexylmethyl)heptanamide (0.58 g, 2.6 mmol) was dried once by azeotropic distillation with toluene, taken up in freshly distilled THF (23 mL) and cooled on an icebath under an argon atmosphere. Borane, (3.2 mL of a 2M solution of the methylsulfide complex in diethylether) was added and the icebath was removed after 15 minutes. The reaction mixture was refluxed for four hours and was then allowed to cool to room temperature. 1.2 mL of 10% HCl was carefully added and the mixture was left with stirring overnight.

Concentration in vacuo followed by the addition of ice cold THF (ca. 15 mL) gave a white precipitate. Water (ca. 3 mL) was added followed by toluene (ca. 10 mL) and the mixture was concentrated in vacuo. Ice cold THF (ca. 15 ml) was added to the residue and the resulting precipitate was filtered off and dried in vacuo to give 2.96 g of crude product as a white salt.

This material was used in the subsequent reaction step without any further purification.

$^1$H NMR (400 MHz, CD3OD): δ 0.87-0.98 (m, 3H), 0.97-1.11 (m, 2H), 1.15-1.45 (m, 11H), 1.65-1.86 (m, 8H), 2.84 (d, 2H), 2.93-3.01 (m, 2H).

$^{13}$C NMR (100 MHz, CD3OD): δ 14.3, 23.6, 26.6, 27.0, 27.1, 27.6, 29.9, 31.5, 32.7, 36.4, 55.0.

(v) Ethyl(2S)-3-(4-{2-[(cyclohexylmethyl)(heptyl) amino]-2-oxoethoxy}phenyl)-2-ethoxypropanoate To a solution of {4-[(2S)-2,3-diethoxy-3-oxopropyl]phenoxy} acetic acid (0.108 g, 0.36 mmol) in methylene chloride (3.6 mL) were added N-(cyclohexylmethyl)-N-heptylamine hydrochloride (0.090 g, 0.36 mmol) and DMAP (0.098 g, 0.80 mmol) followed by 1-ethyl-3-(3-dimethylaminopropyl) carbodiimide hydrochloride (0.070 g, 0.36 mmol) and the reaction mixture was stirred at room temperature overnight. The mixture was diluted with methylene chloride (25 mL) and the organic phase was washed with 5% HCl (3×25 mL), aqueous NaHCO$_3$ (25 mL) and brine (25 mL), dried over Na$_2$SO$_4$, and concentrated in vacuo.

Purification on a prepacked column of silica gel (Isolute® SPE Column, 5 g Si/25 mL) with methanol (0-1% gradient) in methylene chloride as the eluent yielded 0.103 g (58%) of a colourless oil.

$^1$H NMR (400 MHz,Cdl3): δ 0.83-0.97(m,5H), 1.11-1.33 (m, 17H), 1.45-1.80 (m, 8H), 2.88-3.00(m, 2H), 3.14 and 3.19 (2d, 2H, rotamers), 3.24-3.39 (m, 3H), 3.58(m, 1H), 3.95(m, 1H), 4.15 (q, 2H), 4.64 and 4.66 (2s, 2H, rotamers), 6.84 and 6.84 (2d, 2H, rotamers), 7.14 (d, 2H)

$^{13}$C NMR (100 MHz,CDCl3): δ 14.2, 14.3, 15.2, 22.7, 26.0, 26.0, 26.5, 26.5, 27.0, 27.0, 27.2, 28.9, 29.1, 31.0, 31.2, 31.9, 36.1, 37.3, 38.6, 46.4, 48.0, 51.7, 53.3, 60.9, 66.3, 67.5, 67.7, 80.4, 114.6, 114.7, 130.2, 130.5, 157.1, 157.1, 167.8, 167.9, 172.6 (The number of peaks is larger than the number of carbon atoms due to rotamers.)

(vi) (2S)-3-(4-{2-[(Cyclohexylmethyl)(heptyl) amino]-2-oxoethoxy}phenyl)-2-ethoxy-propanoic acid To a solution of ethyl(2S)-3-(4-{2-[(cyclohexylmethyl) (heptyl)amino]-2-oxoethoxy}phenyl)-2-ethoxy-propanoate (0.031 g, 0.057 mmol) in THF (2.0 mL) were added water (2.0 mL) and lithium hydroxide (0.006 g, 0.26 mmol), and the reaction mixture was stirred at room temperature overnight. The mixture was acidified with 2M HCl and extracted with ethyl acetate (4×25 mL). The combined organic phase was washed with brine (25 mL), dried over Na$_2$SO$_4$, and concentrated in vacuo to afford 0.027 g (93%) of a colourless oil.

$^1$H NMR (400 MHz,CDCl3): δ 0.82-0.99 (m,5H), 1.10-1.35 (m, 14H), 1.46-1.82 (m, 8H), 2.94 (m, 1H), 3.05 (m,1H), 3.15 and 3.21 (2d, 2H, rotamers), 3.25-3.46 (m, 3H), 3.61 (m, 1H), 4.02 (m,1H), 4.66 and 4.68 (2s, 2H, rotamers), 6.85 (d, 2H), 7.16 (d, 2H), 7.77 (bs, 1H).

$^{13}$C NMR (100 MHz, CDCl3): δ 14.2, 15.1, 22.7, 26.0, 26.0, 26.4, 26.5, 27.0, 27.0, 27.2, 28.9, 29.1, 31.0, 31.2, 31.9, 36.1, 37.2, 38.0, 46.6, 48.0, 51.8, 53.4, 66.8, 67.3, 67.5, 79.9, 114.7, 114.8, 129.9, 130.6, 157.1, 157.2, 168.2, 168.3, 175.2. (The number of peaks is larger than the number of carbon atoms due to rotamers.)

Example 4

(2S)-3-(4-{2-[(2,4-Difluorobenzyl)(heptyl)amino]-2-oxoethoxy}phenyl)-2-ethoxypropanoic acid

(i) N-(2,4-Difluorobenzyl)heptanamide

To a solution of 2,4-difluorbenzylamine (0.43 g, 3.0 mmol) in methylene chloride (30 mL) were added heptanoic acid (0.39 g, 3.0 mmol) and DMAP (0.37 g, 3.0 mmol) followed by 1-ethyl-3-(3-dimethylaminopropyl)carbodiimide hydrochloride (0.58 g, 3.0 mmol) and the reaction mixture was stirred at room temperature overnight. The mixture was diluted with methylene chloride (100 mL), and the organic phase was washed with 5% HCl (3×75 mL), aqueous NaHCO$_3$ (75 mL) and brine (75 mL), and dried over Na$_2$SO$_4$. Concentration in vacuo afforded 0.63 g (82%) of a yellow oil.

$^1$H NMR (400 MHz, CDCl3): δ 0.83-0.91 (m, 3H), 1.22-1.35 (m, 6H), 1.56-1.68 (m, 2H), 2.19 (t, 2H), 4.43 (d, 2H), 5.80 (bs, 1H), 6.75-6.88 (m, 2H), 7.33 (m,1H).

$^{13}$C NMR (100 MHz, Cdl3): δ 14.1, 22.6, 25.7, 29.0, 31.6, 36.8, 37.1, 104.0 (t), 111.5 (dd), 131.5 (dd), 173.2. (Non-protonated carbons not reported.).

(ii) N-(2,4-Difluorobenzyl)-N-heptylamine hydrochloride

N-(2,4-Difluorobenzyl)heptanamide (0.55 g, 2.2 mmol) was dried once by azeotropic distillation with toluene, taken up in freshly distilled THF (19 mL) and cooled on an icebath under an argon atmosphere. Borane, (2.7 mL of a 2M solution of the dimethyl sulfide complex in diethyl ether) was added and the icebath was removed after 15 minutes. The reaction mixture was refluxed for four hours and was then allowed to cool to room temperature. 1.0 mL of 10% HCl was carefully added and the mixture was left with stirring overnight. Concentration in vacuo followed by the addition of ice cold THF (ca. 15 mL) gave a precipitate, which was filtered off and dried in vacuo to afford 0.81 g of crude product as an off-white salt. This material was used in the subsequent reaction step without any further purification.

¹H NMR (400 MHz, CD3OD): δ 0.88-0.95 (m, 3H), 1.27-1.45 (m, 8H), 1.66-1.79 (m, 2H), 3.03-3.10 (m, 2H), 4.27 (s, 2H), 7.06-7.17 (m, 2H), 7.62 (m, 1H).

¹³C NMR (100 MHz, CD3OD): δ 14.3, 23.6, 27.1, 27.5, 29.8, 32.7, 45.0 (d), 48.9, 105.4 (t), 113.3 (dd), 134.8 (dd). (Non-protonated carbons not reported.)

(iii) Ethyl(2S)-3-(4-2-[(2,4-difluorobenzyl)(heptyl)aminol-2-oxoethoxy}phenyl)-2-ethoxypropanoate To a solution of {4-[(2S)-2,3-diethoxy-3-oxopropyl]phenoxy}acetic acid (0.104 g, 0.35 mmol) in methylene chloride (3.5 mL) was added N-(2,4-difluorobenzyl)-N-heptylamine hydrochloride (0.098 g, 0.35 mmol) and DMAP (0.094 g, 0.77 mmol) followed by 1-ethyl-3-(3-dimethylaminopropyl)carbodiimide hydrochloride (0.067 g, 0.35 mmol) and the reaction mixture was stirred at room temperature overnight. The mixture was diluted with methylene chloride (50 mL), and the organic phase was washed with 5% HCl (3×25 mL), aqueous NaHCO₃ (25 mL) and brine (25 mL), dried over Na₂SO₄, and concentrated in vacuo.

Purification on a prepacked column of silica gel(Isolute® SPE Column, 5 g Si/25 mL) with methanol (0-1% gradient) in methylene chloride as the eluent afforded 0.066 g (36%) of a colourless oil.

¹H NMR (400 MHz,CDCl3): δ 0.81-0.90 (m, 3H), 1.15 (t, 3H), 1.17-1.31 (m,11H), 1.43-1.65 (m, 2H), 2.89-3.00 (m, 2H),3.24-3.39 (m,3H), 3.59 (m, 1H), 3.96 (m, 1H), 4.15 (q, 2H), 4.60 (s, 2H), 4.69 and 4.70 (2s, 2H, rotamers), 6.73-6.88 (m, 4H), 7.08-7.22 and 7.22-7.31 (2m, 3H, rotamers).

¹³C NMR (100 MHz, CDCl3): δ 14.1, 14.3, 15.1, 22.6, 26.9, 27.1, 28.7, 29.0, 31.8, 38.5, 41.5, 44.3, 46.1, 47.2, 60.9, 66.3, 67.5, 68.1, 80.3, 103.6 (t), 104.2 (t), 111.6 (dd), 114.4, 114.6, 119.8 (dd), 120.3 (dd), 129.6 (dd), 130.4, 130.6, 131.7 (dd), 156.7, 156.9, 168.2, 168.3, 172.5 (The number of peaks is larger than the number of carbon atoms due to rotamers. Fluorinated carbons not reported.)

(iv) (2S)-3-(4-{2-[(2,4-Difluorobenzel)(heptyl)amino]-2-oxoethoxy}phenyl)-2-ethoxypropanoic acid To a solution of ethyl(2S)-3-(4-{2-[(2,4-difluorobenzyl)(heptyl)amino]-2-oxoethoxy}phenyl)-2-ethoxypropanoate (0.047 g, 0.090 mmol) in THF (2.0 mL) was added water (2.0 mL) and lithium hydroxide (0.010 mg, 0.42 mmol) and the reaction mixture was stirred at room temperature overnight. The reaction mixture was concentrated in vacuo, acidified with 2M HCl, and extracted with ethyl acetate (4×25 mL). The combined organic phase was washed with brine (25 mL), dried over Na₂SO₄, and concentrated in vacuo to afford 0.044 g (89%) of a colourless oil.

¹H NMR (400 MHz,CDCl3): δ 0.83-0.93 (m, 3H), 1.17 (t, 3H), 1.20-1.35 (m, 8H), 1.45-1.67 (m, 2H), 2.90-3.14 (m, 2H), 3.26-3.35 (m, 2H), 3.42 (m,1H), 3.63 (m,1H), 4.04 (m,1H), 4.63 (s, 2H), 4.74 (s, 2H), 6.75-6.90 (m,4H), 7.11-7.22 and 7.25-7.35 (2m, 3H, rotamers), 9.13 (bs, 1H).

¹³C NMR (100 MHz,CDCl3): δ 14.1, 15.1, 22.6, 26.9, 27.1, 28.6, 29.0, 31.8, 38.0, 41.6, 44.3, 46.2, 47.3, 66.8, 67.3, 68.0, 79.8, 103.7 (t), 104.3 (t), 104.3 (t), 111.7 (dd), 114.6, 114.7, 119.7 (dd), 120.1 (dd), 129.7 (m), 130.1, 130.7, 131.8 (dd), 156.8, 157.0, 168.6, 168.7, 175.6 (The number of peaks is larger than the number of carbon atoms due to rotamers. Fluorinated carbons not reported.)

Example 5

(2S)-3-[4-(2-{Butyl[2-fluoro-4-(trifluoromethyl)benzyl]amino}-2-oxoethoxy)phenyl]-2-ethoxy propanoic acid (i) Ethyl(2S)-3-{4-[2-(benzyloxy)-2-oxoethoxy]phenyl}-2-ethoxypropanoate To a solution of ethyl(2S)-2-ethoxy-3-(4-hydroxyphenyl)propanoate (23.8 g, 100 mmol, prepared as described in WO99/62872) in acetonitrile (200 mL) was added anhydrous potassium carbonate (31.9 g, 231 mmol) followed by benzyl bromoacetate (17.4 mL, 110 mmol) and the reaction mixture was refluxed overnight. The reaction mixture was allowed to cool to room temperature, insoluble salts were filtered off and the solution was concentrated in vacuo. The residue was taken up in ethyl acetate (300 mL), and the organic phase was washed with aqueous NaHCO₃ (3×100 mL) and brine (100 mL), dried over anhydrous MgSO₄, and concentrated in vacuo. Purification on silica gel with methylene chloride as the eluent and collection of pure fractions yielded 22.4 g (58%) of a yellow oil.

¹H NMR (400 MHz, CDCl₃): δ 1.16 (t, 3H), 1.22 (t, 3H), 2.93-2.97 (m, 2H), 3.35 (m, 1H), 3.60 (m, 1H), 3.97 (m, 1H), 4.16 (q, 2H), 4.64 (s, 2H), 5.23 (s, 2H), 6.82 (d, 2H), 7.15 (d, 2H), 7.32-7.39 (m, 5H).

¹³C NMR (100 MHz, CDCl₃): δ 14.3, 15.2, 38.6, 60.9, 65.6, 66.3, 67.0, 80.4, 114.6, 128.5, 128.6, 128.7, 130.6, 135.3, 156.7, 169.0, 172.6.

(ii) {4-[(2S)-2,3-Diethoxy-3-oxopropyl]phenoxy}acetic acid

To a solution of ethyl(2S)-3-{4-[2-(benzyloxy)-2-oxoethoxy]phenyl}-2-ethoxypropanoate (22.33 g, 57.8 mmol) in freshly distilled THF (290 mL) was added Pd/C (10%, 3.1 g) and the reaction mixture was hydrogenated under atmospheric pressure at room temperature overnight. The mixture was filtered through a plug of Celite and the filtrate was concentrated in vacuo to afford 16.6 g (97%) of a light yellow oil.

¹H NMR (400 MHz, CDCl₃): δ 1.15 (t, 3H), 1.21 (t, 3H), 2.93-2.98 (m, 2H), 3.35 (m, 1H), 3.60 (m, 1H), 3.97 (m, 1H), 4.16 (q, 2H), 4.65 (s, 2H), 6.84 (d, 2H), 7.17 (d, 2H), 8.48 (bs, 1H)

¹³C NMR (100 MHz, CDCl₃): δ 14.3, 15.1, 38.5, 61.0, 65.1, 66.4, 80.3, 114.6, 130.7, 130.9, 156.4, 172.7, 173.7

(iii) N-Butyl-N-[2-fluoro-4-(trifluoromethyl)benzyl]amine

To a solution of 2-fluoro-4-(trifluoromethyl)benzaldehyde (3.84 g, 20.0 mmol) and n-butylamine (1.46 g, 20.0 mmol) in methanol (100 mL) were added acetic acid (4.6 mL, 80 mmol) and sodium cyanoborohydride (1.51 g, 24.0 mmol) and the solution was stirred at room temperature for 3 days. Water (10 mL) was added and the mixture was concentrated in vacuo. The residue was taken up in aqueous 1 M KOH (125 mL) and ethyl acetate (100 mL) and the phases were separated. The aqueous phase was extracted with ethyl acetate (2×100 mL) and the combined organic phase was dried over Na₂SO₄ and concentrated in vacuo. Purification on a prepacked column of silica gel (Isolute® SPE Column, 70 g/150 mL) with ethyl acetate (33-100% gradient) in heptane as the eluent and collection of pure fractions yielded 1.28 g (26%) of a colourless oil of low viscosity.

$^1$H NMR (400 MHz, CDCl$_3$): δ 0.91 (t, 3H), 1.28-1.41 (m, 2H), 1.44-1.55 (m, 2H), 2.62 (t, 2H), 3.88 (s, 2H), 7.29 (m, 1H), 7.38 (m, 1H), 7.51 (m, 1H).

$^{13}$C NMR (100 MHz, CDCl$_3$): δ 14.1, 20.6, 32.4, 47.0, 49.3, 112.8 (m), 121.1 (m), 123.5 (q), 130.5-131.6 (m), 130.8 (m), 132.0 (d), 160.8 (d).

(iv) Ethyl(2S)-3-[4-(2-{butyl[2-fluoro-4-(trifluoromethyl)benzyl]amino}-2-oxoethoxy)phenyl]-2-ethoxypropanoate To a solution of N-butyl-N-[2-fluoro-4-(trifluoromethyl)benzyl]amine (0.598 g, 2.40 mmol) and {4-[(2S)-2,3-diethoxy-3-oxopropyl]phenoxy}acetic acid (0.593 g, 2.00 mmol) in methylene chloride (20 mL) were added N,N-diisopropylethylamine (0.80 mL, 4.6 mmol) and O-(benzotriazol-1-yl)-N,N,N',N'-tetramethyluronium tetrafluoroborate (0.674 g, 2.10 mmol) and the reaction mixture was stirred at room temperature overnight. The resulting solution was diluted with methylene chloride (100 mL) and the organic phase was washed with 2 M HCl (3×75 mL), saturated aqueous NaHCO$_3$ (2×75 mL), and brine (75 mL), dried over Na$_2$SO$_4$, and concentrated in vacuo. Purification on a prepacked column of silica gel (Isolute® SPE Column, 20 g/70 mL) with methanol (0-2% gradient) in methylene chloride as the eluent yielded 0.785 g (74%) of a pale yellowish-white oil.

$^1$H NMR (400 MHz, CDCl$_3$): δ 0.84-0.97 (m, 3H), 1.11-1.19 (m, 3H), 1.19-1.40 (m, 5H), 1.45-1.65 (m, 2H), 2.90-2.99 (m, 2H), 3.29-3.40 (m, 3H), 3.60 (m, 1H), 3.96 (m, 1H), 4.16 (q, 2H), 4.68 (s, 2H), 4.72 and 4.74 (2s, 2H, rotamers), 6.70 and 6.86 (2d, 2H, rotamers), 7.10 and 7.17 (2d, 2H, rotamers), 7.21-7.40 (m, 3H).

$^{13}$C NMR (100 MHz, CDCl$_3$): δ 13.8, 14.3, 15.2, 20.2, 29.2, 30.9, 38.5, 42.1 (d), 44.6 (d), 46.2, 47.5, 60.9, 66.3, 67.6, 68.3, 80.4, 113.0 (m), 114.3, 114.6, 121.4 (m), 123.3 (q), 128.5 (m), 129.1 (d), 130.6, 130.6, 130.7, 131.0 (d), 131.0-132.2 (m), 156.6, 156.8, 160.3 (d), 160.5 (d), 168.5, 168.6, 172.6. (The number of peaks is larger than the number of carbon atoms due to rotamers.)

(v) (2S)-3-[4-(2-{Butyl[2-fluoro-4-(trifluoromethyl)benzyl]amino}-2-oxoethoxy)phenyl]-2-ethoxypropanoic acid To a solution of ethyl(2S)-3-[4-(2-{butyl[2-fluoro-4-(trifluoromethyl)benzyl]amino}-2-oxoethoxy)phenyl]-2-ethoxypropanoate (0.748 g, 1.42 mmol) in acetonitrile (70 mL) was added aqueous 0.10 M LiOH (35 mL) and the reaction mixture was stirred at room temperature overnight. After neutralisation with 5% HCl, the solvent volume was reduced in vacuo and the remaining aqueous phase was acidified with 5% HCl and extracted with ethyl acetate (3×100 mL). The combined organic phase was washed with brine (100 mL), dried over Na$_2$SO$_4$, and concentrated in vacuo to afford 0.688 g (97%) of a pale yellow oil.

$^1$H NMR (400 MHz, CDCl$_3$): δ0.84-0.96 (m, 3H), 1.16 (t, 3H), 1.21-1.40 (m, 2H), 1.45-1.66 (m, 2H), 2.88-3.11 (m, 2H), 3.29-3.46 (m, 3H), 3.61 (m, 1H), 4.02 (m, 1H), 4.69 (s, 2H), 4.73 and 4.75 (2s, 2H, rotamers), 6.70 an 6.86 (2d, 2H, rotamers), 7.12 and 7.18 (2d, 2H, rotamers), 7.22-7.41 (m, 3H), 8.66 (bs, 1H).

$^{13}$C NMR (100 MHz, CDCl$_3$): δ 13.8, 15.1, 20.1, 29.2, 30.8, 38.0, 42.2 (d), 44.6 (d), 46.3, 47.5, 66.8, 67.4, 68.1, 79.8, 113.0 (m), 114.4, 114.6, 121.4 (m), 123.3 (q), 128.3 (m), 129.1 (d), 130.2, 130.7, 130.8, 131.0 (d), 131.0-132.2 (m), 156.7, 156.9, 160.3 (d), 160.5 (d), 168.8, 168.9, 175.6. (The number of peaks is larger than the number of carbon atoms due to rotamers.)

Example 6

(2S)-3-(4-{2-[(4-Chlorobenzyl)(ethyl)amino]-2-oxoethoxy}phenyl)-2-ethoxypropanoic acid (i) Ethyl(2S)-3-(4-{2-[(4-chlorobenzyl)(ethyl)amino]-2-oxoethoxy}phenyl)-2-ethoxypropanoate To a solution of N-(4-chlorobenzyl)-N-ethylamine (0.150 g, 0.88 mmol) and {4-[(2S)-2,3-diethoxy-3-oxopropyl]phenoxy}acetic acid (0.270 g, 0.91 mmol) in methylene chloride (10 mL) were added N,N-diisopropylethylamine (0.34 mL, 1.9 mmol) and O-(benzotriazol-1-yl)-N,N,N',N'-tetramethyluronium tetrafluoroborate (0.320 g, 1.00 mmol) and the reaction mixture was stirred at room temperature overnight. The resulting solution was diluted with methylene chloride (40 mL) and the organic phase was washed with 5% HCl (50 mL), saturated aqueous NaHCO$_3$ (50 mL), and brine (50 mL), dried over Na$_2$SO$_4$, and concentrated in vacuo. Purification on a prepacked column of silica gel (Isolute® SPE Column, 50 g/150 mL) with methylene chloride/ethyl acetate 10:1 as the eluent yielded 0.24 g (61%) of a colourless oil.

$^1$H NMR (500 MHz, CDCl$_3$): δ 1.05-1.24 (m, 9H), 2.88-3.00 (m, 2H), 3.28-3.42 (m, 3H), 3.60 (m, 1H), 3.96 (m, 1H), 4.12-4.20 (m, 2H), 4.56 and 4.58 (2s, 2H, rotamers), 4.64 and 4.73 (2s, 2H, rotamers), 6.75 and 6.88 (2d, 2H, rotamers), 7.09-7.20 (m, 4H), 7.24 and 7.30 (2d, 2H, rotamers).

(ii) (2S)-3-(4-{2-[(4-Chlorobenzyl)(ethyl)amino]-2-oxoethoxy}phenyl)-2-ethoxypropanoic acid To a solution of ethyl(2S)-3-(4-{2-[(4-chlorobenzyl)(ethyl)amino]-2-oxoethoxy}phenyl)-2-ethoxypropanoate (0.240 g, 0.54 mmol) in THF (30 mL) was added aqueous 0.10 M LiOH (15 mL) and the solution was stirred at room temperature overnight. After neutralisation with 5% HCl, the solvent volume was reduced in vacuo and the remaining aqueous phase was acidified with 5% HCl and extracted with methylene chloride (2×50 mL). The combined organic phase was washed with brine (50 mL), dried over Na$_2$SO$_4$, and concentrated in vacuo. Purification on a prepacked column of silica gel (Isolute® SPE Column, 2 g/15 mL) with ethyl acetate as the eluent afforded 0.138 g (61%) of a pale yellow oil.

$^1$H NMR (500 MHz, CDCl$_3$): δ 1.05-1.21 (m, 6H), 2.94 (m, 1H), 3.04 (m, 1H), 3.30-3.45 (m, 3H), 3.61 (m, 1H), 4.01 (m, 1H), 4.57 and 4.58 (2s, 2H, rotamers), 4.66 and 4.73 (2s, 2H, rotamers), 6.74 and 6.87 (2d, 2H, rotamers), 7.10-7.20 (m, 4H), 7.24 and 7.30 (d, 2H), 7.98 (bs, 1H).

$^{13}$C NMR (100 MHz, CDCl$_3$): δ 12.3, 13.9, 15.1, 38.0, 41.2, 41.5, 47.6, 49.8, 66.7, 67.4, 68.0, 79.8, 114.5, 114.6, 128.3, 128.8, 129.1, 129.5, 130.2, 130.7, 133.3, 133.6, 135.0, 135.7, 156.7, 156.9, 168.4, 168.4, 175.5. (The number of peaks is larger than the number of carbon atoms due to rotamers.)

Example 7

(2S)-2-Ethoxy-3-[4-(2-{ethyl[4-(trifluoromethoxy)benzyl]amino}-2-oxoethoxy)phenyl]-propanoic acid

(i) N-[4-(Trifluoromethoxy)benzyl]acetamide

To a solution of 4-(trifluoromethoxy)benzylamine (3.46 g, 57.6 mmol) in DMF (75 mL) and acetic acid (10.0 g, 52.3 mmol) at −10° C. were added O-(benzotriazol-1-yl)-N,N,N',N'-tetramethyluronium tetrafluoroborate (20.2 g, 62.8 mmol) and N,N-diisopropylethylamine (20.0 mL, 115 mmol) and the reaction mixture was stirred at room temperature overnight. Ethyl acetate (200 mL) was added and the organic phase was washed with water (100 mL), 0.25 M NaOH (100 mL), saturated aqueous NaHCO$_3$ (100 mL), water (100 mL), 0.5 M HCl (100 mL), and water (100 mL), dried over MgSO$_4$, and concentrated in vacuo to afford 11.2 g (92%) of a colourless oil.

$^1$H NMR (600 MHz, CDCl$_3$): δ 2.03 (s, 3H), 4.43 (d, 2H), 5.83 (bs, 1H), 7.17 (d, 2H), 7.31 (d, 2H).

$^{13}$C NMR (125 MHz, CDCl$_3$): δ 22.9, 42.8, 120.5 (q), 121.1, 129.0, 137.3, 148.4, 170.6.

(ii) N-ethyl-N-[4-(Trifluoromethoxy)benzyl]amine

N-[4-(Trifluoromethoxy)benzyl]acetamide (10.4 g, 44.6 mmol) was dissolved in THF (100 mL) and cooled to −10° C. Borane (56 mL of a 2 M solution of the dimethylsulfide complex in diethyl ether) was added and the reaction mixture was stirrred at −10° C. for 15 minuters and was then allowed to warm to room temperature. The reaction mixture was refluxed overnight and was then allowed to cool to room temperature. The reaction was quenched by careful addition of 10% HCl (30 mL) at 0° C. and the mixture was stirred at room temperature overnight and then concentrated in vacuo. The residue was taken up in water (200 mL) and diethyl ether (200 mL) and the phases were separated. Concentration in vacuo of the diethyl ether phase afforded 1.9 g (21%) of the title compound as a colourless oil.

$^1$H NMR (300 MHz, CDCl$_3$): δ 1.28 (t, 3H), 2.72 (q, 2H), 3.83 (s, 2H), 3.86 (bs, 1H), 7.18 (d, 2H), 7.40 (d, 2H).

(iii) Ethyl(2S)-2-ethoxy-3-[4-(2-{ethyl[4-(trifluoromethoxy)benzyl]amino}-2-oxoethoxy)phenyl]propanoate To a solution of N-ethyl-N-[4-(trifluoromethoxy)benzyl]amine (0.438 g, 2.00 mmol) and {4-[(2S)-2,3-diethoxy-3-oxopropyl]phenoxy}acetic acid (0.593 g, 2.00 mmol) in methylene chloride (20 mL) were added N,N-diisopropylethylamine (0.80 mL, 4.6 mmol) and O-(benzotriazol-1-yl)-N,N,N',N'-tetramethyluronium tetrafluoroborate (0.674 g, 2.10 mmol) and the reaction mixture was stirred at room temperature overnight. The resulting solution was diluted with methylene chloride (40 mL) and the organic phase was washed with 5% HCl (50 mL), saturated aqueous NaHCO$_3$ (50 mL), and brine (50 mL), dried over Na$_2$SO$_4$, and concentrated in vacuo. Purification on a prepacked column of silica gel (Isolute® SPE Column, 50 g/150 mL) with methylene chloride/ethyl acetate 10:1 as the eluent yielded 0.57 g (58%) of a colourless oil.

$^1$H NMR (500 MHz, CDCl$_3$): δ 1.08-1.28 (m, 9H), 2.88-3.00 (m, 2H), 3.28-3.44 (m, 3H), 3.60 (m, 1H), 3.96 (m, 1H), 4.12-4.20 (m, 2H), 4.60 and 4.62 (2s, 2H, rotamers), 4.66 and 4.74 (2s, 2H, rotamers), 6.74 and 6.89 (2d, 2H, rotamers), 7.08-7.27 (m, 6H).

$^{13}$C NMR (100 MHz, CDCl$_3$): δ 12.4, 14.0, 14.4, 15.2, 38.6, 41.1, 41.5, 47.5, 49.7, 61.0, 66.3, 67.7, 68.3, 80.4, 114.5, 114.6, 121.2, 121.5, 128.3, 129.5, 130.6, 130.7, 130.7, 135.6, 136.1, 148.6, 156.9, 168.1, 168.2, 172.6. (The number of peaks is larger than the number of carbons due to rotamers. Trifluorinated carbon not reported.)

(iv) (2S)-2-Ethoxy-3-[4-(2-{ethyl[4-(trifluoromethoxy)benzyl]amino}-2-oxoethoxy)phenyl]-propanoic acid To a solution of ethyl(2S)-2-ethoxy-3-[4-(2-{ethyl[4-(trifluoromethoxy)benzyl]amino}-2-oxoethoxy)phenyl]propanoate (0.560 g, 1.13 mmol) in THF (50 mL) was added aqueous 0.10 M LiOH (25 mL) and the solution was stirred at room temperature overnight. After neutralisation with 5% HCl, the solvent volume was reduced in vacuo and the remaining aqueous phase was acidified with 5% HCl and extracted with ethyl acetate (2×50 mL). The combined organic phase was washed with brine (50 mL), dried over Na$_2$SO$_4$, and concentrated in vacuo. Purification on a prepacked column of silica gel (Isolute® SPE Column, 10 g/70 mL) with ethyl acetate as the eluent afforded 0.457 g (87%) of a colourless oil.

$^1$H NMR (500 MHz, CDCl$_3$): δ 1.08-1.23 (m, 6H), 2.96 (m, 1H), 3.08 (m, 1H), 3.33-3.43 (m, 2H), 3.48 (m, 1H), 3.59 (m, 1H), 4.05 (m, 1H), 4.60 and 4.62 (2s, 2H, rotamers), 4.67 and 4.75 (2s, 2H, rotamers), 6.75 and 6.89 (2d, 2H, rotamers), 7.09-7.27 (m, 6H).

$^{13}$C NMR (100 MHz, CDCl$_3$): δ 12.4, 14.0, 15.2, 37.8, 41.2, 41.6, 47.5, 49.7, 67.0, 67.6, 68.2, 79.8, 114.6, 114.8, 121.2, 121.5, 128.3, 129.5, 129.9, 130.8, 130.8, 135.4, 136.0, 148.7, 148.8, 156.9, 157.0, 168.3, 168.3, 174.2. (The number of peaks is larger than the number of carbons due to rotamers. Trifluorinated carbon not reported.)

Example 8

(2S)-2-Ethoxy-3-[4-(2-{ethyl[4-(trifluoromethyl)benzyl]amino}-2-oxoethoxy)phenyl]propanoic acid

(i) Ethyl(2S)-2-ethoxy-3-[4-(2-{ethyl[4-(trifluoromethyl)benzyl]amino}-2-oxoethoxy)phenyl]propanoate To a solution of N-ethyl-N-[4-(trifluoromethyl)benzyl]amine (0.213 g, 1.05 mmol) and {4-[(2S)-2,3-diethoxy-3-oxopropyl]phenoxy}acetic acid (0.296 g, 1.00 mmol) in methylene chloride (10 mL) were added N,N-diisopropylethylamine (0.40 mL, 2.3 mmol) and O-(benzotriazol-1-yl)-N,N,N',N'-tetramethyluronium tetrafluoroborate (0.337 g, 1.05 mmol) and the reaction mixture was stirred at room temperature overnight. The resulting solution was diluted with methylene chloride (90 mL) and the organic phase was washed with 5% HCl (2×50 mL), saturated aqueous NaHCO$_3$ (2×50 mL), and brine (50 mL), dried over Na$_2$SO$_4$, and concentrated in vacuo. Purification on a prepacked column of silica gel (Isolute® SPE Column, 50 g/150 mL) with methanol (0-1% gradient) in methylene chloride as the eluent yielded 0.339 g (70%) of a colourless oil.

$^1$H NMR (400 MHz, CDCl$_3$): δ 1.06-1.24 (m, 9H), 2.88-3.00 (m, 2H), 3.28-3.44 (m, 3H), 3.59 (m, 1H), 3.96 (m, 1H), 4.10-4.19 (m, 2H), 4.64, 4.67, and 4.74 (3s, 4H, rotamers), 6.71 and 6.88 (2d, 2H, rotamers), 7.10 and 7.17 (2d, 2H, rotamers), 7.30 (d, 2H), 7.52 and 7.57 (2d, 2H, rotamers).

$^{13}$C NMR (100 MHz, CDCl$_3$): δ 12.3, 13.9, 14.3, 15.1, 38.5, 41.2, 41.7, 47.8, 49.9, 60.8, 66.2, 67.6, 68.2, 80.3, 114.4, 114.5, 125.5 (m), 125.8 (m), 127.1, 128.2, 129.2-130.6 (m), 130.5, 130.6, 130.6, 141.0, 141.5, 156.6, 156.8, 168.1, 168.2, 172.5. (The number of peaks is larger than the number of carbon atoms due to rotamers. Trifluorinated carbon not reported.)

(ii) (2S)-2-Ethoxy-3-[4-(2-{ethyl[4-(trifluoromethyl) benzyl]amino}-2-oxoethoxy)phenyl]propanoic acid To a solution of ethyl(2S)-2-ethoxy-3-[4-(2-{ethyl[4-(trifluoromethyl)benzyl]amino}-2-oxoethoxy)phenyl]propanoate ((0.308 g, 0.64 mmol) in acetonitrile (32 mL) was added aqueous 0.10 M LiOH (16 mL) and the solution was stirred at room temperature overnight. After neutralisation with 5% HCl, the solvent volume was reduced in vacuo and the remaining aqueous phase was diluted with water and aqueous 0.10 M LiOH (to a total volume of 100 mL, pH~10) and washed with diethyl ether (2×100 mL). The aqueous phase was acidified with 5% HCl and extracted with ethyl acetate (3×100 mL). The combined organic phase was washed with 5% HCl (100 mL) and brine (100 mL), dried over $Na_2SO_4$, and concentrated in vacuo to afford 0.279 g (96%) of a colourless oil.

$^1$H NMR (400 MHz, $CDCl_3$): δ 1.08-1.24 (m, 6H), 2.88-3.12 (m, 2H), 3.34-3.47 (m, 3H), 3.61 (m, 1H), 4.02 (m, 1H), 4.66, 4.67, 4.69, and 4.76 (4s, 4H, rotamers), 6.72 and 6.89 (2d, 2H, rotamers), 7.12 and 7.19 (2d, 2H, rotamers), 7.32 (d, 2H), 7.53 and 7.58 (2d, 2H, rotamers), 8.08 (bs, 1H).

$^{13}$C NMR (100 MHz, $CDCl_3$): δ 12.3, 13.9, 15.1, 38.0, 41.4, 41.9, 48.0, 50.1, 66.8, 67.5, 68.1, 79.8, 114.5, 114.7, 125.6 (m), 125.9 (m), 127.2, 128.2, 129.2-130.6 (m), 130.2, 130.7, 130.8, 140.8, 141.3, 156.7, 156.9, 168.6, 168.6, 175.5. (The number of peaks is larger than the number of carbon atoms due to rotamers. Trifluorinated carbon not reported.)

Example 9

(2S)-3-[4-(2-{Butyl[4-(trifluoromethyl)benzyl] amino}-2-oxoethoxy)phenyl]-2-ethoxypropanoic acid (i) Ethyl(2S)-3-[4-(2-{butyl[4-(trifluoromethyl)benzyl]amino}-2-oxoethoxy)phenyl]-2-ethoxypropanoate To a solution of N-butyl-N-[4-(trifluoromethyl)benzyl] amine (0.486 g, 2.10 mmol) and {4-[(2S)-2,3-diethoxy-3-oxopropyl]phenoxy}acetic acid (0.593 g, 2.00 mmol) in methylene chloride (20 mL) were added N,N-diisopropylethylamine (0.80 mL, 4.6 mmol) and O-(benzotriazol-1-yl)-N,N,N',N'-tetramethyluronium tetrafluoroborate (0.674 g, 2.10 mmol) and the reaction mixture was stirred at room temperature overnight. The resulting solution was diluted with methylene chloride (80 mL) and the organic phase was washed with 5% HCl (3×50 mL), saturated aqueous $NaHCO_3$ (2×50 mL), and brine (50 mL), dried over $Na_2SO_4$, and concentrated in vacuo. Purification on a prepacked column of silica gel (Isolute® SPE Column, 70 g/150 mL) with methanol (0-1% gradient) in methylene chloride as the eluent and collection of pure fractions yielded 0.355 g (35%) of a colourless oil.

$^1$H NMR (400 MHz, $CDCl_3$): δ 0.82-0.93 (m, 3H), 1.09-1.17 (m, 3H), 1.20 (t, 3H), 1.22-1.38 (m, 2H), 1.44-1.61 (m, 2H), 2.87-3.00 (m, 2H), 3.25-3.39 (m, 3H), 3.59 (m, 1H), 3.96 (m, 1H), 4.08-4.18 (m, 2H), 4.64, 4.68, and 4.75 (3s, 4H, rotamers), 6.72 and 6.87 (2d, 2H, rotamers), 7.10 and 7.17 (2d, 2H, rotamers), 7.29 (d, 2H), 7.51 and 7.56 (2d, 2H, rotamers).

$^{13}$C NMR (100 MHz, $CDCl_3$): δ 13.5, 14.0, 14.9, 19.9, 29.0, 30.5, 38.3, 45.9, 46.7, 48.1, 50.1, 60.6, 66.0, 67.3, 67.9, 80.1, 114.2, 114.3, 125.3 (m), 125.6 (m), 126.9, 127.9, 128.8-130.5 (m), 130.2, 130.3, 130.4, 141.0, 141.4, 156.5, 156.7, 168.1, 172.2. (The number of peaks is larger than the number of carbon atoms due to rotamers. Trifluorinated carbon not reported.)

(ii) (2S)-3-[4-(2-{Butyl[4-(trifluoromethyl)benzyl] amino}-2-oxoethoxy)phenyl]-2-ethoxy propanoic acid To a solution of ethyl(2S)-3-[4-(2-{butyl[4-(trifluoromethyl)benzyl]amino}-2-oxoethoxy)phenyl]-2-ethoxypropanoate (0.311 g, 0.61 mmol) in acetonitrile (30 mL) was added aqueous 0.10 M LiOH (15 mL) and the solution was stirred at room temperature overnight. After acidification with 5% HCl, the mixture was extracted with ethyl acetate (3×100 mL) and the combined organic phase was washed with 5% HCl (100 mL) and brine (100 mL), dried over $Na_2SO_4$, and concentrated in vacuo to afford 0.232 g (79%) of a colourless oil.

$^1$H NMR (400 MHz, $CDCl_3$): δ 0.84-0.94 (m, 3H), 1.10-1.19 (m, 3H), 1.20-1.36 (m, 2H), 1.46-1.62 (m, 2H), 2.87-3.10 (m, 2H), 3.25-3.45 (m, 2H), 3.61 (m, 1H), 4.01 (m, 1H), 4.66, 4.69 and 4.76 (3s, 4H, rotamers), 6.72 and 6.88 (2d, 2H, rotamers), 7.12 and 7.19 (2d, 2H, rotamers), 7.30 (d, 2h), 7.53 and 7.59 (2d, 2H, rotamers), 8.27 (bs, 1H).

$^{13}$C NMR (100 MHz, $CDCl_3$): δ 13.8, 15.1, 20.1, 29.2, 30.7, 38.0, 46.3, 47.0, 48.4, 50.4, 66.7, 67.4, 68.1, 79.8, 114.5, 114.6, 125.6 (m), 125.9 (m), 127.1, 128.2, 129.2-130.5 (m), 130.2, 130.7, 130.8, 140.8, 141.2, 156.7, 156.9, 168.8, 175.6. (The number of peaks is larger than the number of carbon atoms due to rotamers. Trifluorinated carbon not reported.)

Example 10

The compounds of Examples 5-9 were tested in the assays described in WO03/051821.

The compounds of formula (IV) generally have an $EC_{50}$ of less than 0.1 μmol/l for PPARα and particular compounds have an $EC_{50}$ of less than 0.01 μmol/l. Additionally in particular compounds the ratio of the $EC_{50}$ (PPARγ): $EC_{50}$ (PPARα) is greater than 150:1. It is believed that this ratio is important with respect to the pharmacological activity of the compounds and to their therapeutic profile.

In addition the compounds of the present invention generally exhibit improved DMPK (Drug Metabolism and Pharmacokinetic) properties for example they exhibit improved metabolic stability in vitro. The compounds also have a promising toxicological profile.

The $EC_{50}$s of the Examples for human PPAR alpha are:

| | |
|---|---|
| Example 5 | 0.001 μmol/l; |
| Example 6 | 0.003 μmol/l; |
| Example 7 | 0.003 μmol/l; |
| Example 8 | 0.005 μmol/l; and |
| Example 9 | 0.003 μmol/l |

Example 11

(2S)-3-(4-{2-]-(2,4-Difluorobenzyl)(octyl)amino]-2-oxoethoxy}phenyl)-2-ethoxypropanoic acid

(i) N-(2,4-Difluorobenzyl)octanamide

To a solution of 2,4-difluorobenzylamine (0.43 g, 3.0 mmol) in methylene chloride (30 mL) were added octanoic acid (0.43 g, 3.0 mmol) and DMAP (0.37 g, 3.0 mmol) followed by 1-ethyl-3-(3-dimethylaminopropyl)carbodiimide hydrochloride (0.60 g, 3.1 mmol) and the reaction mixture was stirred at room temperature overnight. The resulting solution was diluted with methylene chloride (100 mL) and the organic phase was washed with 5% HCl (3×75 mL), aqueous NaHCO$_3$ (75 mL), and brine (75 mL) and dried over anhydrous Na$_2$SO$_4$. Concentration in vacuo afforded 0.78 g (96%) of an oil, which solidified upon standing.

$^1$H NMR (500 MHz, CDCl$_3$): δ 0.81-0.90 (m, 3H), 1.18-1.33 (m, 8H), 1.54-1.66 (m, 2H), 2.12-2.21 (m, 2H), 4.42(d, 2H), 5.82 (bs, 1H), 6.73-6.87 (m, 2H), 7.32 (m, 1H).

(ii) N-(2,4-Difluorobenzyl)-N-octylamine hydrochloride

N-(2,4-Difluorobenzyl)octanamide (0.64 g, 2.4 mmol) was dissolved in freshly distilled THF (20 mL) and cooled on an ice bath under an argon atmosphere. Borane (3.0 mL of a 2 M solution of the dimethylsulfide complex in diethyl ether) was added and the ice bath was removed after 15 minutes. The reaction mixture was refluxed for twenty hours and was then allowed to cool to room temperature. The reaction was quenched by careful addition of 10% HCl (1.2 mL) and the mixture was stirred overnight and then concentrated in vacuo. Addition of ice cold THF (15 mL) afforded a white precipitate, which was filtered off and dried in vacuo to give 0.40 g (58%) of a white salt.

$^1$H NMR (400 MHz, CD$_3$OD): δ 0.85-0.93 (m, 3H), 1.20-1.45 (m, 10H), 1.65-1.89 (m, 2H), 3.01-3.09 (m, 2H), 4.25 (s, 2H), 7.04-7.16 (m, 2H), 7.63 (m, 1H).

(iii) Ethyl(2S)-3-(4-{2-[(2,4-difluorobenzyl)(octyl)amino]-2-oxoethoxy{phenyl)-2-ethoxypropanoate To a solution of {4-[(2S)-2,3-diethoxy-3-oxopropyl]phenoxy}acetic acid (0.120 g, 0.40 mmol) in methylene chloride (5.0 mL) were added N-(2,4-difluorobenzyl)-N-octylamine hydrochloride (0.165 g, 0.57 mmol), DMAP (0.054 g, 0.45 mmol) and N,N-diisopropylethylamine (0.078 mL, 0.45 mmol) followed by 1-ethyl-3-(3-dimethylaminopropyl)carbodiimide hydrochloride (0.085 g, 0.45 mmol) and the reaction mixture was stirred at room temperature overnight. The resulting solution was diluted with methylene chloride (50 mL) and the organic phase was washed with 5% HCl (3×25 mL), aqueous NaHCO$_3$ (25 mL), and brine (25 mL), dried over anhydrous Na$_2$SO$_4$, and concentrated in vacuo. Purification on a prepacked column of silica gel (Isolute® SPE Column, 5 g Si/25 mL) with methanol (0-1% gradient) in methylene chloride as the eluent afforded 0.082 g (38%) of a colourless oil.

$^1$H NMR (400 MHz, CDCl$_3$): δ 0.80-0.90 (m, 3H), 1.14 (t, 3H), 1.17-1.30 (m, 13H), 1.42-1.64 (m, 2H), 2.86-3.00 (m, 2H), 3.20-3.40 (m, 3H), 3.59 (m, 1H), 3.95 (m, 1H), 4.15 (q, 2H), 4.59 (s, 2H), 4.69 and 4.70 (2s, 2H, rotamers), 6.71-6.88 (m, 4H), 7.07-7.18 and 7.20-7.31 (2m, 3H, rotamers).

(iv) (2S)-3-(4-{2-[(2,4-Difluorobenzyl)(octyl)amino]-2-oxoethoxy}phenyl)-2-ethoxypropanoic acid To a solution of ethyl(2S)-3-(4-{2-[(2,4-difluorobenzyl)(octyl)amino]-2-oxoethoxy}phenyl)-2-ethoxypropanoate (0.038 g, 0.071 mmol) in THF (3 mL) was added aqueous 0.10 M LiOH (2 mL) and the reaction mixture was stirred at room temperature overnight. After acidification with 5% HCl, the mixture was extracted with ethyl acetate (3×25 mL) and the combined organic phase was washed with brine (25 mL), dried over anhydrous Na$_2$SO$_4$, and concentrated in vacuo to afford 0.035 g (98%) of a colourless oil.

$^1$H NMR (400 MHz, CDCl$_3$): δ 0.83-0.93 (m, 3H), 1.17 (t, 3H),1.20-1.35 (m, 10H), 1.42-1.68 (m, 2H), 2.88-3.10 (m, 2H), 3.24-3.35 (m, 2H), 3.41 (m, 1H), 3.62 (m, 1H), 4.03 (m, 1H), 4.62 (s, 2H), 4.72 and 4.73 (2s, 2H, rotamers), 6.70-6.90 (m, 4H), 7.09-7.21 and 7.24-7.34 (2m, 3H, rotamers).

Example 12

(2S)-3-(4-{2-[(2,4-Difluorobenzyl)(nonyl)amino]-2-oxoethoxy}phenyl)-2-ethoxypropanoic acid

(i) N-(2,4-Difluorobenzyl)nonanamide

To a solution of 2,4-difluorobenzylamine (0.47 g, 3.3 mmol) in methylene chloride (30 mL) were added nonanoic acid (0.52 g, 3.3 mmol) and DMAP (0.40 g, 3.3 mmol) followed by 1-ethyl-3-(3-dimethylaminopropyl)carbodiimide hydrochloride (0.67 g, 3.5 mmol) and the reaction mixture was stirred at room temperature overnight. The resulting solution was diluted with methylene chloride (100 mL) and the organic phase was washed with 5% HCl (3×75 mL), aqueous NaHCO$_3$ (75 mL), and brine (75 mL) and dried over anhydrous Na$_2$SO$_4$. Concentration in vacuo afforded 0.87 g (93%) of an oil, which solidified upon standing.

$^1$H NMR (600 MHz, CDCl$_3$): δ 0.80-0.86 (m, 3H), 1.16-1.28 (m, 10H), 1.53-1.62 (m, 2H), 2.11-2.17 (m, 2H), 4.37 (d, 2H), 6.12 (bs, 1H), 6.70-6.81 (m, 2H), 7.27 (m, 1H).

(ii) (N-(2,4-Difluorobenzyl)-N-nonylamine hydrochloride

N-(2,4-Difluorobenzyl)nonanamide (0.75 g, 2.6 mmol) was dried once by azeotropic distillation with toluene, dissolved in freshly distilled THF (23 mL), and cooled on an ice bath under an argon atmosphere. Borane (3.3 mL of a 2 M solution of the dimethylsulfide complex in diethyl ether) was added and the ice bath was removed after 15 minutes. The reaction mixture was refluxed for five hours and was then allowed to cool to room temperature. The reaction was quenched by careful addition of 10% HCl (1.3 mL) and the mixture was stirred for three hours and then concentrated in vacuo. Addition of ice cold THF (15 mL) afforded a white precipitate, which was filtered off and dried in vacuo to give 0.69 g (85%) of a white salt.

$^1$H NMR (400 MHz, CD$_3$OD): δ 0.85-0.94 (m, 3H), 1.20-1.45 (m, 12H), 1.65-1.80 (m, 2H), 3.00-3.10 (m, 2H), 4.26 (s, 2H), 7.04-7.16 (m, 2H), 7.64 (m, 1H).

(iii) Ethyl(2S)-3-(4-{2-[(2,4-difluorobenzyl)(nonyl)amino]-2-oxoethoxy}phenyl)-2-ethoxypropanoate To a solution of {4-[(2S)-2,3-diethoxy-3-oxopropyl]phenoxy}acetic acid (0.120 g, 0.40 mmol) in methylene chloride (5.0 mL) were added (N-(2,4-difluorobenzyl)-N-nonylamine hydrochloride (0.173 g, 0.57 mmol), DMAP (0.058 g, 0.45 mmol), and N,N-diisopropylethylamine (0.078 mL, 0.45 mmol) followed by 1-ethyl-3-(3-dimethylaminopropyl)carbodiimide hydrochloride (0.085 g, 0.45 mmol) and the reaction mixture was stirred at room temperature overnight. The resulting solution was diluted with methylene chloride (50 mL) and the organic phase was washed with 5% HCl (3×25 mL), aqueous NaHCO$_3$ (25 mL), and brine (25 mL), dried over anhydrous Na$_2$SO$_4$, and concentrated in vacuo. Purification on a prepacked column of silica gel (Isolute® SPE Column, 5 g Si/25 mL) with methanol (0-1% gradient) in methylene chloride as the eluent afforded 0.117 g (53%) of a colourless oil.

$^1$H NMR (400 MHz, CDCl$_3$): δ 0.82-0.90 (m, 3H), 1.14 (t, 3H), 1.17-1.30 (m, 15H), 1.42-1.62 (m, 2H), 2.88-3.00 (m, 2H), 3.23-3.38 (m, 3H), 3.58 (m, 1H), 3.95 (m, 1H), 4.14 (q, 2H), 4.59 (s, 2H), 4.68 and 4.69 (2s, 2H, rotamers), 6.70-6.90 (m, 4H), 7.06-7.18 and 7.20-7.31 (2m, 3H, rotamers).

(iv) (2S)-3-(4-{2-[(2,4-Difluorobenzyl)(nonyl) amino]-2-oxoethoxy}phenyl)-2-ethoxypropanoic acid To a solution of ethyl(2S)-3-(4-{2-[(2,4-difluorobenzyl)(nonyl)amino]-2-oxoethoxy}phenyl)-2-ethoxypropanoate (0.038 g, 0.070 mmol) in THF (3 mL) was added aqueous 0.10 M LiOH (2 mL) and the reaction mixture was stirred at room temperature overnight. After acidification with 5% HCl, the mixture was extracted with ethyl acetate (3×25 mL) and the combined organic phase was washed with brine (25 mL), dried over anhydrous Na$_2$SO$_4$, and concentrated in vacuo to afford 0.034 g (94%) of a colourless oil.

$^1$H NMR (400 MHz, CDCl$_3$): δ 0.83-0.93 (m, 3H), 1.17 (t, 3H), 1.20-1.35 (m, 12H), 1.44-1.66 (m, 2H), 2.90-3.10 (m, 2H), 3.25-3.34 (m, 2H), 3.42 (m, 1H), 3.62 (m, 1H), 4.04 (m, 1H), 4.62 (s, 2H), 4.72 and 4.73 (2s, 2H, rotamers), 6.73-6.90 (m, 4H), 7.09-7.21 and 7.24-7.34 (2m, 3H, rotamers).

Example 13

(2S)-3-(4-{2-[(2,4-Difluorobenzyl)(4-ethylbenzyl) amino]-2-oxoethoxy}phenyl)-2-ethoxypropanoic acid (i) N-(2,4-Difluorobenzyl)-4-ethylbenzamide To a solution of 2,4-difluorobenzylamine (3.58 g, 25.0 mmol) in methylene chloride (250 mL) were added 4-ethylbenzoic acid (3.94 g, 26.3 mmol) and DMAP (3.36 g, 27.5 mmol) followed by 1-ethyl-3-(3-dimethylaminopropyl)carbodiimide hydrochloride (5.27 g, 27.5 mmol) and the reaction mixture was stirred at room temperature overnight. The resulting solution was washed with 5% HCl (3×100 mL), saturated aqueous NaHCO$_3$ (100 mL), and brine (100 mL) and dried over Na$_2$SO$_4$. Concentration in vacuo afforded 6.49 g (94%) of white solid.

$^1$H NMR (400 MHz, CDCl$_3$): δ 1.24 (t, 3H), 2.69 (q, 2H), 4.64 (d, 2H), 6.45 (bs, 1H), 6.77-6.90 (m, 2H), 7.25 (d, 2H), 7.41 (m, 1H), 7.69 (d, 2H).

(ii) N-(2,4-Difluorobenzyl)-N-(4-ethylbenzyl)amine

N-(2,4-Difluorobenzyl)-4-ethylbenzamide (6.20 g, 22.5 mmol) was dissolved in freshly distilled THF (220 mL) and cooled in an ice bath under an argon atmosphere. Borane (28 mL of a 2 M solution of the dimethylsulfide complex in diethyl ether) was added and the ice bath was removed after 15 minutes. The reaction mixture was refluxed overnight and was then allowed to cool to room temperature. The reaction was quenched at 0° C. by careful addition of 10% HCl (11 mL) and the mixture was stirred at room temperature for three hours and then concentrated in vacuo. The residue was taken up in ethyl acetate (200 mL) and aqueous 2 M K$_2$CO$_3$ (200 mL) and the phases were separated. The aqueous phase was extracted with ethyl acetate (2×200 mL) and the combined organic phase was washed with brine (100 mL), dried over Na$_2$SO$_4$, and concentrated in vacuo to afford 5.56 g (94%) of a yellow oil.

$^1$H NMR (400 MHz, CDCl$_3$): δ 1.24 (t, 3H), 2.65 (q, 2H), 3.77 (s, 2H), 3.82 (s, 2H), 6.75-6.90 (m, 2H), 7.17 (d, 2H), 7.25 (d, 2H), 7.34 (m, 1H).

(iii) Ethyl(2S)-3-(4-{2-[(2,4-difluorobenzyl)(4-ethylbenzyl)amino]-2-oxoethoxy}phenyl)-2-ethoxypropanoate To a solution of {4-[(2S)-2,3-diethoxy-3-oxopropyl]phenoxy}acetic acid (1.48 g, 5.0 mmol) and N-(2,4-difluorobenzyl)-N-(4-ethylbenzyl)amine (1.57 g, 6.0 mmol) in methylene chloride (50 mL) at 0° C. were added N,N-diisopropylethylamine (2.0 mL, 11.5 mmol) followed by O-(benzotriazol-1-yl)-N,N,N',N'-tetramethyluronium tetrafluoroborate (1.93 g, 6.0 mmol) and the reaction mixture was stirred overnight and then concentrated in vacuo. The residue was taken up in ethyl acetate (200 mL) and the organic phase was washed with 5% HCl (3×100 mL), saturated aqueous NaHCO$_3$ (100 mL), and brine (100 mL), dried over Na$_2$SO$_4$, and concentrated in vacuo. Purification on silica gel (240 g) with methanol (0-4% gradient) in methylene chloride as the eluent and collection of pure fractions afforded 1.18 g (44%) of a colourless oil.

$^1$H NMR (400 MHz, CDCl$_3$): δ 1.16 (t, 3H), 1.19-1.27 (m, 6H), 2.57-2.70 (m, 2H), 2.90-3.00 (m, 2H), 3.35 (m, 1H), 3.60 (m, 1H), 3.96 (m, 1H), 4.16 (q, 2H), 4.52, 4.54, 4.56 and 4.59 (4s, 4H, rotamers), 4.74 and 4.80 (2s, 2H, rotamers), 6.69-6.88 (m, 4H), 7.02-7.22 and 7.25-7.36 (2m, 7H, rotamers).

(iv) (2S)-3-(4-{2-[(2,4-Difluorobenzyl)(4-ethylbenzyl)amino]-2-oxoethoxy}phenyl)-2-ethoxypropanoic acid To a solution of ethyl(2S)-3-(4-{2-[(2,4-difluorobenzyl)(4-ethylbenzyl)amino]-2-oxoethoxy}phenyl)-2-ethoxypropanoate (1.13 g, 2.1 mmol) in acetonitrile (100 mL) was added aqueous 0.10 M LiOH (52 mL) and the solution was stirred at room temperature overnight. After neutralisation with 5% HCl, the solvent volume was reduced in vacuo and the remaining aqueous phase was acidified with 5% HCl and extracted with ethyl acetate (3×100 mL). The combined organic phase was washed with brine (100 mL), dried over Na$_2$SO$_4$, and concentrated in vacuo to afford 1.01 g (94%) of a colourless oil.

$^1$H NMR (400 MHz, CDCl$_3$): δ 1.16 (t, 3H), 1.19-1.28 (m, 3H), 2.56-2.71 (m, 2H), 2.95 (m, 1H), 3.05 (m, 1H), 3.41 (m, 1H), 3.61 (m, 1H), 4.02 (m, 1H), 4.52, 4.54, 4.55 and 4.59 (4s, 4H, rotamers), 4.75 and 4.81 (2s, 2H, rotamers), 6.70-6.88 (m, 4H), 7.04-7.22 and 7.25-7.35 (2m, 7H, rotamers), 8.04 (bs, 1H).

Example 14

(2S)-3-(4-{2-[Benzyl(methyl)amino]-2-oxoethoxy}phenyl)-2-ethoxypropanoic acid

(i)Ethyl(2S)-3-(4-{2-[benzyl(methyl)amino]-2-oxoethoxy}phenyl)-2-ethoxypropanoate To a solution of {4-[(2S)-2,3-diethoxy-3-oxopropyl]phenoxy}acetic acid (0.320 g, 1.08 mmol) in methylene chloride (10 mL) were added N-methylbenzylamine (0.145 g, 1.20 mmol) and O-(benzotriazol-1-yl)-N,N,N',N'-tetramethyluronium tetrafluoroborate (0.353 g, 1.10 mmol) and the reaction mixture was stirred at room temperature for three days. The resulting solution was diluted with methylene chloride (100 mL) and the organic phase was washed with 5% HCl (3×50 mL), aqueous $NaHCO_3$ (50 mL) and brine (50 mL), dried over anhydrous $Na_2SO_4$, and concentrated in vacuo. Purification on a prepacked column of silica gel (Isolute® SPE Column, 10 g Si/70 mL) with methanol (0-1% gradient) in methylene chloride as the eluent afforded 0.186 g (43%) of a colourless oil.

$^1$H NMR (400 MHz, $CDCl_3$): δ 1.10-1.24 (m, 6H), 2.88-2.99 (m, 2H), 2.91 and 2.95 (2s, 3H, rotamers), 3.33 (m, 1H), 3.58 (m, 1H), 3.95 (m, 1H), 4.08-4.20 (m, 2H), 4.57 and 4.59 (2s, 2H, rotamers), 4.69 and 4.70 (2s, 2H, rotamers), 6.77 and 6.87 (2d, 2H, rotamers), 7.07-7.38 (m, 7H).

(ii)(2S)-3-(4-{2-[Benzyl(methyl)amino]-2-oxoethoxy}phenyl)-2-ethoxypropanoic acid To a solution of ethyl(2S)-3-(4-{2-[benzyl(methyl)amino]-2-oxoethoxy}phenyl)-2-ethoxypropanoate (0.155 g, 0.39 mmol) in THF (20 mL) was added aqueous 0.10 M LiOH (10 mL) and the reaction mixture was stirred overnight. After acidification with 5% HCl, the mixture was extracted with ethyl acetate (3×50 mL) and the combined organic phase was washed with brine (50 mL), dried over anhydrous $Na_2SO_4$, and concentrated in vacuo to afford 0.139 g (97%) of a colourless oil.

$^1$H NMR (400 MHz, $CDCl_3$): δ 1.10-1.20 (m, 3H), 2.86-3.10 (m, 2H), 2.94 and 2.97 (2s, 3H, rotamers), 3.38 (m, 1H), 3.61 (m, 1H), 4.01 (m, 1H), 4.59 and 4.61 (2s, 2H, rotamers), 4.72 and 4.73 (2s, 2H, rotamers), 6.78 and 6.87 (2d, 2H, rotamers), 7.10-7.40 (m, 7H), 8.97 (bs, 1H).

Example 15

(2S)-2-Ethoxy-3-[4-(2-{heptyl[(1-methylindol-2-yl)methyl]amino}-2-oxoethoxy)phenyl]propanoic acid

(i) N-heptyl-N-[(1-methylindol-2-yl)methyl]amine

To a solution of 1-methylindole-2-carbaldehyde (1.59 g, 10.0 mmol) and heptylamine (1.49 mL, 10.0 mmol) in ethanol (50 mL) were added acetic acid (2.3 mL, 40 mmol) and sodium cyanoborohydride (0.75 g, 12.0 mmol) and the reaction mixture was stirred at room temperature overnight. Water (5 mL) was added and the mixture was concentrated in vacuo. The residue was taken up in ethyl acetate (75 mL) and aqueous 1 M KOH (75 mL) and the phases were separated. The aqueous layer was extracted with ethyl acetate (2×75 mL) and the combined organic phase was washed with brine (75 mL), dried over $Na_2SO_4$, and concentrated in vacuo. Purification on a column of silica gel (130 g) with ethyl acetate (17-33% gradient) in heptane as the eluent yielded 1.57 g (61%) of a yellow oil, which solidified upon standing.

$^1$H NMR (400 MHz, $CDCl_3$): δ 0.87-0.95 (m, 3H), 1.20-1.40 (m, 8H), 1.46-1.60 (m, 2H), 2.70 (t, 3H), 3.78 (s, 3H), 3.94 (s, 2H), 6.39 (s, 1H), 7.09 (m, 1H), 7.20 (m, 1H), 7.31 (d, 1H), 7.58 (d, 1H).

(ii)Ethyl(2S)-2-ethoxy-3-[4-(2-{heptyl[(1-methylindol-2-yl)methyl]amino}-2-oxoethoxy)phenyl]propanoate To a solution of {4-[(2S)-2,3-diethoxy-3-oxopropyl]phenoxy}acetic acid (0.889 g, 3.00 mmol) and N-heptyl-N-[(1-methylindol-2-yl)methyl]amine (0.814 g, 3.15 mmol) in methylene chloride (30 mL) were added DMAP (0.403 g, 3.30 mmol) and 1-ethyl-3-(3-dimethylaminopropyl)carbodiimide hydrochloride (0.633 g, 3.30 mmol) and the reaction mixture was stirred at room temperature for three days. The mixture was diluted with methylene chloride (100 mL) and the organic phase was washed with 2 M HCl (3×100 mL), saturated aqueous $NaHCO_3$ (100 mL), and brine (100 mL), dried over $Na_2SO_4$, and concentrated in vacuo. Purification on a column of silica gel (100 g) with methanol (0-5% gradient) in methylene chloride as the eluent yielded 0.71 g (43%) of a pale yellow oil.

$^1$H NMR (400 MHz, $CDCl_3$): δ 0.82-0.93 (m, 3H), 1.18 (t, 3H), 1.14-1.36 (m, 11H), 1.47-1.62 (m, 2H), 2.91-3.03 (m, 2H), 3.20-3.29 and 3.30-3.47 (2m, 3H, rotamers), 3.58 (s, 3H), 3.61 (m, 1H), 3.98 (m, 1H), 4.18 (q, 2H), 4.73 (s, 2H), 4.86 (s, 2H), 6.44 (s, 1H), 6.87 (d, 2H), 7.06-7.34 (m, 5H), 7.57 (d, 1H).

(iii)(2S)-2-Ethoxy-3-[4-(2-{heptyl[(1-methylindol-2-yl)methyl]amino}-2-oxoethoxy)phenyl]propanoic acid To a solution of ethyl(2S)-2-ethoxy-3-[4-(2-{heptyl[(1-methylindol-2-yl)methyl]amino}-2-oxoethoxy)phenyl]propanoate (0.655 g, 1.22 mmol) in THF (60 mL) was added aqueous 0.10 M LiOH (30 mL) and the reaction mixture was stirred at room temperature overnight. After acidification with 2 M HCl, the mixture was extracted with ethyl acetate (3×75 mL) and the combined organic phase was washed with brine (75 mL), dried over $Na_2SO_4$, and concentrated in vacuo to afford 0.61 g (95%) of a pale yellow oil.

$^1$H NMR (400 MHz, $CDCl_3$): δ 0.80-0.93 (m, 3H), 1.13-1.34 (m, 11H), 1.46-1.62 (m, 2H), 2.97 and 3.10 (AB part of ABX system, 2H), 3.19-3.29 and 3.38-3.55 (2m, 3H, rotamers), 3.58 (s, 3H), 3.59 (m, 1H), 4.07 (m, 1H), 4.73 (s, 2H), 4.86 (s, 2H), 6.43 (s, 1H), 6.88 (d, 2H), 7.05-7.33 (m, 5H), 7.56 (d, 1H).

Example 16

(2S)-3-(4-{2-](2,3-Dimethoxybenzyl)(heptyl)amino]-2-oxoethoxy}phenyl)-2-ethoxypropanoic acid

(i) N-Heptyl-2,3-dimethoxybenzamide

To a solution of 2,3-dimethoxybenzoic acid (4.55 g, 25.0 mmol) in methylene chloride (250 mL) were added heptylamine (2.78 g, 27.5 mmol) and DMAP (3.36 g, 27.5 mmol) followed by 1-ethyl-3-(3-dimethylaminopropyl)carbodiimide hydrochloride (5.27 g, 27.5 mmol) and the reaction mixture was stirred at room temperature overnight. The resulting solution was washed with 5% HCl (3×100 mL), saturated aqueous $NaHCO_3$ (100 mL), and brine (100 mL) and dried over $MgSO_4$. Concentration in vacuo afforded 6.81 g (98%) of a colourless oil.

¹H NMR (400 MHz, CDCl₃): δ 0.82-0.91 (m, 3H), 1.20-1.43 (m, 8H), 1.53-1.66 (m, 2H), 3.40-3.48 (m, 2H), 3.87 (s, 3H), 3.88 (s, 3H), 7.02 (dd, 1H), 7.13 (t, 1H), 7.67 (dd, 1H), 7.93 (bs, 1H).

(ii) N-(2,3-Dimethoxybenzyl)-N-heptylamine

N-Heptyl-2,3-dimethoxybenzamide (6.47 g, 23.2 mmol) was dissolved in freshly distilled THF (230 mL) and cooled in an ice bath under an argon atmosphere. Borane (29 mL of a 2 M solution of the dimethylsulfide complex in diethyl ether) was added and the ice bath was removed after 15 minutes. The reaction mixture was refluxed overnight and was then allowed to cool to room temperature. The reaction was quenched by careful addition of 10% HCl (11 mL) and the mixture was stirred for four hours and then concentrated in vacuo. The residue was taken up in ethyl acetate (300 mL) and washed with aqueous 2 M K₂CO₃ (3×100 mL) and brine (100 mL), dried over Na₂SO₄, and concentrated in vacuo. Purification on silica gel (160 g) with ethyl acetate (33-100% gradient) in heptane and finally 5% ethanol in ethyl acetate as the eluent yielded 3.40 g (55%) of a light yellow oil.

¹H NMR (400 MHz, CDCl₃): δ 0.83-0.91 (m, 3H), 1.20-1.35 (m, 8H), 1.42-1.54 (m, 2H), 2.54-2.61 (m, 2H), 3.79 (s, 2H), 3.85 (s, 3H), 3.86 (s, 3H), 6.83 (d, 1H), 6.88 (d, 1H), 7.01 (t, 1H).

(iii) Ethyl(2S)-3-(4-{2-[(2,3-dimethoxybenzyl)(heptyl)amino]-2-oxoethoxy}phenyl)-2-ethoxypropanoate To a solution of N-(2,3-dimethoxybenzyl)-N-heptylamine (1.46 g, 5.5 mmol) and {4-[(2S)-2,3-diethoxy-3-oxopropyl]phenoxy}acetic acid (1.48 g, 5.0 mmol) in methylene chloride (50 mL) at 0° C. were added N,N-diisopropylethylamine (2.0 mL, 11.5 mmol) and O-(benzotriazol-1-yl)-N,N,N',N'-tetramethyluronium tetrafluoroborate (1.93 g, 6.0 mmol) and the reaction mixture was stirred at room temperature overnight and then concentrated in vacuo. The residue was taken up in ethyl acetate (200 mL) and the organic phase was washed with saturated aqueous NaHCO₃ (3×100 mL), 5% HCl (3×100 mL), and brine (100 mL), dried over Na₂SO₄, and concentrated in vacuo. Purification on silica gel (100 g) with methanol (0-2% gradient) in methylene chloride as the eluent and collection of pure fractions yielded 1.57 g (58%) of a pale yellow oil.

¹H NMR (400 MHz, CDCl₃): δ 0.82-0.90 (m, 3H), 1.11-1.30 (m, 14H), 1.46-1.64 (m, 2H), 2.89-2.98 (m, 2H), 3.20-3.28 and 3.28-3.40 (2m, 3H, rotamers), 3.59 (m, 1H), 3.81, 3.82, 3.85 and 3.87 (4s, 6H, rotamers), 3.95 (m,1H), 4.11-4.20 (m, 2H), 4.59, 4.69, 4.70 and 4.72 (4s, 4H, rotamers), 6.69-6.91 (m, 4H), 6.95 and 7.02 (2t, 1H, rotamers), 7.11 and 7.16 (2d, 2H, rotamers).

(iv) (2S)-3-(4-{2-[(2,3-Dimethoxybenzyl)(heptyl)amino]-2-oxoethoxy}phenyl)-2-ethoxypropanoic acid To a solution of ethyl(2S)-3-(4-{2-[(2,3-dimethoxybenzyl)(heptyl)amino]-2-oxoethoxy}phenyl)-2-ethoxypropanoate (1.40 g, 2.55 mmol) in acetonitrile (100 mL) was added aqueous 0.10 M LiOH (50 mL) and the reaction mixture was stirred at room temperature overnight. The solvent volume was reduced in vacuo and the remaining aqueous phase was acidified with 5% HCl and extracted with ethyl acetate (3×100 mL). The combined organic phase was washed with brine (75 mL), dried over Na₂SO₄, and concentrated in vacuo to afford 1.29 g (98%) of a pale yellow oil.

¹H NMR (400 MHz, CDCl₃): δ 0.81-0.91 (m, 3H), 1.13-1.32 (m, 11H), 1.46-1.64 (m, 2H), 2.94 (m, 1H), 3.07 (m, 1H), 3.25 and 3.34 (2m, 2H, rotamers), 3.44 (m, 1H), 3.59 (m, 1H), 3.82 (s, 3H), 3.86 and 3.88 (2s, 3H, rotamers), 4.03 (m,1H), 4.60, 4.70, 4.72 and 4.74 (4s, 4H, rotamers), 6.70-6.92 (m, 4H), 6.96 and 7.03 (2t, 1H, rotamers), 7.12 and 7.17 (2d, 2H, rotamers).

Example 17

(2S)-3-(4-{2-[Butyl(2,3-dimethoxybenzyl)amino]-2-oxoethoxy}phenyl)-2-ethoxypropanoic acid (i) N-Butyl-2,3-dimethoxybenzamide To a solution of 2,3-dimethoxybenzoic acid (4.55 g, 25.0 mmol) in metylene chloride (250 mL) were added butylamine (2.01 g, 27.5 mmol) and DMAP (3.36 g, 27.5 mmol) followed by 1-ethyl-3-(3-dimethylaminopropyl)carbodiimide hydrochloride (5.27 g, 27.5 mmol) and the reaction mixture was stirred at room temperature overnight. The resulting solution was washed with 5% HCl (3×100 mL), saturated aqueous NaHCO₃ (100 mL), and brine (100 mL) and dried over MgSO₄. Concentration in vacuo afforded 5.59 g (94%) of a colourless oil.

¹H NMR (400 MHz, CDCl₃): δ 0.94 (t, 3H), 1.35-1.47 (m, 2H), 1.53-1.63 (m, 2H), 3.40-3.48 (m, 2H), 3.86 (s, 3H), 3.87 (s, 3H), 7.00 (dd, 1H), 7.11 (t, 1H), 7.66 (dd, 1H), 7.92 (bs, 1H).

(ii) N-Butyl-N-(2,3-dimethoxybenzyl)amine

N-Butyl-2,3-dimethoxybenzamide (5.37 g, 22.6 mmol) was dissolved in freshly distilled THF (230 mL) and cooled in an ice bath under an argon atmosphere. Borane (28 mL of a 2 M solution of the dimethylsulfide complex in diethyl ether) was added and the ice bath was removed after 15 minutes. The reaction mixture was refluxed overnight and was then allowed to cool to room temperature. The reaction was quenched by careful addition of 10% HCl (11 mL) and the mixture was stirred for four hours and then concentrated in vacuo. The residue was taken up in ethyl acetate (300 mL) and washed with aqueous 2 M K₂CO₃ (3×100 mL), and brine (100 mL), dried over Na₂SO₄, and concentrated in vacuo. Purification on silica gel (160 g) with ethyl acetate (33-100% gradient) in heptane and finally 5% ethanol in ethyl acetate as the eluent yielded 2.74 g (54%) of a light yellow oil.

¹H NMR (400 MHz, CDCl₃): δ 0.89 (t, 3H), 1.26-1.40 (m, 2H), 1.42-1.53 (m, 2H), 2.56-2.63 (m, 2H), 3.79 (s, 2H), 3.85 (s, 3H), 3.86 (s, 3H), 6.83 (dd, 1H), 6.89 (dd, 1H), 7.01 (t, 1H).

(iii) Ethyl(2S)-3-(4-{2-[butyl(2,3-dimethoxybenzyl)amino]-2-oxoethoxy}phenyl)-2-ethoxypropanoate To a solution of N-butyl-N-(2,3-dimethoxybenzyl)amine (1.23 g, 5.5 mmol) and {4-[(2S)-2,3-diethoxy-3-oxopropyl]phenoxy}acetic acid (1.48 g, 5.0 mmol) in methylene chloride (50 mL) at 0° C. were added N,N-diisopropylethylamine (2.0 mL, 11.5 mmol) followed by O-(benzotriazol-1-yl)-N,N,N',N'-tetramethyluronium tetrafluoroborate (1.93 g, 6.0 mmol) and the reaction mixture was stirred overnight and then concentrated in vacuo. The residue was taken up in ethyl acetate (200 mL) and the organic phase was washed with saturated aqueous NaHCO₃ (3×100 mL), 5% HCl (3×100 mL), and brine (100 mL), dried over Na₂SO₄, and concentrated in vacuo. Purification on silica gel (120 g) with methanol (0-2% gradient) in methylene chloride as the eluent and collection of pure fractions afforded 1.07 g (43%) of a pale yellow oil.

$^1$H NMR (400 MHz, CDCl$_3$): δ 0.84-0.94 (m, 3H), 1.12-1.19 (m, 3H), 1.19-1.35 (m, 5H), 1.46-1.64 (m, 2H), 2.88-3.00 (m, 2H), 3.21-3.29 and 3.29-3.40 (2m, 3H, rotamers), 3.59 (m, 1H), 3.82, 3.82, 3.86 and 3.88 (4s, 6H, rotamers), 3.96 (m,1H), 4.11-4.21 (m, 2H), 4.60, 4.70, 4.71 and 4.73 (4s, 4H, rotamers), 6.69-6.92 (m, 4H), 6.96 and 7.03 (2t, 1H, rotamers), 7.12 and 7.16 (2d, 2H, rotamers).

(iv) (2S)-3-(4-{2-]Butyl(2,3-dimethoxybenzyl)amino]-2-oxoethoxy}phenyl)-2-ethoxypropanoic acid To a solution of ethyl(2S)-3-(4-{2-[(2,3-dimethoxybenzyl)(butyl)amino]-2-oxoethoxy}phenyl)-2-ethoxypropanoate (1.02 g, 2.0 mmol) in acetonitrile (80 mL) was added aqueous 0.10 M LiOH (40 mL) and the reaction mixture was stirred at room temperature overnight. The solvent volume was reduced in vacuo and the remaining aqueous phase was acidified with 5% HCl and extracted with ethyl acetate (3×100 mL). The combined organic phase was washed with brine (75 mL), dried over Na$_2$SO$_4$, and concentrated in vacuo to afford 0.96 g (98%) of a light yellow oil.

$^1$H NMR (400 MHz, CDCl$_3$): δ 0.84-0.94 (m, 3H), 1.12-1.20 (m, 3H), 1.20-1.36 (m, 2H), 1.45-1.64 (m, 2H), 2.94 (m, 1H), 3.06 (m, 1H), 3.26 and 3.35 (2m, 2H, rotamers), 3.43 (m, 1H), 3.59 (m, 1H), 3.82 and 3.82 (2s, 3H, rotamers), 3.86 and 3.88 (2s, 3H, rotamers), 4.03 (m, 1H), 4.60, 4.70, 4.72 and 4.74 (4s, 4H, rotamers), 6.70-6.92 (m, 4H), 6.96 and 7.03 (2t, 1H, rotamers), 7.12 and 7.17 (2d, 2H, rotamers).

Example 18

(2S)-3-(4-{2-[(4-Chlorobenzyl)(4-isopropylbenzyl)amino]-2-oxoethoxy}phenyl)-2-ethoxypropanoic acid (i) N-(4-Chlorobenzyl)-N-(4-isopropylbenzyl)amine To a solution of 4-chlorobenzylamine (2.83 g, 20.0 mmol) and 4-isopropylbenzaldehyde (2.96 g, 20.0 mmol) in methanol (100 mL) were added acetic acid (4.6 mL, 80 mmol) and sodium cyanoborohydride (1.51 g, 24.0 mmol) and the solution was stirred at room temperature for three days. Water (5 mL) was added and the mixture was concentrated in vacuo. The residue was taken up in ethyl acetate (100 mL) and aqueous 1 M KOH (100 mL) and the phases were separated. The aqueous phase was extracted with ethyl acetate (2×100 mL) and the combined organic phase was washed with brine (100 mL), dried over Na$_2$SO$_4$, and concentrated in vacuo to afford 5.80 g of crude product as a white semicrystalline oil. The product was used in the subsequent reaction step without further purification.

$^1$H NMR (400 MHz, CDCl$_3$): δ 1.22 (d, 6H), 2.88 (sep, 1H), 3.84 (s, 4H), 5.72 (bs, 1H), 7.22 (d, 2H), 7.28 (d, 2H), 7.31 (bs, 4H).

(ii) Ethyl(2S)-3-(4-{2-[(4-chlorobenzyl)(4-isopropylbenzyl)amino]-2-oxoethoxy}phenyl)-2-ethoxypropanoate To a solution of N-(4-chlorobenzyl)-N-(4-isopropylbenzyl)amine (1.64 g, 6.0 mmol) in methylene chloride (50 mL) at 0° C. were added {4-[(2S)-2,3-diethoxy-3-oxopropyl]phenoxy}acetic acid (1.48 g, 5.0 mmol) and N,N-diisopropylethylamine (2.0 mL, 11.5 mmol) followed by O-(benzotriazol-1-yl)-N,N,N',N'-tetramethyluronium tetrafluoroborate (1.93 g, 6.0 mmol) and the reaction mixture was stirred overnight. The mixture was diluted with methylene chloride (100 mL) and the organic phase was washed with 2 M HCl (3×75 mL), saturated aqueous NaHCO$_3$ (2×75 mL, some emulsions), and brine (75 mL), dried over Na$_2$SO$_4$, and concentrated in vacuo. Twice repeated purification on silica gel with methanol (0-5% gradient) in methylene chloride as the eluent and collection of pure fractions afforded 1.28 g (46%) of a colourless oil.

$^1$H NMR (400 MHz, CDCl$_3$): δ 1.16 (t, 3H), 1.19-1.28 (m, 9H), 2.82-3.02 (m, 3H), 3.35 (m, 1H), 3.61 (m, 1H), 3.97 (m, 1H), 4.17 (q, 2H), 4.49, 4.50, 4.52 and 4.54 (4s, 4H, rotamers), 4.74 and 4.77 (2s, 2H, rotamers), 6.75-6.86 (m, 2H), 7.04-7.36 (m, 10H.

(iii)(2S)-3-(4-{2-[(4-Chlorobenzyl)(4-isopropylbenzyl)amino]-2-oxoethoxy}phenyl)-2-ethoxypropanoic acid To a solution of ethyl(2S)-3-(4-{2-[(4-chlorobenzyl)(4-isopropylbenzyl)amino]-2-oxoethoxy}phenyl)-2-ethoxypropanoate (1.15 g, 2.1 mmol) in acetonitrile (100 mL) was added aqueous 0.10 M LiOH (52 mL) and the solution was stirred at room temperature overnight. After neutralisation with 5% HCl, the solvent volume was reduced in vacuo and the remaining aqueous phase was acidified with 5% HCl and extracted with ethyl acetate (3×100 mL). The combined organic phase was washed with brine (75 mL), dried over Na$_2$SO$_4$, and concentrated in vacuo to afford 1.02 g (93%) of a colourless oil.

$^1$H NMR (400 MHz, CDCl$_3$): δ 1.17 (t, 3H), 1.21-1.28 (m, 6H), 2.92 (m, 1H), 2.95 and 3.07 (AB part of ABX system, 2H), 3.44 (m, 1H), 3.61 (m, 1H), 4.04 (m, 1H), 4.49, 4.50, 4.53 and 4.55 (4s, 4H, rotamers), 4.75 and 4.78 (2s, 2H, rotamers), 6.76-6.87 (m, 2H), 7.04-7.36 (m, 10H).

Example 19

(2S)-3-(4-{2-[(Cyclohexylmethyl)(2,4-difluorobenzyl)amino]-2-oxoethoxy}phenyl)-2-ethoxypropanoic acid (i) N-(Cyclohexylmethyl)-N-(2,4-difluorobenzyl)amine To a solution of 2,4-difluorobenzylamine (2.84 g, 20.0 mmol) and cyclohexanecarbaldehyde (2.60 mL, 20.0 mmol) in methanol (100 mL) were added acetic acid (4.6 mL, 80 mmol) and sodium cyanoborohydride (1.51 g, 24.0 mmol) and the solution was stirred at room temperature for three days. Water (10 mL) was added and the mixture was concentrated in vacuo. The residue was diluted with aqueous 1 M KOH (125 mL) and ethyl acetate (100 mL) and the phases were separated. The aqueous phase was extracted with ethyl acetate (2×100 mL) and the combined organic phase was dried over Na$_2$SO$_4$ and concentrated in vacuo. Purification on a prepacked column of silica gel (Isolute® SPE Column, 50 g Si/150 mL) with ethyl acetate (33-100% gradient) in heptane as the eluent yielded 2.40 g (50%) of white solids.

$^1$H NMR (400 MHz, CDCl$_3$): δ 0.90-1.04 (m, 2H), 1.07-1.34 (m, 3H), 1.61-1.85 (m, 6H), 2.72 (d, 2H), 4.19 (s, 2H), 6.90 (m, 1H), 6.97 (m, 1H), 7.0 (bs, 1H), 7.63 (m, 1H).

(ii)Ethyl(2S)-3-(4-{2-[(cyclohexylmethyl)(2,4-difluorobenzyl)amino]-2-oxoethoxy}phenyl)-2-ethoxypropanoate To a solution of N-(cyclohexylmethyl)-N-(2,4-difluorobenzyl)amine (0.574 g, 2.00 mmol) and {4-[(2S)-2,3-diethoxy-3-oxopropyl]phenoxy}acetic acid (0.593 g, 2.00 mmol) in methylene chloride (20 mL) were added N,N-diisopropylethylamine (0.80 mL, 4.6 mmol) and O-(benzotriazol-1-yl)-N,N,N',N'-tetramethyluronium tetrafluoroborate (0.674 g, 2.10 mmol) and the reaction mixture was stirred at room temperature overnight. The mixture was diluted with methylene chloride (100 mL) and the organic phase was washed with 2 M HCl (3×75 mL), saturated aqueous NaHCO$_3$ (2×75 mL), and brine (75 mL), dried over Na$_2$SO$_4$, and concentrated in vacuo. Purification on a prepacked column of silica gel (Isolute® SPE Column, 20 g/70 mL) with methanol (0-2% gradient) in methylene chloride as the eluent yielded 0.59 g (57%) of a colourless oil.

$^1$H NMR (400 MHz, CDCl$_3$): δ 0.83-1.02 (m, 2H), 1.08-1.30 (m, 9H), 1.51-1.82 (m, 6H), 2.88-3.00 (m, 2H), 3.10-3.22 (m, 2H), 3.35 (m, 1H), 3.60 (m, 1H), 3.96 (m, 1H), 4.16 (q, 2H), 4.63 (s, 2H), 4.70 and 4.71 (2s, 2H, rotamers), 6.72-6.90 (m, 4H), 7.05-7.18 and 7.18-7.29 (2m, 3H, rotamers).

(iii)(2S)-3-(4-{2-[(Cyclohexylmethyl)(2,4-difluorobenzyl)amino]-2-oxoethoxy}phenyl)-2-ethoxypropanoic acid To a solution of ethyl(2S)-3-(4-{2-[(cyclohexylmethyl)(2,4-difluorobenzyl)amino]-2-oxoethoxy}phenyl)-2-ethoxypropanoate (0.297 g, 0.57 mmol) in acetonitrile (28 mL) was added aqueous 0.10 M LiOH (14 mL) and the solution was stirred at room temperature overnight. After neutralisation with 5% HCl, the solvent volume was reduced in vacuo and the remaining aqueous phase was acidified with 5% HCl and extracted with ethyl acetate (3×100 mL). The combined organic phase was washed with brine (100 mL), dried over Na$_2$SO$_4$, and concentrated in vacuo to afford 0.258 g (89%) of a colourless oil.

$^1$H NMR (400 MHz, CDCl$_3$): δ 0.80-1.00 (m, 2H), 1.03-1.30 (m, 6H), 1.48-1.80 (m, 6H), 2.92 (m, 1H), 3.01 (m, 1H), 3.10-3.20 (m, 2H), 3.35 (m, 1H), 3.60 (m, 1H), 3.99 (m, 1H), 4.62 (s, 2H), 4.72 (s, 2H), 6.70-6.88 (m, 4H), 7.05-7.19 and 7.19-7.29 (2m, 3H, rotamers).

Example 20

(2S)-2-Ethoxy-3-(4-{2-[ethyl(2-fluorobenzyl)amino]-2-oxoethoxy}phenyl)propanoic acid

(i)Ethyl(2S)-2-ethoxy-3-(4-{2-[ethyl(2-fluorobenzyl)amino]-2-oxoethoxy}phenyl)propanoate To a solution of N-ethyl-N-(2-fluorobenzyl)amine (0.843 g, 5.50 mmol) and {4-[(2S)-2,3-diethoxy-3-oxopropyl]phenoxy}acetic acid (1.482 g, 5.00 mmol) in methylene chloride (50 mL) were added N,N-diisopropylethylamine (2.00 mL, 11.5 mmol) and O-(benzotriazol-1-yl)-N,N,N',N'-tetramethyluronium tetrafluoroborate (1.93 g, 6.0 mmol) and the reaction mixture was stirred at room temperature overnight. The resulting solution was diluted with methylene chloride (50 mL) and the organic phase was washed with 2 M HCl (3×75 mL), saturated aqueous NaHCO$_3$ (2×75 mL), and brine (75 mL), dried over Na$_2$SO$_4$, and concentrated in vacuo. Purification on a prepacked column of silica gel (Isolute® SPE Column, 70 g/150 mL) with methanol (0-2% gradient) in methylene chloride as the eluent yielded 1.90 g (88%) of a colourless oil.

$^1$H NMR (400 MHz, CDCl$_3$): δ 1.04-1.26 (m, 9H), 2.89-2.98 (m, 2H), 3.27-3.44 (m, 3H), 3.59 (m, 1H), 3.95 (m, 1H), 4.10-4.20 (m, 2H), 4.64, 4.67, 4.70, and 4.72 (4s, 4H, rotamers), 6.76 and 6.87 (2d, 2H, rotamers), 6.97-7.32 (m, 6H).

$^{13}$C NMR (100 MHz, CDCl$_3$): δ 12.4, 13.9, 14.3, 15.1, 38.5, 41.0, 41.3 (d), 41.7, 44.3 (d), 60.9, 66.3, 67.6, 67.9, 80.4, 114.5, 114.6, 115.3 (d), 115.7 (d), 123.8 (d), 124.2 (d), 124.5 (m), 128.7, 128.7 129.1 (d), 129.5 (d), 130.3-130.6 (m), 130.5, 130.6, 156.8, 156.9, 160.9 (d), 161.1 (d), 168.0, 168.1, 172.6. (The number of peaks is larger than the number of carbon atoms due to rotamers.)

(ii) (2S)-2-Ethoxy-3-(4-{2-[ethyl(2-fluorobenzyl)amino]-2-oxoethoxy}phenyl)propanoic acid To a solution of ethyl(2S)-2-ethoxy-3-(4-{2-[ethyl(2-fluorobenzyl)amino]-2-oxoethoxy}phenyl)propanoate (0.980 g, 2.27 mmol) in acetonitrile (120 mL) was added aqueous 0.10 M LiOH (57 mL) and the reaction mixture was stirred at room temperature overnight. After neutralisation with 5% HCl, the solvent volume was reduced in vacuo and the remaining aqueous phase was acidified with 5% HCl and extracted with ethyl acetate (3×100 mL). The combined organic phase was washed brine (100 mL), dried over Na$_2$SO$_4$, and concentrated in vacuo to afford 0.868 g (95%) of a pale yellow oil.

$^1$H NMR (400 MHz, CDCl$_3$): δ 1.05-1.28 (m, 6H), 2.87-2.99 (m, 1H), 2.99-3.10 (m, 1H), 3.33-3.45 (m, 3H), 3.61 (m, 1H), 4.01 (m, 1H), 4.65, 4.68, 4.72, and 4.73 (4s, 4H, rotamers), 6.77 and 6.87 (2d, 2H, rotamers), 6.96-7.33 (m, 6H), 9.04 (bs, 1H).

$^{13}$C NMR (100 MHz, CDCl$_3$): δ 12.4, 13.9, 15.1, 38.0, 41.2, 41.4 (d), 41.7, 44.4 (d), 66.7, 67.4, 67.7, 79.8, 114.6, 114.7, 115.3 (d), 115.7 (d), 123.6 (d), 124.0 (d), 124.5 (m), 128.7, 129.2 (d), 129.6 (d), 130.0-130.8 (m), 130.6, 130.7, 156.8, 156.9, 160.9 (d), 161.1 (d), 168.4, 168.5, 175.6. (The number of peaks is larger than the number of carbon atoms due to rotamers.

Example 21

(2S)-3-(4-{2-[[4-(benzyloxy)benzyl](butyl)amino]-2-oxoethoxy}phenyl)-2-ethoxypropanoic acid

(i) Ethyl(2S)-3-(4-{2-[[4-(benzyloxy)benzyl](butyl)amino]-2-oxoethoxy}phenyl)-2-ethoxypropanoate To a solution of N-[4-(benzyloxy)benzyl]-N-butylamine (3.59 g, 12.0 mmol) and {4-[(2S)-2,3-diethoxy-3-oxopropyl]phenoxy}acetic acid (2.96 g, 10.0 mmol) in methylene chloride (100 mL) were added N,N-diisopropylethylamine (4.00 mL, 23.0 mmol) and O-(benzotriazol-1-yl)-N,N,N',N'-tetramethyluronium tetrafluoroborate (3.85 g, 12.0 mmol) and the reaction mixture was stirred at room temperature overnight. The resulting solution was diluted with methylene chloride (100 mL) and the organic phase was washed with 5% HCl (3×75 mL), saturated aqueous NaHCO$_3$ (2×75 mL), and brine (75 mL), dried over Na$_2$SO$_4$, and concentrated in vacuo. Purification on a prepacked column of silica gel (Isolute® SPE Column, 70 g/150 mL) with methanol (0-1% gradient) in methylene chloride as the eluent and collection of pure fractions yielded 1.80 g (33%) of a whitish oil.

$^1$H NMR (400 MHz, CDCl$_3$): δ 0.80-0.95 (m, 3H), 1.12-1.20 (m, 3H), 1.20-1.35 (m, 5H), 1.44-1.61 (m, 2H), 2.88-3.02 (m, 2H), 3.19-3.28 and 3.29-3.41 (2m, 3H, rotamers), 3.60 (m, 1H), 3.97 (m, 1H), 4.16 (q, 2H), 4.54 and 4.55 (2s, 2H, rotamers), 4.66 and 4.72 (2s, 2H, rotamers), 5.50 and 5.06 (2s, 2H, rotamers), 6.76-7.00 (m, 4H), 7.07-7.21 (m, 4H), 7.28-7.47 (m, 5H).

(ii) (2S)-3-(4-{2-[[4-(benzyloxy)benzyl](butyl)amino]-2-oxoethoxy}phenyl)-2-ethoxypropanoic acid To a solution of ethyl(2S)-3-(4-{2-[[4-(benzyloxy)benzyl](butyl)amino]-2-oxoethoxy}phenyl)-2-ethoxypropanoate (0.116 g, 0.21 mmol) in acetonitrile (10 mL) was added aqueous 0.10 M LiOH (5 mL) and the reaction mixture was stirred at room temperature overnight. The solvent volume was reduced in vacuo and the remaining aqueous phase was diluted with water and aqueous 1 M KOH and washed with diethyl ether (2×50 mL). The aqueous phase was acidified with 5% HCl and extracted with ethyl acetate (3×50 mL). The combined organic phase was washed with brine (50 mL), dried over $Na_2SO_4$, and concentrated in vacuo to afford 0.070 g (63%) of a colourless oil.

$^1$H NMR (400 MHz, $CDCl_3$): δ 0.83-0.95 (m, 3H), 1.10-1.20 (m, 3H), 1.20-1.36 (m, 2H), 1.42-1.62 (m, 2H), 2.95 (m, 1H), 3.05 (m, 1H), 3.19-3.29 and 3.30-3.46 (2m, 3H, rotamers), 3.61 (m, 1H), 4.02 (m, 1H), 4.54 and 4.56 (2s, 2H, rotamers), 4.68 and 4.74 (2s, 2H, rotamers), 5.04 and 5.06 (2s, 2H, rotamers), 6.76-7.00 (m, 4H), 7.09-7.22 (m, 4H), 7.28-7.47 (m, 5H).

Example 22

(2S)-3-(4-{2-[bis(4-Chlorobenzyl)amino]-2-oxoethoxy}phenyl)-2-ethoxypropanoic acid (i) Ethyl(2S)-3-(4-{2-[bis(4-chlorobenzyl)amino]-2-oxoethoxy}phenyl)-2-ethoxypropanoate To a suspension of N,N-bis(4-chlorobenzyl)amine (0.958 g, 3.60 mmol) in methylene chloride (30 mL) were added {4-[(2S)-2,3-diethoxy-3-oxopropyl]phenoxy}acetic acid (0.889 g, 3.00 mmol) and N,N-diisopropylethylamine (1.20 mL, 6.9 mmol) followed by O-(benzotriazol-1-yl)-N,N,N',N'-tetramethyluronium tetrafluoroborate (1.01 g, 3.15 mmol) and the reaction mixture was stirred at room temperature overnight. The resulting solution was diluted with methylene chloride (220 mL) and the organic phase was washed with 2 M HCl (3×50 mL), saturated aqueous $NaHCO_3$ (2×50 mL), and brine (50 mL), dried over $Na_2SO_4$, and concentrated in vacuo. Purification on a prepacked column of silica gel (Isolute® SPE Column, 50 g/150 mL) with methanol (0-2% gradient) in methylene chloride as the eluent yielded 1.02 g (62%) of an oil, which solidified upon standing to give white solids.

$^1$H NMR (400 MHz, $CDCl_3$): δ 1.17 (t, 3H), 1.23 (t, 3H), 2.90-3.00 (m, 2H), 3.36 (m, 1H), 3.61 (m, 1H), 3.97 (m, 1H), 4.17 (q, 2H), 4.50 (s, 2H), 4.76 (s, 4H), 6.80 (d, 2H), 7.03-7.11 (m, 4H), 7.15 (d, 2H), 7.21-7.35 (m, 4H).

$^{13}$C NMR (100 MHz, $CDCl_3$): δ 14.4, 15.2, 38.5, 47.6, 49.2, 61.0, 66.3, 68.1, 80.3, 114.5, 128.5, 129.0, 129.3, 129.9, 130.7, 133.7, 133.9, 134.5, 135.0, 156.6, 168.7, 172.5.

(ii)(2S)-3-(4-{2-[bis(4-Chlorobenzyl)amino]-2-oxoethoxy}phenyl)-2-ethoxypropanoic acid To a solution of ethyl(2S)-3-(4-{2-[bis(4-chlorobenzyl)amino]-2-oxoethoxy}phenyl)-2-ethoxypropanoate (0.597 g, 1.10 mmol) in acetonitrile (54 mL) was added aqueous 0.10 M LiOH (27 mL) and the reaction mixture was stirred at room temperature overnight. The solvent volume was reduced in vacuo and the remaining aqueous phase was diluted with water and aqueous 1 M KOH (to a total volume of 400 mL, pH~9) and washed with diethyl ether (2×100 mL). (The extraction process was complicated by the formation of emulsions.) The aqueous phase was acidified with 2 M HCl and extracted with ethyl acetate (4×75 mL). The combined organic phase was washed with brine (100 mL), dried over $Na_2SO_4$, and concentrated in vacuo to afford 0.475 g (84%) of a whitish oil.

$^1$H NMR (400 MHz, $CDCl_3$): δ 1.19 (t, 3H), 2.97 and 3.08 (AB part of ABX system, 2H), 3.47 (m, 1H), 3.61 (m, 1H), 4.06 (m, 1H), 4.50 (s, 4H), 4.76 (s, 2H), 6.80 (d, 2H), 7.04-7.12 (m, 4H), 7.15 (d, 2H), 7.25 (d, 2H), 7.32 (d, 2H).

$^{13}$C NMR (100 MHz, $CDCl_3$): δ 15.2, 37.7, 47.7, 49.3, 67.0, 68.0, 79.8, 114.7, 128.5, 129.0, 129.3, 129.9, 130.0, 130.9, 133.7, 133.9, 134.4, 135.0, 156.8, 168.8, 174.1.

Example 23

(2S)-3-(4-{2-[(4-tert-Butylbenzyl)(4-chlorobenzyl)amino]-2-oxoethoxy}phenyl)-2-ethoxypropanoic acid (i) N-(4-tert-Butylbenzyl)-N-(4-chlorobenzyl)amine To a solution of 4-tert-butylbenzaldehyde (3.24 g, 20.0 mmol) and 4-chlorobenzylamine (2.43 mL, 20.0 mmol) in methanol (100 mL) were added acetic acid (4.6 mL, 80 mmol) and sodium cyanoborohydride (1.51 g, 24.0 mmol) and the reaction mixture was stirred at room temperature overnight. Water (10 mL) was added and the mixture was concentrated in vacuo. The residue was taken up in ethyl acetate (50 mL) and aqueous 1 M KOH (50 mL) and the phases were separated. The aqueous phase was extracted with ethyl acetate (2×50 mL) and the combined organic phase was dried over $Na_2SO_4$, and concentrated in vacuo. Purification on a prepacked column of silica gel (Isolute® SPE Column, 70 g/150 mL) with ethyl acetate (33-100% gradient) in heptane as the eluent yielded 4.31 g (75%) of white solids.

$^1$H NMR (400 MHz, $CDCl_3$): δ 1.28 (s, 9H), 3.90 (s, 2H), 3.92 (s, 2H), 6.15 (bs, 1H), 7.28-7.33 (m, 6H), 7.40 (d, 2H).

$^{13}$C NMR (100 MHz, $CDCl_3$): δ 31.3, 34.8, 50.1, 50.8, 126.3, 129.0, 129.4, 129.5, 130.9, 131.2, 135.3, 152.6.

(ii) Ethyl(2S)-3-(4-{2-[(4-tert-butylbenzyl)(4-chlorobenzyl)amino]-2-oxoethoxy}phenyl)-2-ethoxypropanoate To a solution of {4-[(2S)-2,3-diethoxy-3-oxopropyl]phenoxy}acetic acid (0.889 g, 3.00 mmol) in methylene chloride (30 mL) were added N-(4-tert-butylbenzyl)-N-(4-chlorobenzyl)amine (1.04 g, 3.60 mmol), N,N-diisopropylethylamine (1.20 mL, 6.9 mmol) and O-(benzotriazol-1-yl)-N,N,N',N'-tetramethyluronium tetrafluoroborate (1.01 g, 3.15 mmol) and the reaction mixture was stirred at room temperature overnight. The resulting solution was diluted with methylene chloride (220 mL) and the organic phase was washed with 2 M HCl (3×50 mL), saturated aqueous $NaHCO_3$ (2×50 mL), and brine (50 mL), dried over $Na_2SO_4$, and concentrated in vacuo. Twice repeated purification on prepacked columns of silica gel (Isolute® SPE Column, 50 g/150 mL) with methanol (0-2% gradient) in methylene chloride as the eluent and collection of pure fractions yielded 0.459 g (27%) of a whitish oil.

¹H NMR (400 MHz, CDCl₃): δ 1.16 (t, 3H), 1.23 (t, 3H), 1.31 and 1.33 (2s, 9H, rotamers), 2.88-3.02 (m, 2H), 3.35 (m, 1H), 3.61 (m, 1H), 3.97 (m, 1H), 4.17 (q, 2H), 4.49 and 4.50 (2s, 2H, rotamers), 4.53 and 4.55 (2s, 2H, rotamers), 4.74 and 4.77 (2s, 2H, rotamers), 6.76-6.86 (m, 2H), 7.09 (d, 4H), 7.14 (d, 2H), 7.24, 7.31, and 7.37 (3d, 4H, rotamers).

¹³C NMR (100 MHz, CDCl₃): δ 14.3, 15.2, 31.4, 34.7, 38.6, 47.8, 48.0, 49.1, 49.4, 60.9, 66.3, 67.7, 68.1, 80.4, 114.6, 114.6, 125.7, 126.0, 126.7, 128.3, 128.4, 128.8, 129.1, 129.9, 130.6, 130.6, 132.8, 133.4, 133.7, 134.8, 135.5, 150.8, 151.2, 156.7, 168.5, 168.6, 172.6. (The number of peaks is larger than the number of carbon atoms due to rotamers.)

(iii)(2S)-3-(4-{2-[(4-tert-Butylbenzyl)(4-chlorobenzyl)amino]-2-oxoethoxy}phenyl)-2-ethoxypropanoic acid To a solution of ethyl(2S)-3-(4-{2-[(4-tert-butylbenzyl)(4-chlorobenzyl)amino]-2-oxoethoxy}phenyl)-2-ethoxypropanoate (0.400 g, 0.71 mmol) in acetonitrile (36 mL) was added aqueous 0.10 M LiOH (18 mL) and the reaction mixture was stirred at room temperature overnight. After acidification with 2 M HCl, the solvent volume was reduced in vacuo and the mixture was extracted with ethyl acetate (3×75 mL). The combined organic phase was washed with brine (75 mL), dried over Na₂SO₄, and concentrated in vacuo to afford 0.375 g (99%) of a whitish oil.

¹H NMR (400 MHz, CDCl₃): δ 1.18 (t, 3H), 1.31 and 1.33 (2s, 9H, rotamers), 2.96 and 3.07 (AB part of ABX system, 2H), 3.44 (m, 1H), 3.61 (m, 1H), 4.04 (m, 1H), 4.49 and 4.50 (2s, 2H, rotamers), 4.53 and 4.55 (2S, 2H, rotamers), 4.75 and 4.78 (2s, 2H, rotamers), 6.76-6.87 (m, 2H), 7.09 (d, 4H), 7.15 (d, 2H), 7.24, 7.31, and 7.37 (3d, 4H, rotamers).

¹³C NMR (100 MHz, CDCl₃): δ 15.2, 31.5, 34.7, 37.9, 47.8, 48.0, 49.1, 49.5, 67.0, 67.6, 68.0, 79.8, 114.7, 114.8, 125.7, 126.1, 126.8, 128.3, 128.4, 128.9, 129.2, 129.9, 130.0, 130.8, 132.7, 133.4, 133.5, 133.7, 134.8, 135.4, 150.8, 151.2, 156.9, 168.6, 168.8, 174.7. (The number of peaks is larger than the number of carbon atoms due to rotamers.)

Example 24

(2S)-3-[4-(2-{(4-Chlorobenzyl)[4-(trifluoromethyl) benzyl]amino}-2-oxoethoxy)phenyl]-2-ethoxypropanoic acid (i)Ethyl(2S)-3-[4-(2-{(4-chlorobenzyl)[4-(trifluoromethyl)benzyl]amino}-2-oxoethoxy)phenyl]-2-ethoxypropanoate To a suspension of N-(4-chlorobenzyl)-N-[4-(trifluoromethyl)benzyl]amine (0.989 g, 3.30 mmol) and {4-[(2S)-2,3-diethoxy-3-oxopropyl]phenoxy}acetic acid (0.889 g, 3.00 mmol) in methylene chloride (60 mL) were added N,N-diisopropylethylamine (1.20 mL, 6.9 mmol) and O-(benzotriazol-1-yl)-N,N,N',N'-tetramethyluronium tetrafluoroborate (1.01 g, 3.1 mmol) and the reaction mixture was stirred at room temperature overnight. The resulting solution was diluted with methylene chloride (190 mL) and the organic phase was washed with 2 M HCl (3×50 mL), saturated aqueous NaHCO₃ (2×50 mL), and brine (50 mL), dried over Na₂SO₄, and concentrated in vacuo. Twice repeated purification on prepacked columns of silica gel (Isolute® SPE Column, 70 g/150 mL) with methanol (0-2% gradient) in methylene chloride as the eluent yielded 1.02 g (59%) of a colourless oil.

¹H NMR (400 MHz, CDCl₃): δ 1.16 (t, 3H), 1.22 (t, 3H), 2.90-3.00 (m, 2H), 3.35 (m, 1H), 3.60 (m, 1H), 3.97 (m, 1H), 4.17 (q, 2H), 4.52 (s, 2H), 4.59 (s, 2H), 4.76 and 4.78 (2s, 2H, rotamers), 6.77 and 6.81 (2d, 2H, rotamers), 7.03-7.11 (m, 2H), 7.11-7.19 (m, 2H), 7.20-7.36 (m, 4H), 7.53 and 7.60 (2d, 2H rotamers).

¹³C NMR (100 MHz, CDCl₃): δ 14.4, 15.2, 38.5, 47.8, 47.9, 49.5, 61.0, 66.3, 68.1, 68.2, 80.3, 114.5, 114.5, 125.7 (m), 126.0 (m), 127.4, 128.5, 128.6, 129.0, 129.3, 129.6-131.2 (m), 129.9, 130.8, 130.8, 133.8, 134.0, 134.3, 134.9, 140.2, 140.6, 156.5, 168.8, 172.5. (The number of peaks is larger than the number of carbon atoms due to rotamers. Trifluorinated carbon not reported)

(ii)(2S)-3-[4-(2-{(4-Chlorobenzyl)[4-(trifluoromethyl)benzyl]amino}-2-oxoethoxy)phenyl]-2-ethoxypropanoic acid To a solution of ethyl(2S)-3-[4-(2-{(4-chlorobenzyl)[4-(trifluoromethyl)benzyl]amino}-2-oxoethoxy)phenyl]-2-ethoxypropanoat (0.482 g, 0.83 mmol) in acetonitrile (42 mL) was added aqueous 0.10 M LiOH (21 mL) and the solution was stirred at room temperature overnight. After acidification with 2 M HCl, the solvent volume was reduced in vacuo and the mixture was extracted with ethyl acetate (3×75 mL). The combined organic phase was washed with brine (75 mL), dried over Na₂SO₄, and concentrated in vacuo to afford 0.407 g (89%) of a colourless oil.

¹H NMR (400 MHz, CDCl₃): δ 1.18 (t, 3H), 2.97 and 3.07 (AB part of ABX system, 2H), 3.44 (m, 1H), 3.62 (m, 1H), 4.04 (m, 1H), 4.53 (s, 2H), 4.60 (s, 2H), 4.77 and 4.79 (2s, 2H, rotamers), 6.77 and 6.81 (2d, 2H, rotamers), 7.04-7.12 (m, 2H), 7.12-7.20 (m, 2H), 7.21-7.37 (m, 4H), 7.53 and 7.60 (2d, 2H, rotamers).

¹³C NMR (100 MHz, CDCl₃): δ 15.2, 37.9, 47.9, 48.0, 49.6, 66.9, 68.0, 68.1, 79.7, 114.6, 114.6, 125.7 (m), 126.0 (m), 127.3, 128.5, 128.6, 129.0, 129.3, 129.9, 130.2, 130.9, 133.8, 134.0, 134.2, 134.8, 140.1, 140.5, 156.6, 169.0, 175.2. (The number of peaks is larger than the number of carbon atoms due to rotamers. Trifluorinated carbon and quarternary carbon α to the trifluoromethyl group not reported.)

Example 25

(2S)-3-[4-(2-{bis[4-(Trifluoromethyl)benzyl] amino}-2-oxoethoxy)phenyl]-2-ethoxypropanoic acid (i) Ethyl(2S)-3-[4-(2-{bis[4-(trifluoromethyl)benzyl] amino}-2-oxoethoxy)phenyl]-2-ethoxy-propanoate To a solution of N,N-bis[4-(trifluoromethyl)benzyl]amine (0.733 g, 2.20 mmol) and {4-[(2S)-2,3-diethoxy-3-oxopropyl]phenoxy}acetic acid (0.593 g, 2.00 mmol) in methylene chloride (20 mL) were added N,N-diisopropylethylamine (0.80 mL, 4.6 mmol) and O-(benzotriazol-1-yl)-N,N,N',N'-tetramethyluronium tetrafluoroborate (0.674 g, 2.10 mmol) and the reaction mixture was stirred at room temperature for 4 h. The resulting solution was diluted with methylene chloride (130 mL) and the organic phase was washed with 5% HCl (3×75 mL), saturated aqueous NaHCO₃ (2×75 mL), and brine (75 mL), dried over Na₂SO₄, and concentrated in vacuo. Purification on a prepacked column of silica gel (Isolute® SPE Column, 70 g/150 mL) with methanol (0-1% gradient) in methylene chloride as the eluent yielded 0.91 g (74%) of a whitish oil.

¹H NMR (400 MHz, CDCl₃): δ 1.15 (t, 3H), 1.22 (t, 3H), 2.90-3.00 (m, 1H), 3.35 (m, 1H), 3.60 (m, 1H), 3.96 (m, 1H), 4.16 (q, 2H), 4.61 (s, 2H), 4.63 (s, 2H), 4.79 (s, 2H), 6.78 (d, 2H), 7.15 (d, 2H), 7.26 (m, 2H), 7.53 (d, 2H), 7.60 (d, 2H).

¹³C NMR (100 MHz, CDCl₃): δ 14.3, 15.2, 38.5, 48.2, 49.8, 60.9, 66.3, 68.2, 80.3, 114.5, 125.8 (m), 126.1 (m), 127.4, 128.6, 130.1 (q), 130.8, 130.9, 140.1, 140.5, 156.5, 169.0, 172.5. (Trifluorinated carbon not reported.)

(ii) (2S)-3-[4-(2-{bis[4-(trifluoromethyl)benzyl]amino}-2-oxoethoxy)phenyl]-2-ethoxy-propanoic acid To a solution of ethyl(2S)-3-[4-(2-{bis[4-(trifluoromethyl)benzyl]amino}-2-oxoethoxy)phenyl]-2-ethoxypropanoate (0.662 g, 1.1 mmol) in acetonitrile (54 mL) was added aqueous 0.10 M LiOH (27 mL) and the solution was stirred at room temperature overnight. The solvent volume was reduced in vacuo and the remaining aqueous phase was diluted with water and aqueous 0.10 M LiOH (to a total volume of 300 mL, pH~12) and washed with diethyl ether (2×100 mL). (The extraction process was complicated by the formation of emulsions.) The aqueous phase was acidified with 2 M HCl and extracted with ethyl acetate (3×100 mL). The combined organic phase was washed with brine (100 mL), dried over Na₂SO₄, and concentrated in vacuo to afford 0.292 g (46%) of a colourless oil.

¹H NMR (400 MHz, CDCl₃): δ 1.18 (t, 3H), 2.97 and 3.07 (AB part of ABX system, 2H), 3.46 (m, 1H), 3.62 (m, 1H), 4.05 (dd, 1H), 4.62 (s, 2H), 4.64 (s, 2H), 4.80 (s, 2H), 6.79 (d, 2H), 7.16 (d, 2H), 7.22-7.31 (m, 4H), 7.53 (d, 2H), 7.60 (d, 2H).

¹³C NMR (100 MHz, CDCl₃): δ 15.2, 37.8, 48.3, 49.9, 66.9, 68.1, 79.7, 114.6, 125.8 (m), 126.1 (m), 127.4, 128.6, 130.5 (q), 130.2, 130.9, 140.0, 140.4, 156.6, 169.1, 174.9. (Trifluorinated carbon not reported.)

Example 26

(2S)-3-(4-{2-[Benzyl(ethyl)amino]-2-oxoethoxy}phenyl)-2-ethoxypropanoic acid (i) Ethyl(2S)-3-(4-{2-[benzyl(ethyl)amino]-2-oxoethoxy}phenyl)-2-ethoxypropanoate To a solution of {4-[(2S)-2,3-diethoxy-3-oxopropyl]phenoxy}acetic acid (0.296 g, 1.00 mmol) and N-benzyl-N-ethylamine (0.149 g, 1.10 mmol) in methylene chloride (10 mL) were added N,N-diisopropylethylamine (0.40 mL, 2.3 mmol) and O-(benzotriazol-1-yl)-N,N,N',N'-tetramethyluronium tetrafluoroborate (0.353 g, 1.10 mmol) and the reaction mixture was stirred at room temperature for three days. The resulting solution was diluted with methylene chloride (90 mL) and the organic phase was washed with 2 M HCl (3×50 mL), saturated aqueous NaHCO₃ (2×50 mL), and brine (50 mL), dried over Na₂SO₄, and concentrated in vacuo. Purification on a prepacked column of silica gel (Isolute® SPE Column, 70 g/150 mL) with methanol (0-1% gradient) in methylene chloride as the eluent and collection of pure fractions yielded 0.129 g (31%) of a whitish oil.

¹H NMR (400 MHz, CDCl₃): δ 1.06-1.32 (m, 9H), 2.87-3.02 (m, 2H), 3.26-3.48 (m, 3H), 3.60 (m, 1H), 3.96 (m, 1H), 4.10-4.21 (m, 2H), 4.61 and 4.62 (2s, 2H, rotamers), 4.66 and 4.74 (2s, 2H, rotamers), 6.78 and 6.89 (2d, 2H, rotamers), 7.08-7.40 (m, 7H).

(ii) (2S)-3-(4-{2-[Benzyl(ethyl)amino]-2-oxoethoxy}phenyl)-2-ethoxypropanoic acid To a solution of ethyl(2S)-3-(4-{2-[benzyl(ethyl)amino]-2-oxoethoxy}phenyl)-2-ethoxypropanoate (0.112 g, 0.27 mmol) in acetonitrile (14 mL) was added aqueous 0.10 M LiOH (7 mL) and the reaction mixture was stirred at room temperature overnight. After neutralisation with 5% HCl, the solvent volume was reduced in vacuo and the mixture was extracted with ethyl acetate (3×50 mL). The combined organic phase was washed with brine (50 mL), dried over Na₂SO₄, and concentrated in vacuo to afford 0.096 g (92%) of a colourless oil.

¹H NMR (400 MHz, CDCl₃): δ 1.05-1.21 (m, 6H), 2.85-3.10 (m, 2H), 3.28-3.48 (m, 3H), 3.61 (m, 1H), 4.01 (m, 1H), 4.61 and 4.62 (2s, 2H, rotamers), 4.67 and 4.75 (2s, 2H, rotamers), 6.76 and 6.88 (2d, 2H, rotamers), 7.08-7.38 (m, 7H), 8.78 (bs, 1H).

Example 27

(2S)-3-(4-{2-[(4-tert-Butylbenzyl)(ethyl)amino]-2-oxoethoxy}phenyl)-2-ethoxypropanoic acid (i) Ethyl(2S)-3-(4-{2-[(4-tert-butylbenzyl)(ethyl)amino]-2-oxoethoxy}phenyl)-2-ethoxypropanoate To a solution of N-(4-tert-butylbenzyl)-N-ethylamine (0.383 g, 2.00 mmol) and {4-[(2S)-2,3-diethoxy-3-oxopropyl]phenoxy}acetic acid (0.593 g, 2.00 mmol) in methylene chloride (20 mL) were added N,N-diisopropylethylamine (0.80 mL, 4.6 mmol) and O-(benzotriazol-1-yl)-N,N,N',N'-tetramethyluronium tetrafluoroborate (0.706 g, 2.20 mmol) and the reaction mixture was stirred at room temperature overnight. The resulting solution was diluted with methylene chloride (40 mL) and the organic phase was washed with 5% HCl (50 mL), saturated aqueous NaHCO₃ (50 mL), and brine (50 mL), dried over Na₂SO₄, and concentrated in vacuo. Purification on a prepacked column of silica gel (Isolute® SPE Column, 50 g/150 mL) with methylene chloride/ethyl acetate 10:1 as the eluent yielded 0.54 g (58%) of a colourless oil.

¹H NMR (500 MHz, CDCl₃): δ 1.07-1.25 (m, 9H), 1.30 and 1.32 (2s, 9H, rotamers), 2.88-3.00 (m, 2H), 3.28-3.40 and 3.40-3.48 (2m, 3H, rotamers), 3.60 (m, 1H), 3.96 (m, 1H), 4.12-4.20 (m, 2H), 4.57 and 4.59 (2s, 2H, rotamers), 4.66 and 4.73 (2s, 2H, rotamers), 6.78 and 6.89 (2d, 2H, rotamers), 7.09-7.20 (m, 4H), 7.31 and 7.36 (2d, 2H, rotamers).

(ii)(2S)-3-(4-{2-[(4-tert-Butylbenzyl)(ethyl)amino]-2-oxoethoxy}phenyl)-2-ethoxypropanoic acid To a solution of ethyl(2S)-3-(4-{2-[(4-tert-butylbenzyl)(ethyl)amino]-2-oxoethoxy}phenyl)-2-ethoxypropanoate (0.520 g, 1.11 mmol) in THF (50 mL) was added aqueous 0.10 M LiOH (25 mL) and the solution was stirred at room temperature overnight. After neutralisation with 5% HCl, the solvent volume was reduced in vacuo and the remaining aqueous phase was acidified with 5% HCl and extracted with ethyl acetate (2×50 mL). The combined organic phase was washed with brine (50 mL), dried over Na₂SO₄, and concentrated in vacuo to afforded 0.42 g (86%) of a colourless oil.

¹H NMR (500 MHz, CDCl₃): δ 1.08-1.22 (m, 6H), 1.30 and 1.32 (2s, 9H, rotamers), 2.94 (m, 1H), 3.07 (m, 1H), 3.30-3.50 (m, 3H), 3.59 (m, 1H), 4.04 (m, 1H), 4.57 and 4.59 (2s, 2H, rotamers), 4.67 and 4.74 (2s, 2H, rotamers), 6.79 and 6.89 (2d, 2H, rotamers), 7.09-7.21 (m, 4H), 7.31 and 7.36 (2d, 2H, rotamers).

The following examples were prepared in a similar manner.

Example 28

(2S)-3-(4-{2-[(4-Cyclohexylbutyl)(2,4-difluorobenzyl)amino]-2-oxoethoxy}phenyl)-2-ethoxypropanoic acid.

Example 29

(2S)-3-(4-{2-[(2,4-Difluorobenzyl)(4-biphenylylethyl)amino]-2-oxoethoxy}phenyl)-2-ethoxypropanoic acid.

Example 30

(2S)-3-(4-{3-[(2,4-Difluorobenzyl)(heptyl)amino]-3-oxopropyl}phenyl)-2-ethoxypropanoic acid.

Example 31

(2S)-3-(4-{3-[(Cyclohexylmethyl)(hexyl)amino]-3-oxopropyl}phenyl)-2-ethoxypropanoic acid.

Example 32

(2S)-3-[4-(2-{(4-Chlorobenzyl)[2-methoxybenzyl]amino}-2-oxoethoxy)phenyl]-2-ethoxypropanoic acid.

Example 33

(2S)-3-(4-{2-[(butyl)(4-methanesulfonyloxybenzyl)amino]-2-oxoethoxy}phenyl)-2-ethoxypropanoic acid were performed by plate chemistry.

The following compounds were prepared by one of the following methods.

Method A

Reductive Amination 1.0 ml of amine solutions was added to 0.8 ml of aldehyde solutions and the resulting mixtures were stirred for 12 h in sealed 4 ml glass vial.

Then ca. 300 mg of borohydride resin (Aldrich 2.5 mmol/g loading) was manually added to the individual vials, and the mixture was stirred for 8-12 h (no seal, $H_2$-evolution; after 5 h add additional 1.0 ml of MeOH).

The mixture was filtered through a filter plate and washed once with 2.0 ml of MeOH. The filtrates were collected in 24-well plates with 4 ml glass vials. Then the solvent was removed in vacuo, using the HT-4 vacuum centrifuge (30° C., 5 h, vacramp).

To the residue was added polymer supported aldehyde resin (Novabiochem 2.85 mmol/g loading; 80-100 mg), to remove the excess of amine and 2 ml of dry THF. The resulting mixture was stirred at rt for 6-8 h, filtered through a filter plate, washed once with 1.0 ml of THF and the filtrate was collected in 24-well plates with 4 ml glass vials. Then the solvent was removed in vacuo, using the HT-4 vacuum centrifuge (30° C., 5 h, vacramp).

Method B

Amide Formation {4-[(2S)-2,3-diethoxy-3-oxopropyl]phenoxy}acetic acid

To the residues were added the acid chloride solution (2.0 ml) and PS-DIEA (Argonaut 3.83 mmol/g loading; 70-80 mg) and the resulting mixture is stirred for 5-12 h. The solutions were filtered through NH2-plates (Isolute; 500 mg) to remove any excess of acid chloride and washed with 1.0 ml THF. The filtrates were collected in 24-well plates with 4 ml glass vials.

If the formed amide does not contain a tertiary amino group, the solutions are filtered through SCX-plates (Isolute; 1 g (SCX-2, PRS & SCX-3 can be used as well)) to remove the excess of secondary amine. The SCX columns are washed with 1.0 ml of THF. The combined filtrates were collected in 24-well plates with 4 ml glass vials. If the formed amide does contain a tertiary amine group, polymer supported isocyanate (Novabiochem 1.5 mmol/g; ca 100 mg) was added and the mixture was stirred for additional 6 h at RT. This is to remove any excess of secondary amine. Then the mixtures were filtered through filter plates into 24-well plates with 4 ml glass vials, followed by a wash of 1.0 ml THF. The filtrates were collected in 24-well plates with 4 ml glass vials. The solvent was removed in vacuum, using the HT-4 vacuum centrifuge (30° C., 5 h, vacramp).

Hydrolysis

The dry residues (esters) are dissolved in 1.2 ml of THF. 400 μl of the solution is transferred to a preweighed blue well plate. The daughter plate is analysed by LC-MS (purified by preparative HPLC if needed) and the solvent is removed in vacuum, using the HT-4 vacuum centrifuge (30° C., 5 h, vacramp). The dry compounds (daughter plate) are then quantified by automatic weighing and submitted to screen.

The mother plate (containing esters dissolved in 0.8 ml THF) is treated with 0.8 ml 0.175M LiOH (per vial) overnight.

If a compound contains a tertiary amine, the solution is poured onto an SCX column (Isolute; 1 g (SCX-2, PRS & SCX-3 can be used as well)) to catch the product. The SCX columns are washed with 3×1.0 ml of THF/MeOH. Afterwards the product is eluted with 4.0 ml of MeOH, saturated with ammonia.

If a compound does not contain a tertiary amine, the solvent is removed in vacuum, using the HT-4 vacuum centrifuge (30° C., 12 h, vacramp). The dry compounds are dissolved with 1.0 ml 0.2M HCl, followed by addition of 2.0 ml of DCM. The mixtures are vigorously shaken for 30 min. Phase separators (6 ml, Whatman) are used to separate the DCM layer, which contains the product, from the water phase. The compounds are collected in 24-well plates with 4 ml glass vials. The solvent is removed in vacuum, using the HT-4 vacuum centrifuge (30° C., 5 h, vacramp).

The dry compounds are dissolved with 0.5 ml THF (or appropriate solvent) and transferred to a preweighed blue-well plate. This is repeated with 0.3 ml MeOH. The solvent is afterwards removed in vacuum, using the HT-4 vacuum centrifuge (30° C., 5 h, vacramp). The plate is analysed by LC-MS (purified by preparative HPLC if needed) and the dry compounds are then quantified by automatic weighing and submitted to screen.

The following compounds were prepared by these methods:

(2S)-3-(4-{2-[benzyl(4-isopropylbenzyl)amino]-2-oxoethoxy}phenyl)-2-ethoxypropanoic acid (2S)-2-ethoxy-3-(4-{2-[(3-ethoxypropyl)(4-isopropylbenzyl)amino]-2-oxoethoxy}phenyl)propanoic acid (2S)-3-(4-{2-[butyl(4-isopropylbenzyl)amino]-2-oxoethoxy}phenyl)-2-ethoxypropanoic acid (2S)-3-(4-{2-[(2-chlorobenzyl)(heptyl)amino]-2-oxoethoxy}phenyl)-2-ethoxypropanoic acid (2S)-2-ethoxy-3-(4-{2-[heptyl(4-isopropylbenzyl)amino]-2-oxoethoxy}phenyl)propanoic acid (2S)-3-(4-{2-[[(4-cyanocyclohexyl)methyl](4-isopropylbenzyl)amino]-2-oxoethoxy}phenyl)-2-ethoxypropanoic acid (2S)-2-ethoxy-3-(4-{2-[(4-isopropylbenzyl)(2-methoxybenzyl)amino]-2-oxoethoxy}phenyl)propanoic acid (2S)-3-(4-{2-[(2-chlorobenzyl)(4-chlorobenzyl)amino]-2-oxoethoxy}phenyl)-2-ethoxypropanoic acid (2S)-3-(4-{2-[(4-chlorobenzyl)(2,3-dimethoxybenzyl)amino]-2-oxoethoxy}phenyl)-2-ethoxypropanoic acid (2S)-3-(4-{2-[(1,3-benzodioxol-5-ylmethyl)(4-ethoxybenzyl)amino]-2-oxoethoxy}phenyl)-2-ethoxypropanoic acid (2S)-3-(4-{2-[(1,3-benzodioxol-5-ylmethyl)(3-bromobenzyl)amino]-2-oxoethoxy}phenyl)-2-ethoxypropanoic acid (2S)-3-[4-(2-{(1,3-benzodioxol-5-ylmethyl)[3-(trifluoromethyl)benzyl]amino}-2-oxoethoxy)phenyl]-2-ethoxypropanoic acid (2S)-3-(4-{2-[(3,5-dimethoxybenzyl)(4-ethoxybenzyl)amino]-2-oxoethoxy}phenyl)-2-ethoxypropanoic acid (2S)-3-(4-{2-[(3-chloro-4-fluorobenzyl)(4-ethoxybenzyl)amino]-2-oxoethoxy}phenyl)-2-ethoxypropanoic acid (2S)-2-ethoxy-3-(4-{2-[(4-ethoxybenzyl)(2-thienylmethyl)amino]-2-oxoethoxy}phenyl)propanoic acid (2S)-3-(4-{2-[benzyl(isopropyl)amino]-2-oxoethoxy}phenyl)-2-ethoxypropanoic acid (2S)-3-{4-[2-(dibenzylamino)-2-oxoethoxy]phenyl}-2-ethoxypropanoic acid (2S)-3-(4-{2-[bis(2-methoxyethyl)amino]-2-oxoethoxy}phenyl)-2-ethoxypropanoic acid (2S)-2-ethoxy-3-[4-(2-{heptyl[4-(trifluoromethyl)benzyl]amino}-2-oxoethoxy)phenyl]propanoic acid (2S)-2-ethoxy-3-[4-(2-{heptyl[4-(trifluoromethoxy)benzyl]amino}-2-oxoethoxy)phenyl]propanoic acid (2S)-2-ethoxy-3-(4-{2-[(4-ethylbenzyl)(heptyl)amino]-2-oxoethoxy}phenyl)propanoic acid (2S)-3-(4-{2-[(4-tert-butylbenzyl)(heptyl)amino]-2-oxoethoxy}phenyl)-2-ethoxypropanoic acid (2S)-2-ethoxy-3-(4-{2-[heptyl(4-isobutylbenzyl)amino]-2-oxoethoxy}phenyl)propanoic acid (2S)-3-(4-{2-[benzyl(heptyl)amino]-2-oxoethoxy}phenyl)-2-ethoxypropanoic acid (2S)-2-ethoxy-3-(4-{2-[(4-fluorobenzyl)(heptyl)amino]-2-oxoethoxy}phenyl)propanoic acid (2S)-3-(4-{2-[(4-chlorobenzyl)(heptyl)amino]-2-oxoethoxy}phenyl)-2-ethoxypropanoic acid (2S)-3-(4-{2-[(4-bromobenzyl)(heptyl)amino]-2-oxoethoxy}phenyl)-2-ethoxypropanoic acid (2S)-3-(4-{2-[butyl(4-ethylbenzyl)amino]-2-oxoethoxy}phenyl)-2-ethoxypropanoic acid (2S)-3-(4-{2-[butyl(4-tert-butylbenzyl)amino]-2-oxoethoxy}phenyl)-2-ethoxypropanoic acid (2S)-3-(4-{2-[butyl(4-isobutylbenzyl)amino]-2-oxoethoxy}phenyl)-2-ethoxypropanoic acid (2S)-3-(4-{2-[benzyl(butyl)amino]-2-oxoethoxy}phenyl)-2-ethoxypropanoic acid (2S)-3-(4-{2-[butyl(4-fluorobenzyl)amino]-2-oxoethoxy}phenyl)-2-ethoxypropanoic acid (2S)-3-(4-{2-[(4-bromobenzyl)(butyl)amino]-2-oxoethoxy}phenyl)-2-ethoxypropanoic acid (2S)-3-(4-{2-[butyl(2,4-difluorobenzyl)amino]-2-oxoethoxy}phenyl)-2-ethoxypropanoic acid (2S)-3-[4-(2-{(4-chlorobenzyl)[4-(trifluoromethoxy)benzyl]amino}-2-oxoethoxy)phenyl]-2-ethoxypropanoic acid (2S)-3-(4-{2-[(4-chlorobenzyl)(4-ethylbenzyl)amino]-2-oxoethoxy}phenyl)-2-ethoxypropanoic acid (2S)-3-(4-{2-[(4-chlorobenzyl)(4-isobutylbenzyl)amino]-2-oxoethoxy}phenyl)-2-ethoxypropanoic acid (2S)-3-(4-{2-[benzyl(4-chlorobenzyl)amino]-2-oxoethoxy}phenyl)-2-ethoxypropanoic acid (2S)-3-(4-{2-[(4-chlorobenzyl)(4-fluorobenzyl)amino]-2-oxoethoxy}phenyl)-2-ethoxypropanoic acid (2S)-3-(4-{2-[(4-bromobenzyl)(4-chlorobenzyl)amino]-2-oxoethoxy}phenyl)-2-ethoxypropanoic acid (2S)-3-(4-{2-[(4-chlorobenzyl)(2,4-difluorobenzyl)amino]-2-oxoethoxy}phenyl)-2-ethoxypropanoic acid (2S)-2-ethoxy-3-[4-(2-{(4-methylbenzyl)[4-(trifluoromethyl)benzyl]amino}-2-oxoethoxy)phenyl]propanoic acid (2S)-2-ethoxy-3-[4-(2-{(4-methylbenzyl)[4-(trifluoromethoxy)benzyl]amino}-2-oxoethoxy)phenyl]propanoic acid (2S)-2-ethoxy-3-(4-{2-[(4-ethylbenzyl)(4-methylbenzyl)amino]-2-oxoethoxy}phenyl)propanoic acid (2S)-3-(4-{2-[(4-tert-butylbenzyl)(4-methylbenzyl)amino]-2-oxoethoxy}phenyl)-2-ethoxypropanoic acid (2S)-2-ethoxy-3-(4-{2-[(4-isobutylbenzyl)(4-methylbenzyl)amino]-2-oxoethoxy}phenyl)propanoic acid (2S)-3-(4-{2-[benzyl(4-methylbenzyl)amino]-2-oxoethoxy}phenyl)-2-ethoxypropanoic acid (2S)-2-ethoxy-3-(4-{2-[(4-fluorobenzyl)(4-methylbenzyl)amino]-2-oxoethoxy}phenyl)propanoic acid (2S)-3-(4-{2-[(4-chlorobenzyl)(4-methylbenzyl)amino]-2-oxoethoxy}phenyl)-2-ethoxypropanoic acid (2S)-3-(4-{2-[(4-bromobenzyl)(4-methylbenzyl)amino]-2-oxoethoxy}phenyl)-2-ethoxypropanoic acid and (2S)-3-(4-{2-[(2,4-difluorobenzyl)(4-methylbenzyl)amino]-2-oxoethoxy}phenyl)-2-ethoxypropanoic acid.

Biological Activity

Formulations

Compounds were dissolved in DMSO to obtain 16 mM stock solutions. Before assays, stock solutions were further diluted in DMSO and culture media.

General Chemicals and Reagents

Luciferase assay reagent was purchased from Packard, USA. Restriction Enzymes were from Boehringer and Vent polymerase from New England Biolabs.

Cell Lines and Cell Culture Conditions

U2-OS, (Osteogenic sarcoma, Human) was purchased from ATCC, USA. Cells were expanded and refrozen in batches from passage number six. Cells were cultured in Dulbecco's modified Eagle medium (DMEM) with 25 mM glucose, 2 mM glutamin or 4 mM L-alanyl-L-glutamine, 10% fetal calf serum, at 5% $CO_2$. Phosphate buffered saline (PBS) without addition of calcium or magnesium was used. All cell culture reagents were from Gibco (USA) and 96-well cell culture plates were purchased from Wallah.

Plasmid Constructs for Heterologous Expression

Standard recombinant DNA techniques were carried out as described by Ausubel (7). The Luciferase reporter vector, pGL5UAS (clone consists of five copies of the GAL4 DNA binding sequence, 5'-CGACGGAGTACTGTCCTCCGAGCT-3', cloned into the SacI/XhoI sites of pGL3-Promoter (Promega). The SacI/XhoI fragment carrying the UAS sites was constructed using annealed overlapping oligonucleotides.

Expression vectors used are based upon pSG5 (Stratagene). All vectors contain an EcoRI/NheI fragment encoding the DNA binding domain of GAL4 (encoding amino acid positions 1-145 of database accession number P04386) followed by an in-frame fusion to a fragment encoding the nuclear localisation sequence from T antigen of Polyoma Virus.

The nuclear localisation sequence was constructed using annealed overlapping oligonucleotides creating NheI/KpnI sticky ends(5'-CTAGCGCTCCTAGAAGAAACGCAAG-GTTGGTAC-3'). The ligand binding domains from human and mouse PPARa and human and mouse PPARγ were PCR amplified as KpnI/BamHI fragments and cloned in frame to the GAL4 DNA binding domain and the nuclear localisation sequence. The sequence of all plasmid constructs used were confirmed by sequencing. The following expression vectors were used for transient transfections:

| vector | encoded PPAR subtype | sequence reference |
|---|---|---|
| pSGGALhPPa | human PPARα | S74349, nt 625–1530 |
| pSGGALmPPA | murine PPARα | X57638, nt 688–1573 |
| pSGGALhPPg | human PPARγ | U63415, nt 613–1518 |
| pSGGALmPPg | murine PPARγ | U09138, nt 652–1577 | refers to nucleotide positions of data base entry used to express the ligand binding domain.

Transient Transfections

Frozen stocks of cells from passage number six were thawed and expanded to passage number eight before transfections. Confluent cells were trypsinised, washed and pelleted by centrifugation at 270×g for 2 minutes. The cell pellet was resuspended in cold PBS to a cell concentration of about 18×106 cells/ml. After addition of DNA, the cell suspension was incubated on ice for approximately 5 minutes before electroporation at 230 V, 960, μF in Biorad's Gene Pulser" in 0.5 ml batches. A total of 50 jig DNA was added to each batch of 0.5 ml cells, including 2.5 yg expression vector, 25 jig reporter vector and 22.5 ttg unspecific DNA (Bluescript, Stratagene).

After electroporation, cells were diluted to a concentration of 320'000 cells/ml in DMEM without phenol red, and approximately 25'000 cells/well were seeded in 96-well plates. In order to allow cells to recover, seeded plates were incubated at 37° C. for 3-4 hours before addition of test compounds. In assays for PPARa, the cell medium was supplemented with resin-charcoal stripped fetal calf serum (FCS) in order to avoid background activation by fatty acid components of the FCS. The resin-charcoal stripped FCS was produced as follows; for 500 ml of heat-inactivated FCS, 10 g charcoal and 25 g Bio-Rad Analytical Grade Anion Exchange Resin 200-400 mesh were added, and the solution was kept on a magnetic stirrer at room temperature over night. The following day, the FCS was centrifuged and the stripping procedure was repeated for 4-6 hours. After the second treatment, the FCS was centrifuged and filter sterilised in order to remove remnants of charcoal and resin.

Assay Procedure

Stock solutions of compounds in DMSO were diluted in appropriate concentration ranges in master plates. From master plates, compounds were diluted in culture media to obtain test compound solutions for final doses.

After adjustment of the amount of cell medium to 75 μl in each well, 50 its test compound solution was added. Transiently transfected cells were exposed to compounds for about 24 hours before the luciferase detection assay was performed. For luciferase assays, 10041 of assay reagent was added manually to each well and plates were left for approximately 20 minutes in order to allow lysis of the cells. After lysis, luciferase activity was measured in a 1420 Multiwell counter, Victor, from Wallach.

Reference compounds The TZD pioglitazone was used as reference substance for activation of both human and murine PPARγ. 5,8,11,14-Eicosatetrayonic acid (ETYA) was used as reference substance for human PPARα.

Calculations and analysis For calculation of $EC_{50}$ values, a concentration-effect curve was established. Values used were derived from the average of two or three independent measurements (after subtraction of the background average value) and were expressed as the percentage of the maximal activation obtained by the reference compound. Values were plotted against the logarithm of the test compound concentration. $EC_{50}$ values were estimated by linear intercalation between the data points and calculating the concentration required to achieve 50% of the maximal activation obtained by the reference compound.

The compounds of described herein generally have an $EC_{50}$ of less than 0.5, μmol/l for PPARα and preferred compounds have an $EC_{50}$ of less than 0.051 μmol/l for PPARα. The compounds described herein are a select group of compounds in that they are more potent with respect to PPARα than with respect to PPARγ. It is believed that this relationship is important with respect to the pharmacological activity of the compounds and to their therapeutic profile.

The compounds of formula (V) have an $EC_{50}$ of less than 0.1 μmol/l for PPARα and particular compounds have an $EC_{50}$ of less than 0.01 μmol/l. Additionally in particular compounds the ratio of the $EC_{50}$ (PPARγ): $EC_{50}$ (PPARα) is greater than 150:1. It is believed that this ratio is important with respect to the pharmacological activity of the compounds and to their therapeutic profile.

| Example no | $EC_{50}$ PPARα (μM) | ratio $EC_{50}$ (PPARγ): $EC_{50}$ (PPARα) |
|---|---|---|
| 22 | 0.003 | >1000 |
| 23 | 0.008 | >400 |
| 25 | 0.003 | >900 |

In addition the compounds of the present invention generally exhibit improved DMPK (Drug Metabolism and Pharmacokinetic) properties for example they can exhibit improved metabolic stability in vitro and also exhibit favourable dose response curves in vivo. The compounds also can have a promising toxicological profile.

A number of embodiments of the invention have been described. Nevertheless, it will be understood that various modifications may be made without departing from the spirit and scope of the invention. Accordingly, other embodiments are within the scope of the following claims.

What is claimed is:

1. A compound of formula (I)

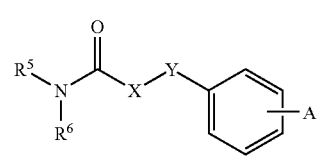

formula (I)

wherein,

A is situated in the ortho, meta or para position and represents formula II or formula III, below:

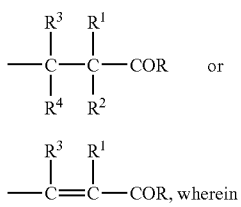

Formula II

Formula III where R is H or alkyl;
—OR$^a$, wherein R$^a$ represents hydrogen, alkyl, aryl or alkylaryl;
—NR$^a$R$^b$, wherein R$^a$ and R$^b$ are the same or different and R$^a$ is as defined above and R$^b$ represents hydrogen, alkyl, aryl, alkylaryl, cyano, —OH, —Oalkyl,—Oaryl, —Oalkylaryl, —COR$^c$ or —SO$_2$R$^d$, wherein R$^c$ represents hydrogen, alkyl, aryl or alkylaryl and R$^d$ represents alkyl, aryl or alkylaryl;

R$^1$ is alkyl, aryl, alkenyl, alkynyl, or when A is formula II,

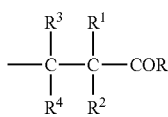

then R$^1$ can also be cyano;
—OR$^e$, wherein R$^e$ is alkyl, acyl, aryl or alkylaryl;
—O—[CH$_2$]$_m$—OR$^f$, wherein R$^f$ represents hydrogen, alkyl, acyl, aryl or alkylaryl and m represents an integer 1-8;
—OCONR$^a$R$^c$, wherein R$^a$ and R$^c$ are as defined above;
—SR$^d$, wherein R$^d$ is as defined above;
—SO$_2$NR$^a$R$^f$, wherein R$^f$ and R$^a$ are as defined above;
—SO$_2$OR$^a$, wherein R$^a$ is as defined above;
—COOR$^d$, wherein R$^d$ is as defined above;

R$^2$ is hydrogen, halogen, alkyl, aryl, or alkylaryl,
R$^3$ and R$^4$ are the same or different and each represents hydrogen, alkyl, aryl, or alkylaryl;
Y represents O, S or a single bond;
X is alkenyl;
R$^5$ and R$^6$ independently represent hydrogen, C$_{1-13}$alkyl, C$_{2-10}$alkenyl or C$_{2-10}$alkynyl each of which is optionally substituted by one or more of the following which may be the same or different: C$_{3-8}$cycloalkyl, C$_{3-8}$cycloalkenyl, aryl, heterocyclyl, heteroaryl, C$_{1-8}$alkoxy (optionally substituted by one or more fluoro), C$_{3-8}$cycloalkoxy, C$_{3-8}$cycloalkenyloxy, aryloxy, heterocyclyloxy, heteroaryloxy, C$_{3-8}$cycloalkyl C$_{1-8}$alkoxy, aryl C$_{1-8}$alkoxy, heterocyclyl C$_{1-8}$ alkoxy or heteroaryl C$_{1-8}$ alkoxy, fluorine or hydroxyl and wherein each of these substituents may optionally be substituted on carbon with one or more substituents which may be the same or different and selected from C$_{1-8}$alkyl, C$_{3-8}$cycloalkyl (optionally substituted by C$_{1-8}$alkyl, C$_{1-8}$alkoxy (optionally substituted by one or more fluoro), halogen, hydroxy, nitro or cyano), aryl (optionally substituted by C$_{1-8}$alkyl, C$_{1-8}$alkoxy (optionally substituted by one or more fluoro), halogen, hydroxy, nitro or cyano), heterocyclyl (optionally substituted by C$_{1-6}$alkyl on any nitrogen), heteroaryl (optionally substituted by C$_{1-8}$alkyl, C$_{1-8}$alkoxy (optionally substituted by one or more fluoro), halogen, hydroxy, nitro or cyano), C$_{1-8}$alkoxy (optionally substituted by one or more fluoro), C$_{3-8}$cycloalkoxy, C$_{3-8}$ cycloalkyl C$_{1-8}$alkoxy, aryloxy (optionally substituted by C$_{1-8}$alkyl, C$_{1-8}$alkoxy (optionally substituted by one or more fluoro), halogen, hydroxy, nitro or cyano), aryl C$_{1-8}$alkoxy (wherein the aryl part is optionally substituted by C$_{1-8}$alkyl, C$_{1-8}$alkoxy (optionally substituted by one or more fluoro), halogen, hydroxy, nitro or cyano), halogen, amino, nitro, hydroxy, methylsulfonyl, methylsulfonyloxy, cyano or methylenedioxy, or R$^5$ and R$^6$ independently represent C$_3$-C$_8$ cycloalkyl; C$_3$-C$_8$ cycloalkenyl; aryl; heterocyclyl; or heteroaryl; wherein each of these groups is optionally substituted by one or more of the following: C$_{1-8}$alkyl, C$_{1-8}$alkoxy (optionally substituted by one or more fluoro), halogen, hydroxy, nitro or cyano), aryl (optionally substituted by C$_{1-8}$alkyl, C$_{1-8}$alkoxy (optionally substituted by one or more fluoro), halogen, hydroxy, nitro or cyano;

or R$^5$ and R$^6$ together with the nitrogen atom to which they are attached form a single or a fused heterocyclic system.

2. The compound of claim 1, wherein A is situated in the para position.

3. The compound of claim 1, wherein A is

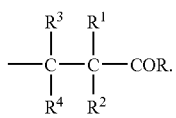

4. The compound of claim 3 wherein R$^1$ is OR$^c$ and R$^c$ is alkyl.

5. The compound of claim 4, wherein R$^c$ is ethyl.

6. The compound of claim 1 wherein Y is O.

7. The compound of claim 1 wherein X is a branched alkylenyl.

8. The compound of claim 1 wherein R$^5$ is H, alkyl, aryl, or arylalkyl.

9. The compound of claim 1 wherein R$^6$ is aryl, heteroaryl, arylalkyl or heteroarylalkyl.

10. The compound of claim 9 wherein R$^6$ is phenylalkyl.

11. The compound of claim 10 wherein R$^6$ is phenylethyl.

12. The compound of claim 11 wherein the phenylethyl is substituted with 1 or 2 R$^7$.

13. The compound of claim 10 wherein R$^6$ is phenylmethyl.

14. The compound of claim 1 wherein R$^6$ is selected from the group consisting of aryl, arylalkyl, alkyl,heteroaryl, heteroarylalkyl, C$_3$-C$_8$ cycloalkyl, arylheterocyclyl, wherein each of said R$^6$ is unsubstituted or substituted by one or two substituents.

15. The compound of claim 14 wherein R$^6$ is aryl or arylalkyl, wherein the aryl is phenyl or napthyl, and alkyl is selected from the group consisting of methyl and ethyl.

16. The compound of claim 14 wherein R$^6$ is heteroaryl or heteroarylalkyl, and said heteroaryl or heteroarylalkyl is unsubstituted or substituted with from one to three substituents; and the alkyl is selected from the group consisting of methyl and ethyl.

17. The compound of claim 1, wherein R$^5$ and R$^6$, together with the nitrogen to which they are attached, form a single heterocyclic system.

18. The compound of claim 1, wherein when A is CH$_2$CH(OC$_2$H$_5$)COOC$_2$H$_5$ or CH$_2$CH(OC$_2$H$_5$)COOH; Y is O; and R$^5$ represents a C$_{2-4}$alkyl group then R$^6$ does not represent a group of formula

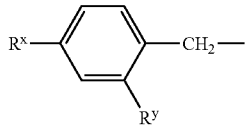

wherein R$^x$ represents chloro, trifluoromethyl or trifluoromethoxy, and R$^y$ represents H or fluoro.

19. The compound of claim 1, wherein when A is CH$_2$CH(OC$_2$H$_5$)COOC$_2$H$_5$ or CH$_2$CH(OC$_2$H$_5$)COOH; Y is O; n is 1 and R$^5$ represents hexyl or heptyl then R$^6$ does not represent a group of formula

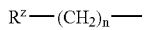

wherein R$^z$ represents phenyl,2,4-difluorophenyl or cyclohexyl, and n is 1 or 2.

20. The compound of claim 1, wherein the compound of formula (I) wherein the compound is not a compound selected from the group consisting of
- (2S)-4-[2-[[2-[[(2,6-dichlorophenyl)methyl]thio]ethyl]amino]-2-oxoethoxy]-α-methoxy-benzenepropanoic acid;
- (2S)-4-[2-[butyl(1-phenylethyl)amino]-2-oxoethoxy]-α-methoxy-benzenepropanoic acid;
- (2S)-α-methoxy-4-[2-oxo-2-[[2-(3-pyridinyl)ethyl]amino]ethoxy]-benzenepropanoic acid;
- (2S)-α-methyl-4-[2-oxo-2-[[2-(4-phenoxyphenyl)ethyl]amino]ethoxy]-α-phenoxy-benzenepropanoic acid;
- (2S)-α-methoxy-4-[2-[(1-methyl-3-phenylpropyl)amino]-2-oxoethoxy]-benzenepropanoic acid;
- (2S)-α-methoxy-4-[2-oxo-2-[[2-(4-phenoxyphenyl)ethyl]amino]ethoxy]-benzenepropanoic acid;
- (2S)-α-methoxy-4-[2-oxo-2-[4-[4-(trifluoromethyl)phenyl]-1-piperazinyl]ethoxy]-benzenepropanoic acid;
- (2S)-4-[2-[[2-(4-bromophenyl)ethyl]amino]-2-oxoethoxy]-α-methoxy-benzenepropanoic acid;
- (2S)-4-[2-[4-[(4-chlorophenyl)phenylmethyl]-1-piperazinyl]-2-oxoethoxy]-α-methoxy-benzenepropanoic acid;
- (2S)-4-[2-[[2-[ethyl(3-methylphenyl)amino]ethyl]amino]-2-oxoethoxy]-α-methoxy-benzenepropanoic acid;
- α-methoxy-α-methyl-4-[2-oxo-2-[[2-(4-phenoxyphenyl)ethyl]amino]ethoxy]-benzenepropanoic acid;
- (2S)-α-methoxy-4-[2-[(3-methylbutyl)amino]-2-oxoethoxy]-benzenepropanoic acid;
- (2S)-4-[2-[4-(diphenylmethyl)-1-piperazinyl]-2-oxoethoxy]-α-methoxy-benzenepropanoic acid;
- (2S)-4-[2-(heptylamino)-2-oxoethoxy]-α-methoxy-α-methyl-benzenepropanoic acid;
- 4-[2-[4-(2-fluorophenyl)-1-piperazinyl]-2-oxoethoxy]-α-methoxy-, benzenepropanoic acid;
- (2S)-4-[2-[4-(4-chlorobenzoyl)-1-piperidinyl]-2-oxoethoxy]-α-methoxy-, benzenepropanoic acid;
- (2S)-4-[2-[ethyl[(3-methylphenyl)methyl]amino]-2-oxoethoxy]-α-methoxy-benzenepropanoic acid;
- (2S)-α-methoxy-4-[2-oxo-2-[(4-phenoxyphenyl)amino]ethoxy]-benzenepropanoic acid;
- (2S)-α-methoxy-4-[2-[(1-methylhexyl)amino]-2-oxoethoxy]-benzenepropanoic acid;
- (2S)-4-[2-[([1,1'-biphenyl]-4-ylmethyl)amino]-2-oxoethoxy]-α-methoxy-benzenepropanoic acid;
- 3-[2-[[cis-4-(1,1-dimethylethyl)cyclohexyl]amino]-2-oxoethoxy]-α-methoxy-benzenepropanoic acid;
- (2S)-4-[2-[4-(3-chlorophenyl)-1-piperazinyl]-2-oxoethoxy]-α-methoxy-benzenepropanoic acid;
- (2S)-α-methoxy-4-[2-[methyl[(1S)-1-phenylethyl]amino]-2-oxoethoxy]-benzenepropanoic acid;
- (2S)-α-methoxy-4-[2-[4-(4-methylphenyl)-1-piperazinyl]-2-oxoethoxy]-benzenepropanoic acid;
- (2S)-α-methoxy-4-[2-[[3-(methylphenylamino)propyl]amino]-2-oxoethoxy]-benzenepropanoic acid;
- (2S)-4-[2-(cyclobutylamino)-2-oxoethoxy]-α-methoxy-benzenepropanoic acid;
- (2S)-α-methyl-4-[2-oxo-2-[[2-(4-phenoxyphenyl)ethyl]amino]ethoxy]-α-[4-(trifluoromethoxy)phenoxy]-benzenepropanoic acid;
- (2S)-4-[2-(heptylamino)-2-oxoethoxy]-α-methoxy-benzenepropanoic acid;
- (2S)-4-[2-[4-(4-fluorophenyl)-1-piperazinyl]-2-oxoethoxy]-α-methoxy-benzenepropanoic acid;
- (2S)-α-methoxy-4-[2-[[(1S)-1-(1-naphthalenyl)ethyl]amino]-2-oxoethoxy]-benzenepropanoic acid;
- (2S)-α-methoxy-4-[2-oxo-2-[[(1R)-1-phenylethyl](phenylmethyl)amino]ethoxy]-benzenepropanoic acid;
- (2S)-4-[2-[(3,3-diphenylpropyl)amino]-2-oxoethoxy]-α-methoxy-benzenepropanoic acid;
- (2S)-4-[2-[[trans-4-(1,1-dimethylethyl)cyclohexyl]amino]-2-oxoethoxy]-α-methoxy-benzenepropanoic acid;
- (2S)-α-methyl-4-[2-oxo-2-[[2-(4-phenoxyphenyl)ethyl]amino]ethoxy]-α-phenoxy-, ethyl ester-benzenepropanoic acid;
- (2S)-4-[2-[(2,2,3,3,4,4,4-heptafluorobutyl)amino]-2-oxoethoxy]- α-methoxy-benzenepropanoic acid;
- (2S)-4-[2-(3,4-dihydro-2(1H)-isoquinolinyl)-2-oxoethoxy]-α-methoxy-benzenepropanoic acid;
- (2S)-3-[2-[[2-(4-ethylphenyl)ethyl]amino]-2-oxoethoxy]-α-methoxy-benzenepropanoic acid;
- (2S)-α-methoxy-4-[2-[(1-naphthalenylmethyl)amino]-2-oxoethoxy]-benzenepropanoic acid;
- (2S)-4-[2-[[(4-chlorophenyl)phenylmethyl]amino]-2-oxoethoxy]-α-methoxy-benzenepropanoic acid;
- (2S)-α-methoxy-4-[2-oxo-2-[[2-(2-pyridinyl)ethyl]amino]ethoxy]-benzenepropanoic acid;
- (2S)-α-methoxy-4-[2-oxo-2-[[(1S)-1-phenylethyl]amino]ethoxy]-benzenepropanoic acid;
- (2S)-4-[2-(cyclopentylamino)-2-oxoethoxy]-α-methoxy-benzenepropanoic acid;
- (2S)-4-[2-[4-[bis(4-fluorophenyl)methyl]-1-piperazinyl]-2-oxoethoxy]-α-methoxy-benzenepropanoic acid;
- 4-[2-[cyclohexyl[2-(4-ethylphenyl)ethyl]amino]-2-oxoethoxy]-α-ethoxy-benzenepropanoic acid;
- (2S)-4-[2-[(1,3-benzodioxol-5-ylmethyl)amino]-2-oxoethoxy]-α-methoxy-benzenepropanoic acid;
- D-Phenylalanine, N-[[4-[(2S)-2-carboxy-2-methoxyethyl]phenoxy]acetyl]-,α-methyl ester;
- (2S)-4-[2-[4-[(4-fluorophenyl)methyl]-1-piperazinyl]-2-oxoethoxy]-α-methoxy-benzenepropanoic acid;
- α-methoxy-3-[2-oxo-2-[(4-phenoxyphenyl)amino]ethoxy]-benzenepropanoic acid;
- (2S)-α-methoxy-4-[2-[(1-methylbutyl)amino]-2-oxoethoxy]-benzenepropanoic acid;
- (2S)-α-methoxy-4-[2-[methyl(1-naphthalenylmethyl)amino]-2-oxoethoxy]-benzenepropanoic acid;

(2S)-3-[2-[[trans-4-(1,1-dimethylethyl)cyclohexyl]amino]-2-oxoethoxy]-α-methoxy-benzenepropanoic acid;

(2S)-4-[2-[4-[(4-chlorophenyl)methyl]-1-piperazinyl]-2-oxoethoxy]-α-methoxy-benzenepropanoic acid;

(2S)-4-[2-[4-(4-fluorobenzoyl)-1-piperidinyl]-2-oxoethoxy]-α-methoxy-benzenepropanoic acid;

(2S)-4-[2-[ethyl[(2-fluorophenyl)methyl]amino]-2-oxoethoxy]-α-methoxy-benzenepropanoic acid;

(2S)-α-methoxy-4-[2-[[2-(4-methoxyphenoxy)ethyl]amino]-2-oxoethoxy]-benzenepropanoic acid;

(2S)-4-[2-[(1,3-dimethylbutyl)amino]-2-oxoethoxy]-α-methoxy-benzenepropanoic acid;

(2S)-α-(4-fluorophenoxy)-α-methyl-4-[2-oxo-2-[2-(4-phenoxyphenyl)ethyl]amino]ethoxy]-benzenepropanoic acid;

(2S)-4-[2-[(3,3-dimethylbutyl)amino]-2-oxoethoxy]-α-methoxy-benzenepropanoic acid;

(2S)-4-[2-[4-(4-chlorophenyl)-3-methyl-1-piperazinyl]-2-oxoethoxy]-α-methoxy-benzenepropanoic acid;

(2S)-α-methoxy-4-[2-oxo-2-[[(1R)-1-phenylethyl]amino]ethoxy]-benzenepropanoic acid;

(2S)-4-[2-[4-(4-acetylphenyl)-1-piperazinyl]-2-oxoethoxy]-α-methoxy-benzenepropanoic acid;

(2S)-4-[2-[(3-ethoxy-3-oxopropyl)(phenylmethyl)amino]-2-oxoethoxy]-α-methoxy-benzenepropanoic acid;

(2S)-4-[2-[[cis-4-(1,1-dimethylethyl)cyclohexyl]amino]-2-oxoethoxy]-α-methoxy-benzenepropanoic acid;

(2S)-α-ethyl-4-[2-oxo-2-[[2-(4-phenoxyphenyl)ethyl]amino]ethoxy]-α-phenoxy-benzenepropanoic acid;

(2S)-4-[2-(hexylamino)-2-oxoethoxy]-α-methoxy-benzenepropanoic acid;

(2S)-α-methoxy-4-[2-oxo-2-[(2-phenylethyl)(phenylmethyl)amino]ethoxy]-benzenepropanoic acid;
and
(2S)-4-[2-[ethyl[2-(4-methoxyphenyl)-1-methylethyl]amino]-2-oxoethoxy]-α-methoxy-benzenepropanoic acid.

\* \* \* \* \*

UNITED STATES PATENT AND TRADEMARK OFFICE
CERTIFICATE OF CORRECTION

| | | |
|---|---|---|
| PATENT NO. | : 7,488,844 B2 | Page 1 of 1 |
| APPLICATION NO. | : 11/026806 | |
| DATED | : February 10, 2009 | |
| INVENTOR(S) | : Alstermark et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 168 days Delete the phrase "by 168 days" and insert -- by 333 days --

Signed and Sealed this

Fourth Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,488,844 B2  Page 1 of 1
APPLICATION NO. : 11/026806
DATED : February 10, 2009
INVENTOR(S) : Eva-Lotte Lindstedt Alstermark et al.

It is certified that error appears in the above-identified patent and that said Letters Patent is hereby corrected as shown below:

Column 75, line 25, delete the formula.

Column 76, line 33, "$OR^c$ and $R^{c}$" should be -- $OR^e$ and $R^e$ --.

Column 76, line 35, "$R^{c}$" should be -- $R^e$ --.

Signed and Sealed this

Thirty-first Day of August, 2010

David J. Kappos
*Director of the United States Patent and Trademark Office*